(12) United States Patent
Boulet et al.

(10) Patent No.: US 7,410,996 B2
(45) Date of Patent: Aug. 12, 2008

(54) 3-ARYLOXY/THIO-2,3-SUBSTITUTED PROPANAMINES AND THEIR USE IN INHIBITING SEROTONIN AND NOREPINEPHRINE REUPTAKE

(75) Inventors: Serge Louis Boulet, Fishers, IN (US); Sandra Ann Filla, Brownsburg, IN (US); Peter Thaddeus Gallagher, Surrey (GB); Kevin John Hudziak, Indianapolis, IN (US); Anette Margareta Johansson, Indianapolis, IN (US); Rushad E. Karanjawala, Zionsville, IN (US); John Joseph Masters, Fishers, IN (US); Victor Giulio Matassa, Hirschberg (DE); Brian Michael Mathes, Indianapolis, IN (US); Richard Edmund Rathmell, Ash Vale (GB); Maria Ann Whatton, Bracknell (GB); Chad Nolan Wolfe, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 453 days.

(21) Appl. No.: 10/533,328

(22) PCT Filed: Oct. 24, 2003

(86) PCT No.: PCT/US03/31513

§ 371 (c)(1),
(2), (4) Date: May 2, 2005

(87) PCT Pub. No.: WO2004/043903

PCT Pub. Date: May 27, 2004

(65) Prior Publication Data

US 2006/0173035 A1    Aug. 3, 2006

Related U.S. Application Data

(60) Provisional application No. 60/424,176, filed on Nov. 5, 2002.

(51) Int. Cl.
*A61K 31/381* (2006.01)
*C07D 333/64* (2006.01)

(52) U.S. Cl. .................................. 514/443; 549/51
(58) Field of Classification Search ................ 514/443; 549/51
See application file for complete search history.

(56) References Cited

U.S. PATENT DOCUMENTS

| 4,018,895 A | 4/1977 | Schmiegel et al. |
| 5,023,269 A | 6/1991 | Robertson et al. |
| 5,776,969 A * | 7/1998 | James .................. 514/418 |

FOREIGN PATENT DOCUMENTS

| EP | 0373836 A | 6/1990 |
| GB | 2 060 622 A | 5/1981 |
| WO | WO 96/09288 A | 3/1996 |
| WO | WO 97/45115 A | 3/1996 |
| WO | WO 00/02551 A | 1/2000 |
| WO | WO 01/62714 A | 8/2001 |
| WO | WO 02/094262 A | 11/2002 |
| WO | WO 2004/043931 A1 | 5/2004 |
| WO | WO 2004/043904 A1 | 5/2007 |

OTHER PUBLICATIONS

King, Med Chem: Principle and Practice (1994), p. 206-209.*
Meloni P. et al., XP000605241, "Potential Antidepressant Agents-Alpha-Aryloxy-Benzyl Derivatives of Ethanolamine and Morpholine" European Journal of Medicinal Chemistry, editions Scientifique Elsevier, Paris, Fr, vol. 19, No. 3, 1984, pp. 235-242.

* cited by examiner

*Primary Examiner*—Taofiq A Solola
(74) *Attorney, Agent, or Firm*—Robert D. Titus; Arvie J. Anderson

(57) ABSTRACT

There is provided a compound of formula (I) wherein A is selected from —O— and —S—; X is selected from phenyl optionally substituted with up to 5 substituents each independently selected from halo, $C_1$-$C_4$ alkyl and $C_1$-$C_4$ alkoxy, thienyl optionally substituted with up to 3 substituents each independently selected from halo and $C_1$-$C_4$ alkyl, and $C_2$-$C_8$ alkyl, $C_2$-$C_8$ alkenyl, $C_3$-$C_8$ cycloalkyl and $C_4$-$C_8$ cycloalkylalkyl, each of which may be optionally substituted with up to 3 substituents each independently selected from halo, $C_1$-$C_4$ alkyl, $C_1$-$C_4$ alkoxy, $C_1$-$C_4$ alkyl-$S(O)_n$— where n is 0, 1 or 2, —$CF_3$, —CN and —$CONH_2$; Y is selected from phenyl, naphthyl, dihydrobenzothienyl, benzothiazolyl, benzoisothiazolyl, quinolyl, isoquinolyl, naphthyridyl, thienopyridyl, indanyl, 1,3-benzodioxolyl, benzothienyl, indolyl and benzofuranyl, each of which may be optionally substituted with up to 4 or, where possible, up to 5 substituents each independently selected from halo, $C_1$-$C_4$ alkyl, $C_1$-$C_4$ alkoxy, $C_1$-$C_4$ alkyl-$S(O)_n$— where n is 0, 1 or 2, nitro, acetyl, —$CF_3$, —$SCF_3$ and cyano; and when Y is indolyl it may be substituted or further substituted by an N-substituent selected from $C_1$-$C_4$ alkyl; Z is selected from $OR_3$ or F, wherein $R_3$ is selected from H, $C_1$-$C_6$ alkyl and phenyl $C_1$-$C_6$ alkyl; $R_1$ and $R_2$ are each independently H or $C_1$-$C_4$ alkyl; and pharmaceutically acceptable salts thereof with the proviso that when Y is optionally substituted phenyl or optionally substituted 1,3-benzodioxolyl and Z is $OR_3$ and X is optionally substituted phenyl then A is —S—.

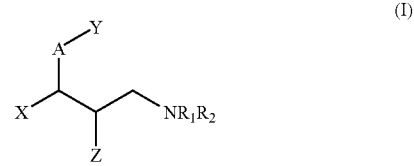

(I)

3 Claims, No Drawings

3-ARYLOXY/THIO-2,3-SUBSTITUTED PROPANAMINES AND THEIR USE IN INHIBITING SEROTONIN AND NOREPINEPHRINE REUPTAKE

This application is a United States national phase entry, pursuant to 35 U.S.C. 371, of PCT/US2003/031513, filed Oct. 24, 2003, which claims the benefit of U.S. provisional patent application Ser. No. 60/424,176, filed Nov. 5, 2002.

This invention relates to 3-aryloxy/thio-2,3-substituted propanamines, and to their use in inhibiting serotonin and norepinephrine reuptake.

Serotonin (5-HT) has been implicated in the aetiology of many disease states and has been found to be of importance in mental illnesses, depression, anxiety, schizophrenia, eating disorders, obsessive compulsive disorder (OCD) and migraine. Indeed many currently used treatments of these disorders are thought to act by modulating serotonergic tone. During the last decade, multiple serotonin receptor subtypes have been characterised. This has led to the realisation that many treatments act via the serotonergic system, such as selective serotonin reuptake inhibitor (SSRI) antidepressants which increase serotonin transmission, such as, for example, the hydrochloride salt of fluoxetine.

Drugs that exert their main action on the norepinhrinergic system have been available for some time, however their lack of selectivity made it difficult to determine specific clinical effects produced by a selective action on norepinephrine reuptake. Accumulating evidence indicates that the norepinephrinergic system modulates drive and energy, whereas the serotonergic system modulates mood. Thus norepinephrine appears to play an important role in the disturbances of vegetative function associated with affective, anxiety and cognitive disorders. Atomoxetine hydrochloride is a selective inhibitor of norepinephrine, and is currently marketed for the treatment of attention deficit hyperactivity disorder (ADHD).

Norepinephrine and serotonin receptors are known to interact anatomically and pharmacologically. Compounds that affect only serotonin have been shown to exhibit modulatory effects on norepinephrine, pointing toward an important relationship between the two neurotransmitter systems.

Duloxetine, (+)—N-methyl-3-(1-naphthalenyloxy)-2-thiophenepropanamine hydrochloride, inhibits the reuptake of both norepinephrine and serotonin, and is currently under development for the treatment of depression and urinary incontinence. The compound duloxetine was disclosed in U.S. Pat. Nos. 5,023,269 and 4,956,388.

U.S. Pat. No. 4,018,895 describes aryloxyphenyl propanamine compounds including compunds of the formula

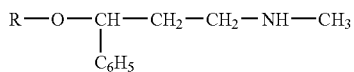

Where R is, for example, phenyl, substituted phenyl, tolyl or anisyl. The compounds block the uptake of various physiologically active monoamines including serotonin, norepinephrine and dopamine. Some of the compounds are selective to one of the monoamines and others have multiple activity. The compounds are indicated as psychotropic agents. Some are also antagonists of apomorphine and/or reserpine.

WO 00/02551 describes inter alia 3-aryloxy-3-substituted propanamines which are active at the NMDA receptor and serotonin reuptake site.

WO 97/45115 describes compounds which inhibit glycine transport via the GlyT-1 or GlyT-2 transporters. Some of the compounds disclosed are 3-aryloxy-3-phenyl-substituted propanamines although they also possess further N-substitution by, for example, $CH_2(CO_2)Et$.

WO 96/09288 describes indole derivatives which are active at the 5 HT receptor. The 5-membered ring portion of the indole moiety is further substituted by one of a number of amine functional groups.

U.S. Pat. No. 4,229,449 discloses variously substituted 2-hydroxy- and 2-methoxy-3-phenoxy-3-phenyl-propanamines which may be used as antidepressant agents.

WO 01/62714 discloses phenylheteroalkylamine derivatives which are inhibitors of nitric oxide synthase. WO 03/011831 and WO 03/011830 discloses heteroarylheteroalkylamine derivatives which are inhibitors of nitric oxide synthase.

WO 02/094262 discloses heteroaryloxy 3-substituted propanamines as serotonin and norepinephrine reuptake inhibitors.

The present invention provides 3-aryloxy/thio-2,3-substituted propanamines which are potent inhibitors of both serotonin and norepinephrine reuptake. Preferred compounds of the present invention exihibit (i) greater potency of inhibition of the serotonin and/or norepinephrine transporters, and/or (ii) improved selectivity of inhibition of the serotonin and/or norepinephrine transporters relative to the dopamine transporter, and/or (iii) improved ADME properties (e.g. reduced tendency to act as a substrate and/or inhibitor for the enzyme Cytochrome P450 2D6), and/or (iv) improved acid stability, as compared to known inhibitors of both serotonin and norepinephrine reuptake.

According to the present invention there is provided a compound of formula I:

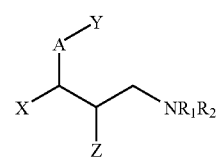

wherein

A is selected from —O— and —S—;

X is selected from phenyl optionally substituted with up to 5 substituents each independently selected from halo, $C_1$-$C_4$ alkyl and $C_1$-$C_4$ alkoxy, thienyl optionally substituted with up to 3 substituents each independently selected from halo and $C_1$-$C_4$ alkyl, and $C_2$-$C_8$ alkyl, $C_2$-$C_8$ alkenyl, $C_3$-$C_8$ cycloalkyl and $C_4$-$C_8$ cycloalkylalkyl, each of which may be optionally substituted with up to 3 substituents each independently selected from halo, $C_1$-$C_4$ alkyl, $C_1$-$C_4$ alkoxy, $C_1$-$C_4$ alkyl-S(O)n- where n is 0, 1 or 2, —$CF_3$, —CN and —$CONH_2$;

Y is selected from phenyl, naphthyl, dihydrobenzothienyl, benzothiazolyl, benzoisothiazolyl, quinolyl, isoquinolyl, naphthyridyl, thienopyridyl, indanyl, 1,3-benzodioxolyl, benzothienyl, indolyl and benzofuranyl, each of which may be optionally substituted with up to 4 or, where possible, up to 5 substituents each independently selected from halo, $C_1$-$C_4$ alkyl, $C_1$-$C_4$ alkoxy, $C_1$-$C_4$ alkyl-$S(O)_n$— where n is 0, 1 or 2, nitro, acetyl, —$CF_3$, $SCF_3$ and cyano; and when Y is indolyl it may be substituted or further substituted by an N-substituent selected from $C_1$-$C_4$ alkyl;

Z is selected from OR$_3$ or F, wherein R$_3$ is selected from H, C$_1$-C$_6$ alkyl and phenyl C$_1$-C$_6$ alkyl;

R$_1$ and R$_2$ are each independently H or C$_1$-C$_4$ alkyl;

and pharmaceutically acceptable salts thereof with the proviso that when Y is optionally substituted phenyl or optionally substituted 1,3-benzodioxolyl and Z is OR$_3$ and X is optionally substituted phenyl then A is —S—.

The compounds of the present invention are potent and selective inhibitors of serotonin and norepinephrine reuptake.

In one group of compounds according to the present invention, A is —O—.

In another group of compounds according to the present invention, A is —S—.

R$_1$ and R$_2$ may both be C$_1$-C$_4$ alkyl, preferably methyl. Preferably, one of R$_1$ and R$_2$ is H. R$_1$ and R$_2$ may both be H. Alternatively, one of R$_1$ and R$_2$ may be H while the other is C$_1$-C$_4$ alkyl, for example C$_1$-C$_3$ alkyl. Preferably, one of R$_1$ and R$_2$ is H and the other is methyl.

It will be appreciated that a compound of formula I will possess at least two chiral centres. Where a structural formula does not specify the stereochemistry at one or more chiral centres, it encompasses all possible stereoisomers and all possible mixtures of stereoisomers (including, but not limited to, racemic mixtures) which may result from stereoisomerism at each of the one or more chiral centers.

In one embodiment of the present invention, the compound possesses the stereochemistry defined in formula II

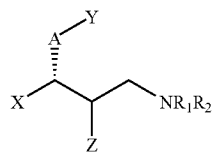

II

In another embodiment of the present invention, the compound possesses the stereochemistry defined in formula III

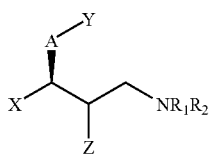

III

In another embodiment of the present invention, the compound possesses the stereochemistry defined in formula IV

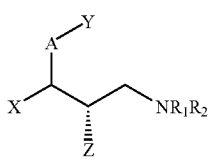

IV

In another embodiment of the present invention, the compound possesses the stereochemistry defined in formula V

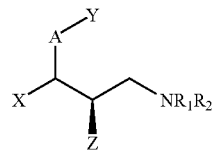

V

In another embodiment of the present invention, the compound possesses the stereochemistry defined in formula VI

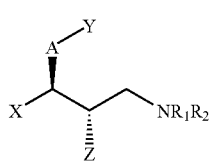

VI

In another embodiment of the present invention, the compound possesses the stereochemistry defined in formula VII

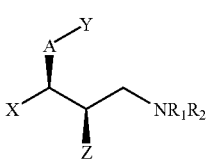

VII

In another embodiment of the present invention, the compound possesses the stereochemistry defined in formula VIII

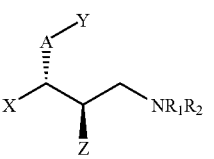

VIII

In another embodiment of the present invention, the compound possesses the stereochemistry defined in formula IX

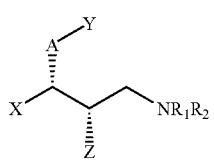

IX

In a particular embodiment of the present invention, Z is F.

In another embodiment of the present invention, Z is OH.

In another embodiment of the present invention, Z is OR$_3$ wherein R$_3$ is selected from C$_1$-C$_6$ alkyl and phenyl C$_1$-C$_6$ alkyl. Preferably Z is OMe or OCH$_2$Ph.

A preferred embodiment of the present invention is that wherein X is unsubstituted phenyl or phenyl which is mono-, di- or tri-substituted with substituents independently selected from halo, C$_1$-C$_4$ alkyl and C$_1$-C$_4$ alkoxy. Halo substituents include F, Cl, Br and I, preferably F or Cl. More preferably, X is unsubstituted phenyl or phenyl which is mono-substituted with fluorine, preferably at the 3-position of the phenyl ring.

In one embodiment of the present invention, Y is phenyl optionally substituted with up to 5 substituents each independently selected from halo, $C_1$-$C_4$ alkyl, $C_1$-$C_4$ alkoxy, $C_1$-$C_4$ alkyl-$S(O)_n$— where n is 0, 1 or 2, nitro, acetyl, —$CF_3$, —$SCF_3$ and cyano. Preferably, Y is unsubstituted phenyl or phenyl which is mono-substituted with chlorine, preferably at the 2-position of the phenyl ring.

In another embodiment of the present invention, Y is naphthyl optionally substituted with up to 5 substituents each independently selected from halo, $C_1$-$C_4$ alkyl, $C_1$-$C_4$ alkoxy, $C_1$-$C_4$ alkyl-$S(O)_n$—where n is 0, 1 or 2, nitro, acetyl, —$CF_3$, —$SCF_3$ and cyano. Preferably, Y is unsubstituted naphthyl or naphthyl which is mono-substituted with fluorine, preferably at the 4-position of the naphthyl ring. In this embodiment the preferred point of attachment of the optionally substituted naphthyl group to the —O— or —S— atom is attachment at the 1 position.

In another embodiment of the present invention, Y is benzofuranyl optionally substituted with up to 5 substituents each independently selected from halo, $C_1$-$C_4$ alkyl, $C_1$-$C_4$ alkoxy, $C_1$-$C_4$ alkyl-$S(O)_n$—where n is 0, 1 or 2, nitro, acetyl, —$CF_3$, —$SCF_3$ and cyano. Preferably, Y is unsubstituted benzofuranyl or benzofuranyl which is mono-substituted with $CH_3$, preferably at the 2-position of the benzofuranyl ring.

In another embodiment of the present invention, Y is benzothienyl optionally substituted with up to 5 substituents each independently selected from halo, $C_1$-$C_4$ alkyl, $C_1$-$C_4$ alkoxy, $C_1$-$C_4$ alkyl-$S(O)_n$—where n is 0, 1 or 2, nitro, acetyl, —$CF_3$, —$SCF_3$ and cyano. Preferably, Y is unsubstituted benzothienyl or benzothienyl which is mono-substituted with fluorine, preferably at the 2-, 5- or 7-position of the benzothienyl ring.

In another embodiment of the present invention, Y is benzoisothiazolyl optionally substituted with up to 4 substituents each independently selected from halo, $C_1$-$C_4$ alkyl, $C_1$-$C_4$ alkoxy, $C_1$-$C_4$ alkyl-$S(O)_n$—where n is 0, 1 or 2, nitro, acetyl, —$CF_3$, —$SCF_3$ and cyano.

When Y is benzofuranyl, benzothienyl or benzoisothiazolyl the preferred point of attachment of the group Y to the —O— or —S— atom is attachment at the 4 or 7 position.

The present invention also provides sub-groups of compounds of formula I or VIII

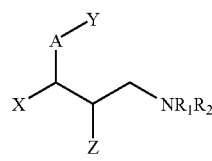

I

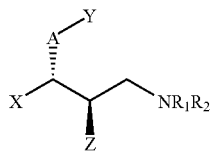

VIII wherein

A is selected from —O— and —S—;

X is selected from phenyl optionally substituted with up to 5 substituents each independently selected from halo, $C_1$-$C_4$ alkyl and $C_1$-$C_4$ alkoxy, thienyl optionally substituted with up to 3 substituents each independently selected from halo and $C_1$-$C_4$ alkyl, and $C_2$-$C_8$ alkyl, $C_2$-$C_8$ alkenyl, $C_3$-$C_8$ cycloalkyl and $C_4$-$C_8$ cycloalkylalkyl, each of which may be optionally substituted with up to 3 substituents each independently selected from halo, $C_1$-$C_4$ alkyl, $C_1$-$C_4$ alkoxy, $C_1$-$C_4$ alkyl-$S(O)_n$— where n is 0, 1 or 2, —$CF_3$, —CN and —$CONH_2$;

Y is selected from naphthyl, dihydrobenzothienyl, benzothiazolyl, benzoisothiazolyl, quinolyl, isoquinolyl, naphthyridyl, thienopyridyl, indanyl, benzothienyl, indolyl and benzofuranyl, each of which may be optionally substituted with up to 4 or, where possible, up to 5 substituents each independently selected from halo, $C_1$-$C_4$ alkyl, $C_1$-$C_4$ alkoxy, $C_1$-$C_4$ alkyl-$S(O)_n$— where n is 0, 1 or 2, nitro, acetyl, —$CF_3$, —$SCF_3$ and cyano; and when Y is indolyl it may be substituted or further substituted by an N-substituent selected from $C_1$-$C_4$ alkyl;

Z is selected from $OR_3$ or F, wherein $R_3$ is selected from H, $C_1$-$C_6$ alkyl and phenyl $C_1$-$C_6$ alkyl;

$R_1$ and $R_2$ are each independently H or $C_1$-$C_4$ alkyl;

and pharmaceutically acceptable salts thereof.

The present invention also provides sub-groups of compounds of formula I or VIII

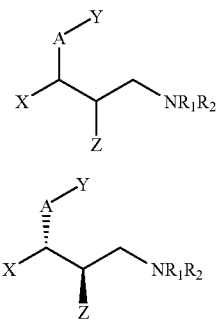

I

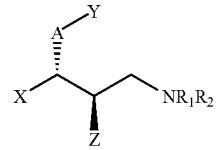

VIII wherein

A is selected from —O— and —S—;

X is selected from phenyl optionally substituted with up to 5 substituents each independently selected from halo, $C_1$-$C_4$ alkyl and $C_1$-$C_4$ alkoxy, and thienyl optionally substituted with up to 3 substituents each independently selected from halo and $C_1$-$C_4$ alkyl;

Y is selected from phenyl, naphthyl, dihydrobenzothienyl, benzothiazolyl, benzoisothiazolyl, quinolyl, isoquinolyl, naphthyridyl, thienopyridyl, indanyl, 1,3-benzodioxolyl, benzothienyl, indolyl and benzofuranyl, each of which may be optionally substituted with up to 4 or, where possible, up to 5 substituents each independently selected from halo, $C_1$-$C_4$ alkyl, $C_1$-$C_4$ alkoxy, $C_1$-$C_4$ alkyl-$S(O)_n$— where n is 0, 1 or 2, nitro, acetyl, —$CF_3$, —$SCF_3$ and cyano; and when Y is indolyl it may be substituted or further substituted by an N-substituent selected from $C_1$-$C_4$ alkyl;

Z is selected from $OR_3$ or F, wherein $R_3$ is selected from H, $C_1$-$C_6$ alkyl and phenyl $C_1$-$C_6$ alkyl;

$R_1$ and $R_2$ are each independently H or $C_1$-$C_4$ alkyl;

and pharmaceutically acceptable salts thereof with the proviso that when Y is optionally substituted phenyl or optionally substituted 1,3-benzodioxolyl and Z is $OR_3$ and X is optionally substituted phenyl then A is —S—.

The present invention also provides sub-groups of compounds of formula I or VIII

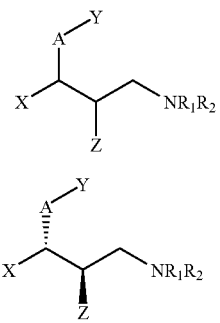

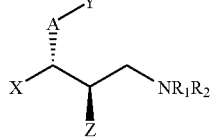

wherein
A is selected from —O— and —S—;
X is selected from phenyl optionally substituted with up to 5 substituents each independently selected from halo, $C_1$-$C_4$ alkyl and $C_1$-$C_4$ alkoxy, and thienyl optionally substituted with up to 3 substituents each independently selected from halo and $C_1$-$C_4$ alkyl;
Y is selected from phenyl, naphthyl, benzothienyl, indolyl and benzofuranyl, each of which may be optionally substituted with up to 5 substituents each independently selected from halo, $C_1$-$C_4$ alkyl, $C_1$-$C_4$ alkoxy, $C_1$-$C_4$ alkyl-S(O)$_n$— where n is 0, 1 or 2, nitro, acetyl, —$CF_3$, —$SCF_3$ and cyano; and when Y is indolyl it may be substituted or further substituted by an N-substituent selected from $C_1$-$C_4$ alkyl;
Z is selected from OH or F;
$R_1$ and $R_2$ are each independently H or $C_1$-$C_4$ alkyl;

and pharmaceutically acceptable salts thereof.

The present invention also provides sub-groups of compounds of formula I or VIII

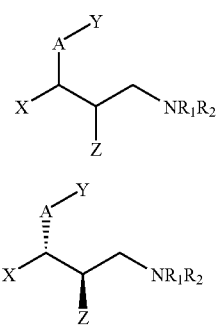

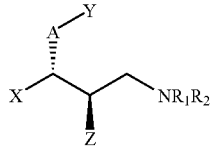

wherein
A is selected from —O— and —S—;
X is selected from phenyl optionally substituted with up to 5 substituents each independently selected from halo, $C_1$-$C_4$ alkyl and $C_1$-$C_4$ alkoxy;
Y is selected from naphthyl, benzothienyl and benzofuranyl, each of which may be optionally substituted with up to 5 substituents each independently selected from halo, $C_1$-$C_4$ alkyl, $C_1$-$C_4$ alkoxy, $C_1$-$C_4$ alkyl-S(O)$_n$— where n is 0, 1 or 2, nitro, acetyl, —$CF_3$, —$SCF_3$ and cyano;
Z is selected from OH or F;
$R_1$ and $R_2$ are each independently H or $C_1$-$C_4$ alkyl;

and pharmaceutically acceptable salts thereof.

The present invention also provides sub-groups of compounds of formula I or VIII

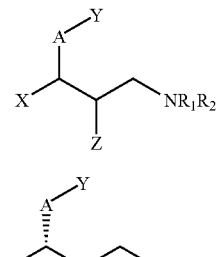

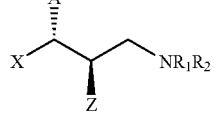

wherein
A is selected from —O— and —S—;
X is selected from phenyl optionally mono-substituted with halo, $C_1$-$C_4$ alkyl or $C_1$-$C_4$ alkoxy;
Y is selected from naphthyl and benzothienyl, each of which may be optionally mono-substituted with halo, $C_1$-$C_4$ alkyl, $C_1$-$C_4$ alkoxy, $C_1$-$C_4$ alkyl-S(O)$_n$— where n is 0, 1 or 2, nitro, acetyl, —$CF_3$, —$SCF_3$ or cyano;
Z is selected from OH or F;
$R_1$ and $R_2$ are each independently H or $C_1$-$C_4$ alkyl;

and pharmaceutically acceptable salts thereof.

The present invention also provides a sub-group of compounds of formula VIII

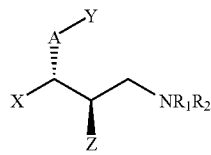

wherein
A is selected from —O— and —S—;
X is selected from phenyl optionally mono-substituted with fluorine;
Y is selected from naphthyl and benzothienyl, each of which may be optionally mono-substituted with fluorine;
Z is OH;
$R_1$ is H;
and $R_2$ is Me;

and pharmaceutically acceptable salts thereof.

In the present specification the term "$C_2$-$C_8$ alkyl" means a monovalent unsubstituted saturated straight-chain or branched-chain hydrocarbon radical having from 2 to 8 carbon atoms.

In the present specification the term "$C_2$-$C_8$ alkenyl" means a monovalent unsubstituted unsaturated straight-chain or branched-chain hydrocarbon radical having from 2 to 8 carbon atoms.

In the present specification the term "$C_3$-$C_8$ cycloalkyl" means a monovalent unsubstituted saturated cyclic hydrocarbon radical having from 3 to 8 carbon atoms.

In the present specification the term "$C_4$-$C_8$ cycloalkylalkyl" means a monovalent unsubstituted saturated cyclic hydrocarbon radical having from 3 to 7 carbon atoms linked to the point of substitution by a divalent unsubstituted saturated straight-chain or branched-chain hydrocarbon radical having from 1 to 5 carbon atoms, the total number of carbon atoms not being greater than 8.

In the present specification the term "phenyl $C_1$-$C_6$ alkyl" means a monovalent phenyl radical linked to the point of substitution by a divalent unsubstituted saturated straight-chain or branched-chain hydrocarbon radical having from 1 to 6 carbon atoms.

In the present specification the term "halo" or "halogen" means F, Cl, Br or I.

In the present specification the term "$C_1$-$C_4$ alkoxy" means a monovalent unsubstituted saturated straight-chain or branched-chain hydrocarbon radical having from 1 to 4 carbon atoms linked to the point of substitution by an O atom.

In the above definitions, similar terms specifying different numbers of C atoms take an analogous meaning.

In the present specification the term "dihydrobenzothienyl" includes 2,3-dihydrobenzothienyl and 1,3-dihydrobenzothienyl. 2,3-dihydrobenzothienyl is preferred.

In the present specification the term "benzoisothiazolyl" includes 1,2-benzoisothiazolyl and 2,1-benzoisothiazolyl. 1,2-benzoisothiazolyl is preferred.

In the present specification the term "naphthyridyl" includes 1,5-, 1,6-, 1,7- and 1,8-naphthyridyl. 1,7-naphthyridyl is preferred.

In the present specification the term "thienopyridyl" includes thieno-[2,3-b]pyridinyl, thieno-[2,3-c]pyridinyl, thieno-[3,2-c]pyridinyl and thieno-[3,2-b]pyridinyl. Thieno-[3,2-b]pyridinyl and thieno-[3,2-c]pyridinyl are preferred.

In the present specification the term "benzothienyl" includes benzo[b]thienyl and benzo[c]thienyl. Benzo[b]thienyl is preferred.

In the present specification the term "benzofuranyl" includes 1-benzofuranyl and isobenzofuranyl. 1-benzofuranyl is preferred.

In the present specification the abbreviation "Ace-Cl" means α-chloroethyl chloroformate.

In the present specification the abbreviation "PS-DIPEA" means polymer-supported diisopropylethylamine.

The present invention also provides a process for producing a compound of formula I above, or a pharmaceutically acceptable salt thereof, which comprises reacting a compound of the formula X:

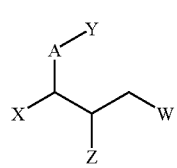

where A, X, Y and Z are as formula I above, and W is a leaving group, with an amine $NR_1R_2$ where $R_1$ and $R_2$ are as formula I above, optionally followed by the step of forming a pharmaceutically acceptable salt. Examples of suitable leaving groups include halo, mesylate and tosylate, but the nature of the leaving group is not critical. The reaction may be carried out in a sealed vessel with a lower alkyl alcohol as solvent.

The present invention also provides a process for producing a compound of formula I above wherein $R_2$ is H, or a pharmaceutically acceptable salt thereof, which comprises deprotecting a compound of the formula XI:

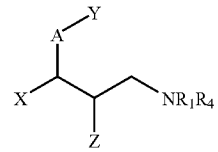

where A, X, Y, Z and $R_1$ are as formula I above, and $R_4$ is a suitable N-protecting group, optionally followed by the step of forming a pharmaceutically acceptable salt. Examples of suitable N-protecting groups will be known to the person skilled in the art and include, for example methyl, benzyl and t-butoxycarbonyl.

The present invention also provides a process for producing a compound of formula I above wherein Z is OH, or a pharmaceutically acceptable salt thereof, which comprises reacting a compound of the formula XII:

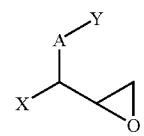

where A, X and Y are as formula I above with an amine $NR_1R_2$ where $R_1$ and $R_2$ are as formula I above, optionally followed by the step of forming a pharmaceutically acceptable salt.

The present invention also provides a process for producing a compound of formula I above wherein $R_1$ and $R_2$ are H, or a pharmaceutically acceptable salt thereof, which comprises reducing a compound of the formula XIII:

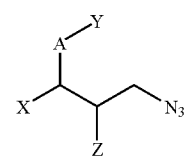

where A, X, Y and Z are as formula I above, optionally followed by the step of forming a pharmaceutically acceptable salt. Examples of suitable reducing agents will be known to the person skilled in the art.

The present invention also provides a process for producing a compound of formula I above wherein $R_1$ and $R_2$ are $C_1$-$C_4$ alkyl, or a pharmaceutically acceptable salt thereof, which comprises N-protecting a compound of the formula XIV by the introduction of two $C_1$-$C_4$ alkyl groups:

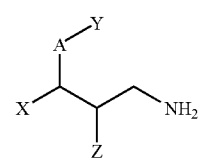

where A, X, Y and Z are as formula I above, optionally followed by the step of forming a pharmaceutically acceptable salt. Examples of suitable reagents for effecting N-protection by two $C_1$-$C_4$ alkyl groups will be known to the person skilled in the art.

Compounds of the present invention are selective inhibitors of the reuptake of both serotonin and norepinephrine and as such are useful as pharmaceuticals. They are particularly useful for the treatment of pain.

For clinical purposes, pain may be divided into two categories: acute pain and persistent pain. Acute pain is provoked by noxious stimulation produced by injury and/or disease of skin, deep somatic structures or viscera, or abnormal function of muscle or viscera that does not produce actual tissue damage. On the other hand, persistent pain can be defined as pain that persists beyond the usual course of an acute disease or a reasonable time for an injury to heal or that is associated with a chronic pathologic process that causes continuous pain or the pain recurs at intervals for months or years. If pain is still present after a cure should have been achieved, it is considered persistent pain. For the purpose of the present invention, persistent pain can be chronic non-remitting or recurrent. The difference in definition between acute and persistent pain is not merely semantic but has an important clinical relevance. For example, a simple fracture of the wrist usually remains painful for a week to 10 days. If the pain is still present beyond the typical course of treatment, it is likely that the patient is developing reflex sympathetic dystrophy, a persistent pain syndrome that requires immediate effective therapy. Early and effective intervention potentially prevents the undue disability and suffering, and avoids the potential development of a condition that becomes refractory to therapy.

Acute and chronic pain differ in etiology, mechanisms, pathophysiology, symptomatology, diagnosis, therapy, and physiological responses. In contrast to the transitory nature of acute pain, persistent pain is caused by chronic pathologic processes in somatic structures or viscera, by prolonged and sometimes permanent dysfunction of the peripheral or central nervous system, or both. Also, persistent pain can sometimes be attributed to psychologic mechanisms and/or environmental factors.

Current therapies for persistent pain include opiates, barbiturate-like drugs such as thiopental sodium and surgical procedures such as neurectomy, rhizotomy, cordotomy, and cordectomy.

The compounds of the present invention are indicated in the treatment of persistent pain and references herein to pain are intended to refer to persistent pain.

In addition to the compounds of formula I and processes for the preparation of said compounds, the present invention further provides pharmaceutical compositions comprising a compound of formula I or a pharmaceutically acceptable salt thereof, together with a pharmaceutically acceptable diluent or carrier.

Further, the present invention provides a compound of formula I or a pharmaceutically acceptable salt thereof, for use as a pharmaceutical; and a compound of formula I or a pharmaceutically acceptable salt thereof, for use as a selective inhibitor of the reuptake of both serotonin and norepinephrine.

The present compounds and salts may be indicated in the treatment of disorders associated with serotonin and norepinephrine dysfunction in mammals.

The term "serotonin and norepinephrine dysfunction" as used herein refers to a reduction in the amount of serotonin and norepinephrine neurotransmitters within the synaptic cleft below that which would be considered to be normal or desirable for a species, or an individual within that species. Thus the phrase "disorders associated with serotonin and norepinephrine dysfunction in mammals" refers to disorders which are associated with a reduction in the amount of serotonin and norepinephrine neurotransmitters within the synaptic cleft below that which would be considered to be normal or desirable for the mammalian species, or an individual within the species, in question. Some examples of disorders currently believed to be associated with reduced levels of serotonin and norepinephrine within the synaptic cleft include depression, OCD, anxiety, memory loss, urinary incontinence (including stress urinary incontinence and urge incontinence), conduct disorders, attention-deficit disorder (including ADHD), obesity, hot flushes/flashes, pain (including inflammatory pain, neuropathic pain, non-neuropathic non-inflammatory pain, persistent pain, persistent pain of inflammatory and/or neuropathic origin, headache and migraine), eating disorders (including bulimia and anorexia nervosa), inflammatory bowel disorders, functional bowel disorders, dyspepsia, chron's disease, iletis, ischemic bowel disease, ulcerative colitis, gastroesophageal reflux for functional bowel disorders, irritable bowel syndrome, insterstitial cystitis, urethral syndrome, gastric motility disorders, substance abuse (including alcoholism, tobacco abuse, smoking cessation, symptoms caused by withdrawal or partial withdrawal from the use of tobacco or nicotine and drug addiction including cocaine abuse), dementia of ageing, senile dementia, Alzheimer's, Parkinsonism, social phobia, disruptive behavior disorders, impulsive control disorders, borderline personality disorder, chronic fatigue syndrome, panic disorders, post-traumatic stress disorder, schizophrenia, gastrointestinal disorders, cardiovascular disorders, emesis, sleep disorders, cognitive disorders, psychotic disorders, brain trauma, premenstrual syndrome or late luteal syndrome, sexual dysfunction (including premature ejaculation and erectile difficulty), autism, mutism and trichotilomania. The compounds of the present invention are particularly suitable for the treatment of pain.

The compounds of the present invention are also indicated for the treatment of disorders which are ameliorated by an increase in the amount of serotonin and norepinephrine neurotransmitters within the synaptic cleft of a mammal above that which would be considered to be normal or desirable for the mammalian species, or an individual within the species, in question.

The term "treatment" as used herein refers to both curative and prophylactic treatment of disorders associated with norepinephrine dysfunction.

The present invention also provides the use of a compound of formula I, or a pharmaceutically acceptable salt thereof, in the manufacture of a medicament for selectively inhibiting the reuptake of serotonin and norepinephrine; the use of a compound of formula I, or a pharmaceutically acceptable salt thereof, in the manufacture of a medicament for the treatment of disorders associated with serotonin and norepinephrine dysfunction in mammals; the use of a compound of formula I, or a pharmaceutically acceptable salt thereof, in the manufacture of a medicament for the treatment of a disorder selected from those listed above and in particular selected from depression, OCD, anxiety, memory loss, urinary incontinence, conduct disorders, ADHD, obesity, alcoholism, smoking cessation, hot flushes/flashes and pain; and the use of a compound of formula I, or a pharmaceutically acceptable salt thereof, in the manufacture of a medicament for the treatment of a disorder selected from depression, urinary incontinence, particularly stress induced urinary incontinence, and more especially, pain. The present invention further provides a compound of formula I for treating disorders associated with serotonin and norepinephrine dysfunction in mammals, for example a disorder selected from those listed above and in particular selected from depression, OCD, anxiety, memory loss, urinary incontinence, conduct disorders, ADHD, obesity, alcoholism, smoking cessation, hot flushes/ flashes and pain, especially depression, urinary incontinence, particularly stress induced urinary incontinence, and, more especially, pain.

Further the present invention provides a method for selectively inhibiting the reuptake of serotonin and norepinephrine in mammals, comprising administering to a patient in need thereof an effective amount of a compound of formula I or a pharmaceutically acceptable salt thereof; a method for treating disorders associated with serotonin and norepinephrine dysfunction in mammals, comprising administering to a patient in need thereof an effective amount of a compound of formula I or a pharmaceutically acceptable salt thereof; and a method for treating a disorder selected from those listed above and in particular selected from depression, OCD, anxiety, memory loss, urinary incontinence, conduct disorders, ADHD, obesity, alcoholism, smoking cessation, hot flushes/flashes and pain, comprising administering to a patient in need thereof an effective amount of a compound of formula I or a pharmaceutically acceptable salt thereof.

The present invention includes the pharmaceutically acceptable salts of the compounds of formula I. Suitable salts include acid addition salts, including salts formed with inorganic acids, for example hydrochloric, hydrobromic, nitric, sulphuric or phosphoric acids, or with organic acids, such as organic carboxylic acids, for example pyruvic, lactobionic, glycolic, oxalic, maleic, hydroxymaleic, fumaric, malic, tartaric, citric, salicylic, o-acetoxybenzoic, or organic sulphonic, 2-hydroxyethane sulphonic, toluene-p-sulphonic, bisethanesulphonic acid or methanesulphonic acid.

In addition to the pharmaceutically acceptable salts, other salts are included in the invention. They may serve as intermediates in the purification of compounds or in the preparation of other, for example pharmaceutically acceptable, acid addition salts, or are useful for identification, characterisation or purification.

While all the compounds of the present invention are believed to inhibit the reuptake of serotonin and norepinephrine in mammals there are certain of these compounds which are preferred for such uses. Preferred identities for X, Y, Z, A, $R_1$ and $R_2$ and substituents for each have been set out above.

Compounds of the present invention may be prepared by conventional organic chemistry techniques.

The "anti" chain hydroxylated propanamines may be prepared using the methodology outlined below. Although X is shown as optionally substituted phenyl in the reaction schemes below, the same methodology could be applied for other identities of X (except thienyl).

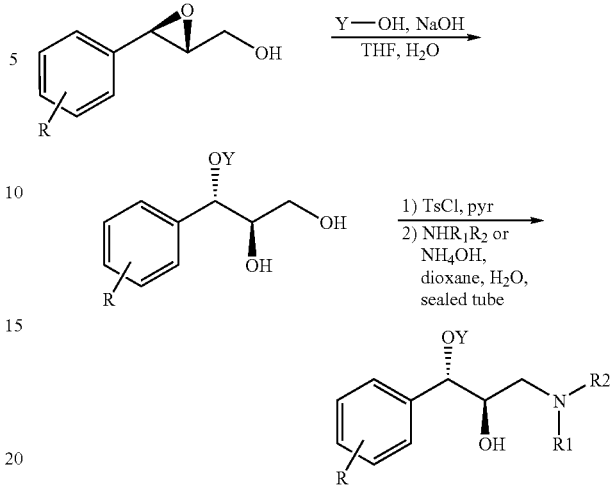

The "syn" chain hydroxylated propanamines may be prepared using the method outlined below (conversion of (I) to (II) is further described in *Tetrahedron Lett.* 1986, 41, 4987). Although X is shown as phenyl in the reaction schemes below, the same methodology could be applied for other identities of X (except thienyl).

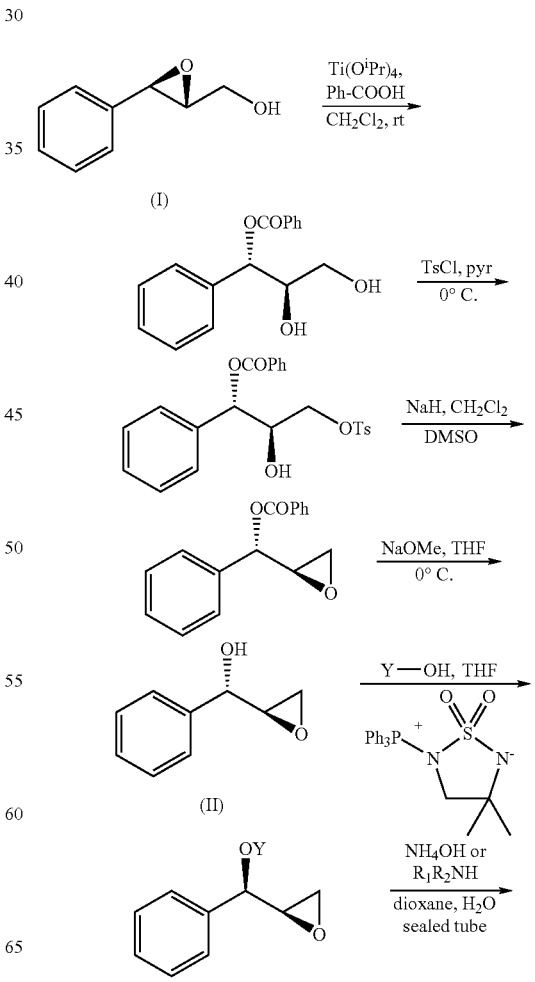

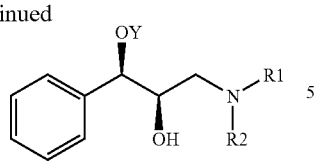

Alternatively, the "syn" chain hydroxylated propanamines may be prepared using the method outlined below.

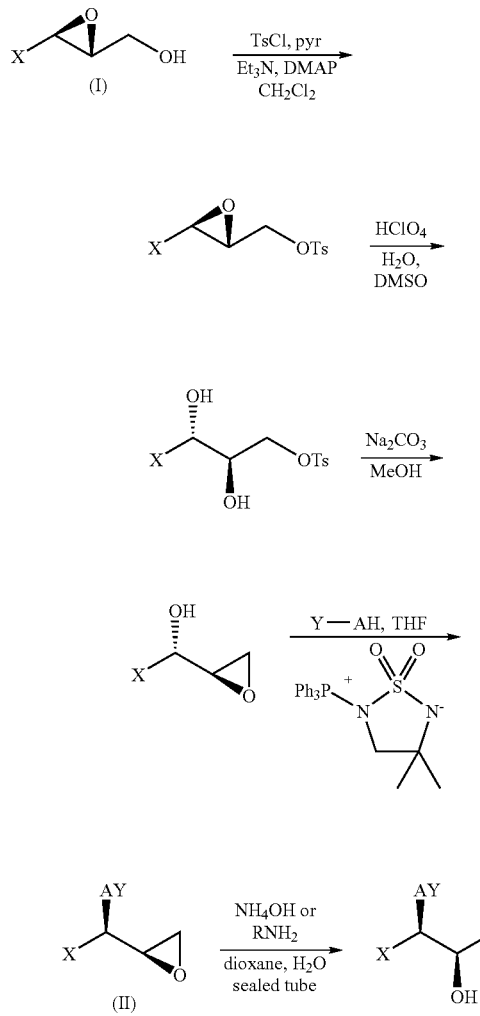

Alternatively, the "syn" and "anti" chain hydroxylated propanamines may be prepared using the intermediates shown below.

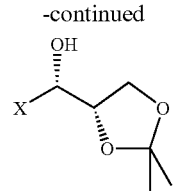

The same chemical transformations may be applied to each intermediate to obtain each of the four stereochemically distinct final products. For example:

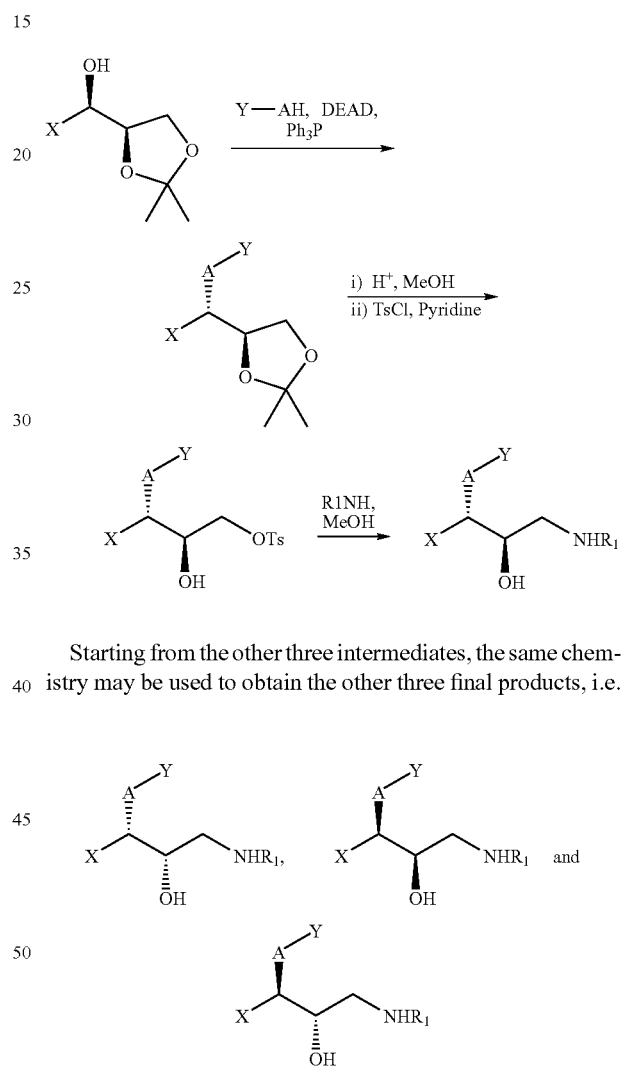

Starting from the other three intermediates, the same chemistry may be used to obtain the other three final products, i.e.

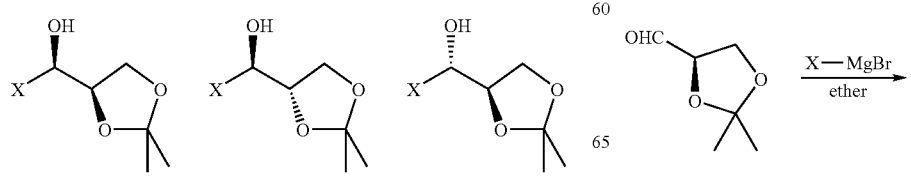

The four intermediates may be synthesized by two different routes. The first route is shown below:

-continued

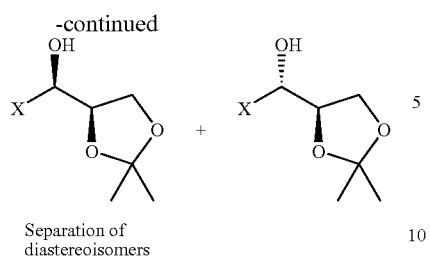

Separation of diastereoisomers

The other two intermediates may be obtained using the same chemistry but starting with the compound:

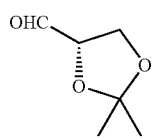

The second route is shown below:

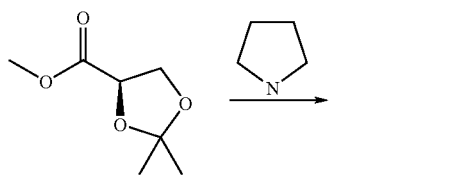

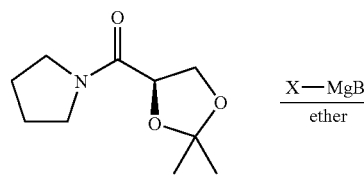

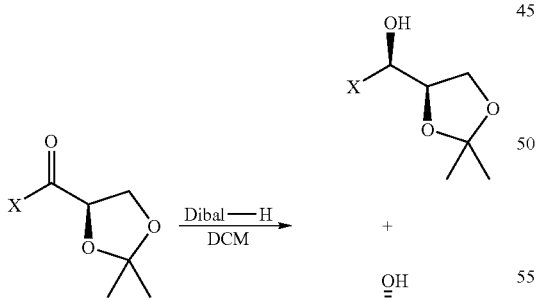

Separation of diastereoisomers

The other two intermediates may be obtained using the same chemistry but starting with the compound:

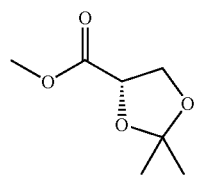

The preparation of the reagent 4,4-(dimethyl-1,1-dioxido-1,2,5-thiadiazolidin-2-yl)-triphenyl phosphonium is described in J. Org. Chem. 1994, 59, 2289.

The "syn" chain fluorinated propanamines may be prepared using the method outlined below. Although X is shown as optionally substituted phenyl in the reaction schemes below, the same methodology could be applied for other identities of X (except thienyl).

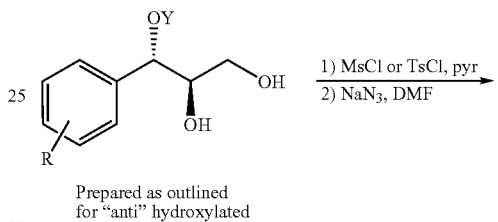

Prepared as outlined for "anti" hydroxylated propanamines

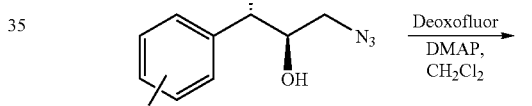

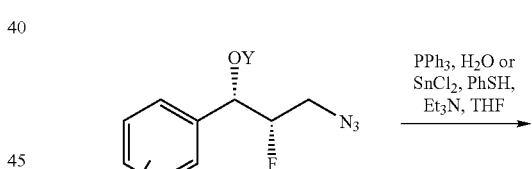

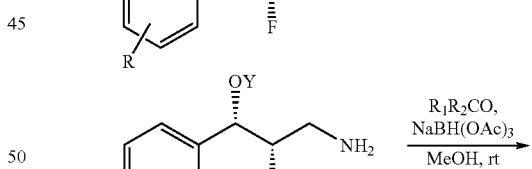

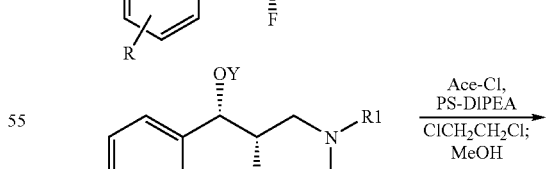

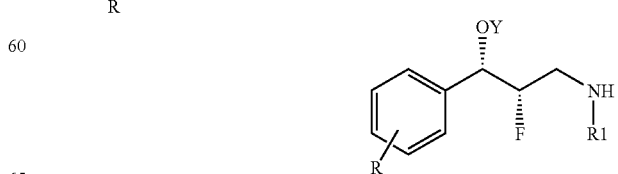

The "anti" chain fluorinated propanamines may be prepared using the method outlined below. Although X is shown as optionally substituted phenyl in the reaction schemes below, the same methodology could be applied for other identities of X (except thienyl).

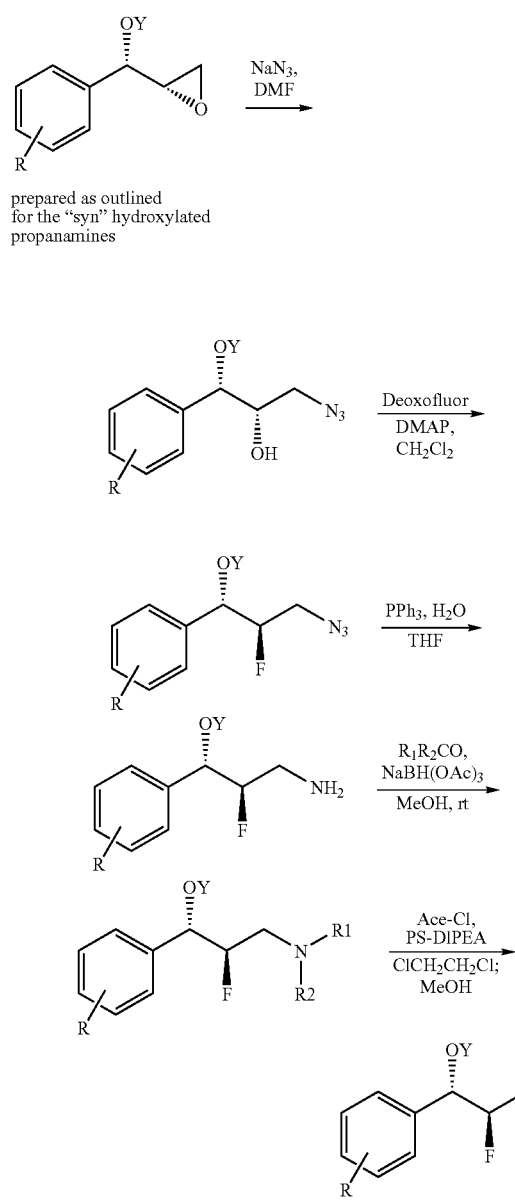

When X is thienyl, the hydroxylated propanamines may be prepared using the methodology outlined below.

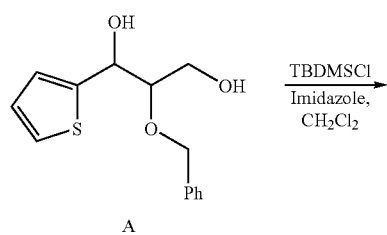

The synthesis of A is described in the reference S. Kobayashi, I. Hachiya, M. Yasuda; Tetrahedron Letters, 1996, 37(31), 5569-5572. The mixture of stereoisomers obtained by this route is firstly separated by achiral chromatography to give a mixture of chiral diasteroisomers, then by chiral chromatography to separate the mixture of chiral diasteroisomeric isomers into individual chiral final products.

When X is thienyl, the fluorinated propanamines may be prepared using the methodology outlined below.

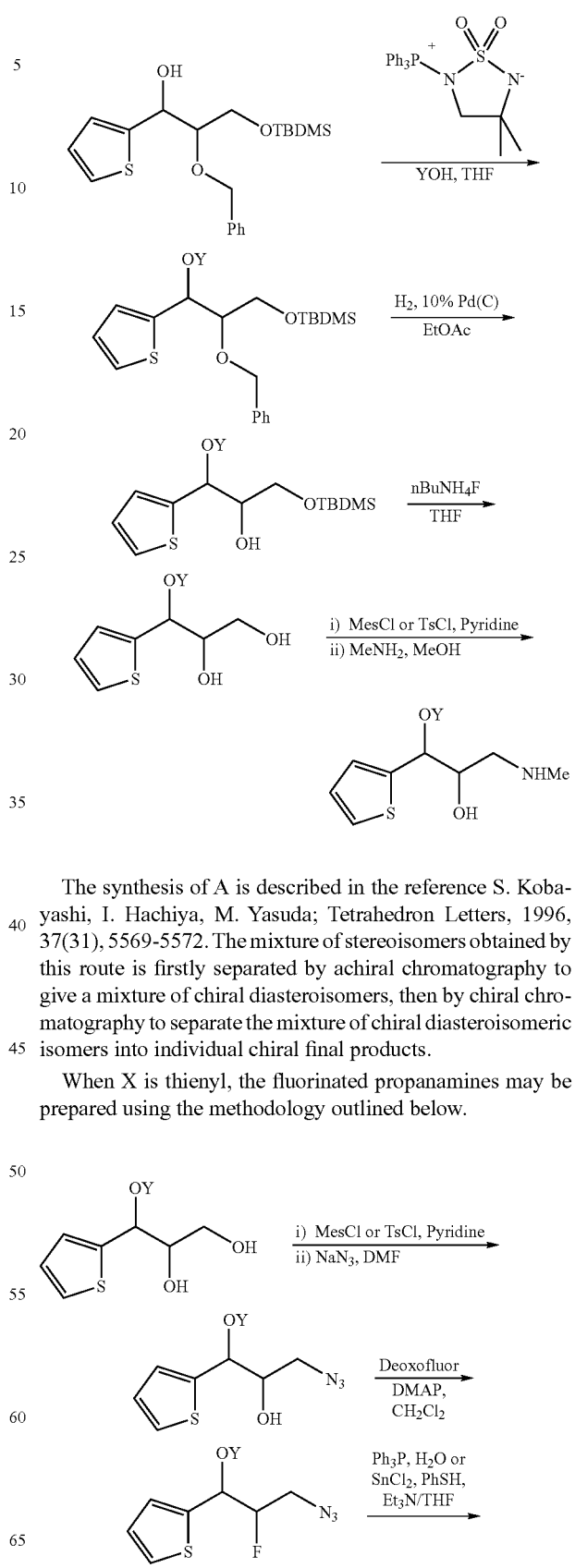

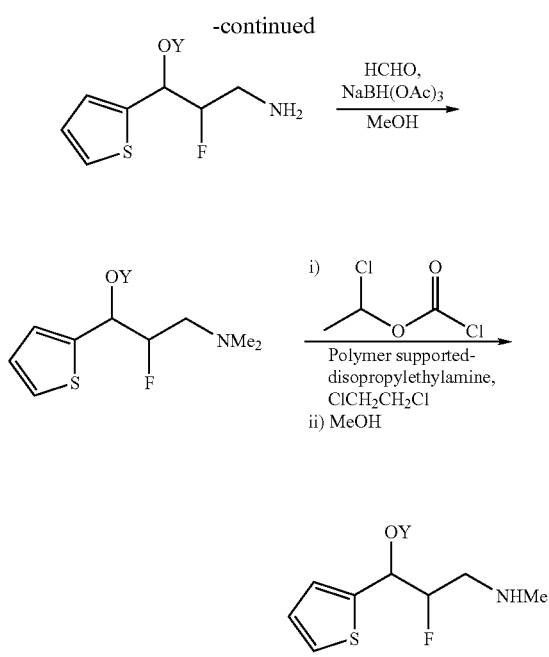

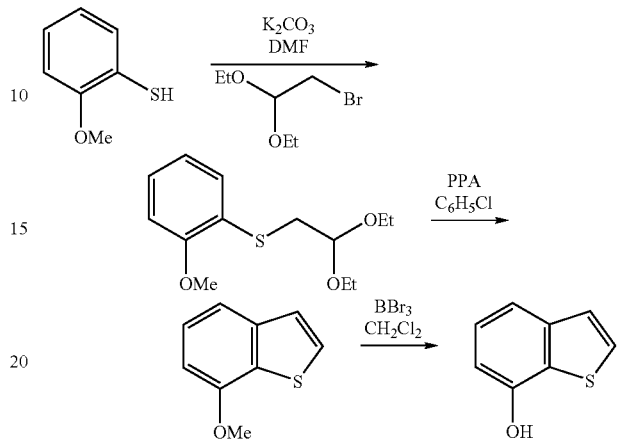

The starting material is synthesised as shown in the previous scheme. The mixture of stereoisomers obtained by this route is firstly separated by achiral chromatography to give a mixture of chiral diastereoisomers, then by chiral chromatography to separate the mixture of chiral diastereoisomeric isomers into individual chiral final products.

Use of Y—SH in place of Y—OH in the above methodologies provides compounds wherein A is S. Note however that for converting hydroxy to aryl sulfide it is preferred to react the propanol species with Y—SH, (cyanomethyl)trimethylphosphonium iodide (Tetrahedron, 2001, 57, 5451-5454) and diisopropylamine in propionitrile.

The benzothiophenes of the invention have been made by several routes. Thus a preferred route is by the alkylation of a thiophenol derivative with bromoacetaldehyde diethyl acetal followed by subsequent acid catalysed cyclisation with polyphosphoric acid in chlorobenzene with elimination of ethanol. Subsequent demethylation provided the hydroxybenzothiophene needed for subsequent ether formation.

Analogous cyclisation of phenylthioacetone derivatives with PPA can be used to synthesise 3-methyl derivatives of benzothiophene methyl ethers.

A further preferred route to substituted benzothiophenes is an iodine catalysed cyclisation of a mercaptopropenoic acid. Thus a benzaldehyde can be condensed with rhodanine and subsequently hydrolysed under basic conditions to a mercaptopropenoic acid. The resultant mercaptopropenoic acid can be cyclised using iodine and then decarboxylated with diazobicycloundecane in dimethylacetamide. Finally boron tribromide in dichloromethane may be used to demethylate the methyl ether to provide the hydroxybenzothiophene.

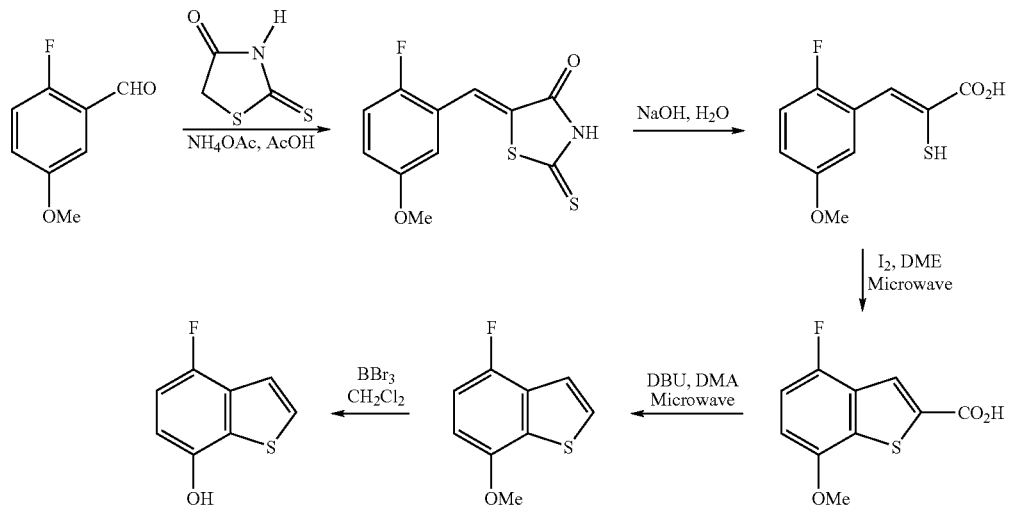

Methods for the synthesis of other Y—AH precursors of use in the present invention (or literature references describing their synthesis) are provided in the experimental section below.

The following Examples further illustrate the compounds of the present invention and methods for their synthesis.

In the following section, there is described the synthesis of precursors and common intermediates for the compounds of the present invention.

4-Fluoro-2-methoxybenzenethiol a) 2-Bromo-5-fluoroanisole

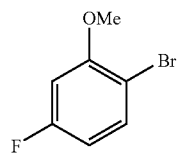

To a suspension of 2-bromo-5-fluorophenol (20.0 g, 104.7 mmol) and potassium carbonate (21.71 g, 157.1 mmol) in acetone (200 mL) was added dimethyl sulphate (10.90 mL, 115.2 mmol). The resulting suspension was allowed to stir at 60° C. for 2 h before being allowed to cool and then concentrated in vacuo. The residue was dissolved in ether (200 mL) and water (100 mL). The organic phase was washed with aqueous hydrochloric acid (2 N, 50 mL), saturated sodium bicarbonate solution (50 mL) with the resulting organic phase being dried (MgSO$_4$) and the solvent evaporated in vacuo to give a pale yellow oil (21.46 g, 100%). $\delta_H$ (300 MHz, CDCl$_3$) 7.45 (1H, dd, Ar), 6.70-6.55 (2H, m, Ar), 3.90 (3H, s, OCH$_3$).

b) 4-Fluoro-2-methoxybenzenethiol

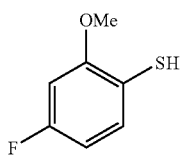

To a suspension of 2-bromo-5-fluoroanisole (2.00 g, 9.755 mmol) and elemental sulphur (0.468 g, 14.632 mmol) in dry THF (50 mL) was slowly added tert-butyl lithium in pentane (1.7 M, 12.6 mL, 21.46 mmol) at −78° C. The resulting suspension was allowed to stir at −78° C. for 60 mins before being poured onto saturated ammonium chloride solution (80 mL) and product extracted with diethyl ether (100 mL). The organic phase was washed with aqueous hydrochloric acid (2 N, 40 mL), with the resulting organic phase being dried (MgSO$_4$) and the solvent evaporated in vacuo to give a pale yellow oil. This was treated to a pad of silica gel, eluting with hexane:ethyl acetate [95:5] to give a pale yellow oil (1.50 g, 68%). $\delta_H$ (300 MHz, CDCl$_3$) 7.20 (1H, dd, Ar), 6.65-6.55 (2H, d, Ar), 3.90 (3H, s, OCH$_3$), 3.68 (1H, s, SH).

Similarly prepared was
3-Methoxy-5-trifluoromethylbenzenethiol as a pale yellow oil (14.473 g, 100%). $\delta_H$ (300 MHz, CDCl$_3$) 7.40-6.90 (3H, m, Ar), 3.87 (1H, s, SH), 3.80 (3H, s, OCH$_3$).

3-Fluoro-2-methoxybenzaldehyde

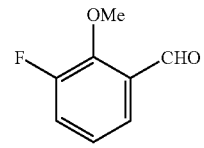

To a suspension of 3-fluoro-2-hydroxybenzaldehyde (5.328 g, 38.02 mmol) and potassium carbonate (7.88 g, 57.03 mmol) in acetone (60 mL) was added dimethyl sulphate (3.96 mL, 41.83 mmol). The resulting suspension was stirred at 60° C. for 2 h before being allowed to cool and then concentrated in vacuo. The residue was dissolved in dichloromethane (100 mL) and water (50 mL). The organic phase was washed with saturated sodium bicarbonate (50 mL) with the resulting organic phase being dried (MgSO$_4$) and the solvent evaporated in vacuo to give a pale yellow oil (6.262 g, 38.02 mmol, 100%). $\delta_H$ (300 MHz, CDCl$_3$) 10.40 (1H, s, CHO), 7.60 (1H, d, Ar), 7.30 (1H, m, Ar), 7.10 (1H, m, Ar), 4.10 (3H, s, OCH$_3$).

5-Methoxy-2-methylbenzaldehyde a) 4-Bromo-3-(1,3-dioxolan-2-yl)phenyl methyl ether

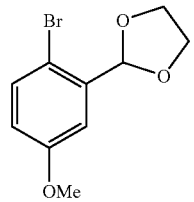

A solution of 2-bromo-5-methoxybenzaldehyde (10.00 g, 46.5 mmol) in toluene (600 mL), ethanediol (3.88 mL, 69.8 mmol) and para-toluene sulphonic acid (50 mg) were heated under Dean-Stark conditions for 24 h. After this time the reaction was allowed to cool to room temperature before being washed with saturated aqueous sodium hydrogen carbonate (2×150 mL). The organic phase was dried (MgSO$_4$) and the solvent removed in vacuo to give a colourless oil (12.6 g, 100%); R$_f$=0.23 in hexane:ethyl acetate [10:1]; $\delta_H$ (300 MHz, CDCl$_3$) 7.42 (1H, d, Ar), 7.25 (1H, d, Ar), 6.75 (1H, dd, Ar), 6.03 (1H, s, CHO), 4.20-4.01 (4H, m, 2×CH$_2$), 3.80 (3H, s, OCH$_3$).

b) 3-(1,3-Dioxolan-2-yl)-4-methylphenyl methyl ether

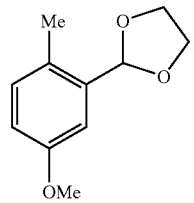

n-Butyl lithium in hexane (17.07 mL, 1.42 M, 25.1 mmol) was added dropwise at −78° C. to a stirred solution of 4-bromo-3-(1,3-dioxolan-2-yl)phenyl methyl ether (5.00 g, 19.3 mmol) in dry THF (60 mL). The resulting solution was allowed to stir at −78° C. for 30 mins before being quenched with iodomethane (2.40 mL, 38.6 mmol). The resulting solution was stirred at −78° C. for a further 20 mins before being quenched with saturated aqueous ammonium chloride solution (60 mL). The organic phase was dried (MgSO$_4$) and the solvent evaporated in vacuo. The residue was purified by flash chromatography eluting silica gel with hexane:ethyl acetate [10:1] to give a pale yellow oil (3.07 g, 82%); R$_f$=0.40 in hexane:ethyl acetate [10:1]; δ$_H$ (300 MHz, CDCl$_3$) 7.20-6.99 (2H, m, Ar), 6.75 (1H, dd, Ar), 5.92 (1H, s, CH), 4.20-4.01 (4H, m, 2×CH$_2$), 3.80 (3H, s, OCH$_3$), 2.32 (3H, s, CH$_3$).

c) 5-Methoxy-2-methylbenzaldehyde

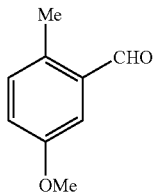

A solution of 2-(2-methyl-5-methoxyphenyl)-1,3-dioxalone (7.28 g, 37.5 mmol) in THF (1200 mL) and HCl (5%, 50 mL) was stirred at room temperature for 48 h. After this time the reaction was diluted with diethyl ether (100 mL) and washed with brine. The organic phase was dried (MgSO$_4$) and the solvent evaporated in vacuo. The residue was purified by flash chromatography eluting silica gel with hexane:ethyl acetate [95:5] to give a pale yellow oil (4.93 g, 88%); R$_f$=0.31 in hexane:ethyl acetate [10:1]; δ$_H$ (300 MHz, CDCl$_3$) 10.28 (1H, s, CHO), 7.35-6.99 (3H, m, Ar), 3.82 (3H, s, OCH$_3$), 2.62 (3H, s, CH$_3$).

1-[(5-Fluoro-2-methoxyphenyl)thio]acetone

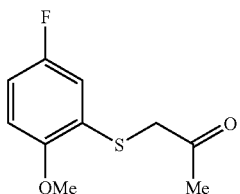

tert-Butyl lithium in pentane (6.30 mL, 10.7 mmol) was added dropwise at −78° C. over 35 mins to a stirred suspension of 2-bromo-4-fluoroanisole (1.00 g, 4.87 mmol) and elemental sulfur (234 mg, 7.31 mmol) in dry THF (10 mL). The resulting yellow solution was stirred and −78° C. for 15 mins before chloroacetone (894 mg, 9.74 mmol) was added. The resulting solution was allowed to stir at −78° C. for 1 hr before being quenched with NH$_4$Cl (sat., 20 mL). The organic phase was extracted and dried (MgSO$_4$) and the solvent removed in vacuo. The residue was purified by flash chromatography eluting silica gel with hexane:ethyl acetate [4:1] to yield a colourless oil (1.03 g, 98%) which slowly solidified on standing; R$_f$=0.34 in hexane:ethyl acetate [4:1]; δ$_H$ (300 MHz, CDCl$_3$) 7.08-6.98 (1H, dd, Ar), 6.95-6.82 (1H, m, Ar), 6.80-6.71 (1H, dd, Ar), 3.91 (3H, s, OCH$_3$), 3.75 (2H, s, CH$_2$), 2.30 (3H, s, CH$_3$).

1-[(2-Fluoro-5-methoxyphenyl)thio]acetone

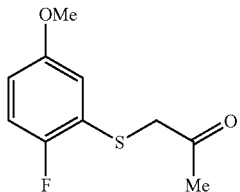

To a solution of 2,2,6,6-tetramethylpiperidine (8.03 mL, 47.6 mmol) in THF (20 mL) at −78° C. was added a solution of 2.5 M n-butyllithium in hexanes (19.04 mL, 47.6 mmol). After stirring for 30 minutes at −78° C. a solution of 4-fluoroanisole (5 g, 39.7 mmol) in THF (10 mL) was added dropwise. After a further 30 minutes elemental sulphur (1.78 g, 55.5 mmol) was added and stirred until almost all of the sulphur has disappeared. Chloroacetone (3.79 mL, 47.6 mmol) was then added and the solution warmed to room temperature over 2 hours. The reaction was quenched by pouring into saturated ammonium chloride (50 mL) and extraction with diethyl ether (2×50 mL). The combined organic extracts were dried (MgSO$_4$) and the solvent removed in vacuo to give a brown oil which was purified by flash chromatography with a gradient of 0-5% diethyl ether in hexane to give the title compound (1.96 g, 23%); δ$_H$ (300 MHz, CDCl$_3$) 7.02-6.86 (2H, m, ArH), 6.80-6.71 (1H, m, ArH), 3.78 (3H, s, OCH$_3$), 3.68 (2H, s, CH$_2$) and 2.29 (3H, s, CH$_3$).

1-Benzothien-7-yl methyl ether a) 1-[(2,2-Diethoxyethyl)thio]-2-methoxybenzene

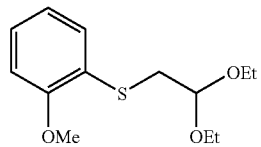

To a suspension of 2-methoxybenzenethiol (10 g, 71.4 mmol) and potassium carbonate (20 g, 143 mmol) in dry N,N-dimethylformamide (100 mL) was added dropwise over 20 mins a solution of bromoacetaldehyde diethyl acetal (10.3 mL, 71.4 mmol) in dry N,N-dimethylformamide (50 mL). The resulting suspension was allowed to stir at room temperature for 45 mins before being diluted with water (500 mL) and extracted with hexane (200 mL). The organic phase was further extracted with brine (4×100 mL), with the resulting organic phase being dried (MgSO$_4$) and the solvent removed in vacuo to give a pale yellow oil (18.6 g) which was ca 95% pure. This material was further purified by flash chromatography eluting silica gel with hexane:ether [10:1] to give a colourless oil (18 g, 98%). δ$_H$ (300 MHz, CDCl$_3$) 7.34 (1H, d, Ar), 7.2 (1H, m, Ar), 6.92-6.80 (2H, m, Ar), 4.62 (1H, t, J=7 Hz, CH(OEt)$_2$), 3.85 (3H, s, OCH$_3$), 3.70-3.42 (4H, m, OCH$_2$CH$_3$), 3.10 (2H, d, J=7 Hz, SCH$_2$), 1.12 (6H, t, J=7 Hz, OCH$_2$CH$_3$).

Similarly prepared were

1-[(2,2-Diethoxyethyl)thio]4-fluoro-2-methoxybenzene as a colourless oil (0.828 g, 3.018 mmol, 46%). $\delta_H$ (300 MHz, CDCl$_3$) 7.38 (1H, dd, Ar), 6.90 (2H, m, Ar), 4.62 (1H, t, J=7 Hz, CH(OEt)$_2$), 3.85 (3H, s, OCH$_3$), 3.70-3.45 (4H, m, OCH$_2$CH$_3$), 3.00 (2H, d, J=7 Hz, SCH$_2$), 1.18 (6H, t, J=7 Hz, OCH$_2$CH$_3$).

1-[(2,2-Diethoxyethyl)thio]-3-methoxy-5-trifluoromethylbenzene as a pale orange oil (6.87 g, 21.18 mmol, 34%). $\delta_H$ (300 MHz, CDCl$_3$) 7.20 (1H, s, Ar), 7.00 (1H, s, Ar), 6.90 (1H, s, Ar), 4.65 (1H, t, J=7 Hz, CH(OEt)$_2$), 3.80 (3H, s, OCH$_3$), 3.70-3.50 (4H, m, OCH$_2$CH$_3$), 3.15 (2H, d, J=7 Hz, SCH$_2$), 1.20 (6H, t, J=7 Hz, OCH$_2$CH$_3$).

b) 1-Benzothien-7-yl methyl ether

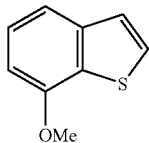

A solution of 1-[(2,2-diethoxyethyl)thio]-2-methoxybenzene (18 g, 70.3 mmol) in dry chlorobenzene (100 mL) was added slowly to a stirred solution of polyphosphoric acid (50 g) in dry chlorobenzene (300 mL) at 145° C. After addition was complete the resulting black solution was stirred at 155° C. for a further 18 hrs. After this time the reaction was allowed to cool to room temperature before being filtered through a pad of CELITE™, the solid cake was washed with dichloromethane (200 mL) and the combined organic extracts were concentrated in vacuo. The residue was purified by flash chromatography eluting silica gel with hexane:ethyl acetate [95:5] to give a pale yellow oil (8.7 g, 75%); $\delta_H$ (300 MHz, CDCl$_3$) 7.45-7.29 (4H, m, Ar), 6.75 (1H, d, Ar), 4.00 (3H, s, OCH$_3$).

Similarly prepared were

5-Fluoro-1-benzothien-7-yl methyl ether as a pale yellow oil (0.132 g, 0.724 mmol, 24%); $\delta_H$ (300 MHz, CDCl$_3$) 7.50 (1H, d, Ar), 7.28 (1H, d, Ar), 7.10 (1H, d, Ar), 6.58 (1H, d, Ar), 4.00 (3H, s, OCH$_3$).

4-Trifluoromethyl-1-benzothien-6-yl methyl ether as a yellow oil (2.832 g, 12.19 mmol, 58%); $\delta_H$ (300 MHz, CDCl$_3$) 7.50-7.35 (3H, m, Ar), 7.28 (1H, s, Ar), 3.90 (3H, s, OCH$_3$).

4-Fluoro-7-methoxy-1-benzothiophene a) 5-(2-Fluoro-5-methoxybenzylidene)-2-thioxo-1,3-thiazolidin-4-one

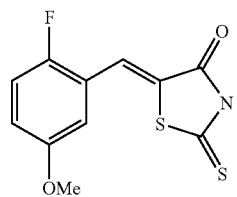

To a suspension of 2-fluoro-5-methoxybenzaldehyde (5.00 g, 32.46 mmol) and rhodanine (4.31 g, 32.46 mmol) in dry toluene (1000 mL) was added ammonium acetate (50 mg) and acetic acid (2 mL). The resulting suspension was allowed to stir at 120° C. for 12 h under Dean-Stark apparatus before being allowed to cool and filtered. Resultant solid was washed with hexane and allowed to dry in vacuo to give an orange crystalline solid (8.00 g, 91%); $\delta_H$ (300 MHz, CDCl$_3$) 7.50 (1H, s, CH=C); 7.31 (1H, t, Ar), 7.20-7.11 (1H, m, Ar), 6.95-6.89 (1H, m, Ar), 3.80 (3H, s, OCH$_3$).

Similarly prepared were 5-(3-Fluoro-2-methoxybenzylidene)-2-thioxo-1,3-thiazolidin-4-one as an orange solid (7.942 g, 78%). $\delta_H$ (300 MHz, CDCl$_3$) 7.82 (1H, s, ArCHCR$_2$), 7.30-7.10 (3H, m, Ar), 4.05 (3H, s, OCH$_3$).

5-(2-Methyl-5-methoxybenzylidene)-2-thioxo-1,3-thiazolidin-4-one as an orange crystalline solid (8.00 g, 91%); $\delta_H$ (300 MHz, CDCl$_3$) 7.80 (1H, s, Ar), 7.29-7.10 (1H, m, Ar), 6.95-6.84 (2H, m, Ar and CH=C), 3.83 (3H, s, OCH$_3$), 2.37 (3H, s, CH$_3$).

b) (2Z)-3-(2-Fluoro-5-methoxyphenyl)-2-mercapto-2-propenoic acid

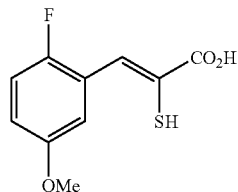

5-(2-Fluoro-5-methoxybenzylidene)-2-thioxo-1,3-thiazolidin-4-one (8.00 g, 9.7 mmol) was added in one portion to 25% w/v sodium hydroxide solution (40 mL). This was allowed stir at reflux for 1 h. After this time the reaction was allowed to cool to room temperature and poured onto water (50 mL). This was washed with dichloromethane (50 mL), and the aqueous layer acidified to pH 2 with aqueous hydrochloric acid (2 N, 50 mL) to give a white suspension. Product was extracted with ether (2×60 mL), dried (MgSO$_4$) and solvent removed in vacuo to give a white solid (6.71 g, 100%); $\delta_H$ (300 MHz, CD$_3$OD) 7.85 (1H, s, Ar), 7.46-7.35 (1H, m, Ar), 7.11 (1H, t, Ar), 7.01-6.75 (2H, m, CH=, and SH), 3.80 (3H, s, OCH$_3$).

Similarly prepared were (2Z)-3-(3-Fluoro-2-methoxyphenyl)-2-mercapto-2-propenoic acid as a solid (1.596 g, 94%); $\delta_H$ (300 MHz, CDCl$_3$) 8.12 (1H, s, ArCHCR$_2$), 7.60 (1H, d, Ar), 7.15-7.00 (2H, m, Ar), 4.55 (1H, s, SH), 3.98 (3H, s, OCH$_3$).

(2Z)-3-(2-Methyl-5-methoxyphenyl)-2-mercapto-2-propenoic acid as a white solid (6.71 g 100%); $\delta_H$ (300 MHz, CDCl$_3$) 8.00 (1H, s, CH=C), 7.30-7.09 (2H, m, Ar), 6.88-6.78 (1H, m, Ar), 3.80 (3H, s, OCH$_3$), 2.25 (3H, s, CH$_3$).

c) 4-Fluoro-7-methoxy-1-benzothiophene-2-carboxylic acid

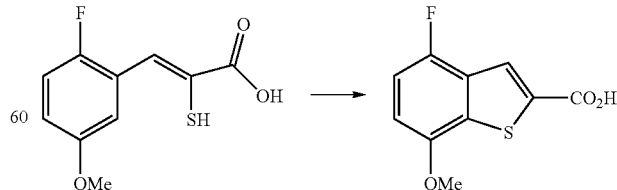

(2Z)-3-(2-Fluoro-5-methoxyphenyl)-2-mercapto-2-propenoic acid (1.00 g, 4.38 mmol) was added in one portion to a solution of iodine (1.66 g, 6.56 mmol) in dimethoxyethane (10 mL). This was heated in the microwave with 300 W at 160° C. for 10 mins. After this time the reaction was allowed to cool to room temperature and poured onto saturated sodium metabisulphite (200 mL) and ether (400 mL). Ether layer was separated and product extracted with aqueous sodium hydroxide (2 N, 2×100 mL). This was then acidified to pH 2 with aqueous hydrochloric acid (2 N, 250 mL), and product extracted with ether (2×150 mL). The combined organic extracts were dried (MgSO$_4$) and concentrated in vacuo to give a white solid (580 mg, 30%); δ$_H$ (300 MHz, CD$_3$OD) 8.00 (1H, s, Ar), 7.30-7.19 (1H, m, Ar), 7.10-7.00 (1H, m, Ar), 3.95 (3H, s, OCH$_3$).

Similarly prepared was
4-Methyl-7-methoxy-1-benzothiophene-2-carboxylic acid as white solid (580 mg, 30%); δ$_H$ (300 MHz, CDCl$_3$) 8.20 (1H, s, Ar), 7.12 (1H, d, Ar), 6.75 (1H, d, Ar), 3.99 (3H, s, OCH$_3$), 2.59 (3H, s, CH$_3$).

d) 4-Fluoro-7-methoxy-1-benzothiophene

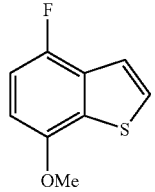

4-Fluoro-7-methoxy-1-benzothiophene-2-carboxylic acid (2.00 g, 8.84 mmol) was added in one portion to DBU (8 mL) and dimethyl acetamide (10 mL). This was heated in the microwave with 300 W at 200° C. for 1 h. The reaction mixture was allowed to cool and poured onto water (100 mL). Product was extracted with hexane (2×100 mL), washed with aqueous hydrochloric acid (2 N, 50 mL), aqueous sodium hydroxide (2 N, 50 mL), and the combined organic extracts were dried (MgSO$_4$) and concentrated in vacuo. The residue was purified by flash chromatography eluting silica gel with hexane:ethyl acetate [96:4] to give an oil (1.12 g, 70%); δ$_H$ (300 MHz, CDCl$_3$) 7.4 (2H, s, Ar), 6.9 (1H, t, Ar), 6.60 (1H, dd, Ar), 3.91 (3H, s, OCH$_3$).

Similarly prepared was
4-Methyl-7-methoxy-1-benzothiophene as an oil (1.12 g, 70%); δ$_H$ (300 MHz, CDCl$_3$) 7.46-7.32 (2H, m, Ar), 7.10 (1H, d, Ar), 6.66 (1H, d, Ar), 3.98 (3H, s, OCH$_3$), 2.52 (3H, s, CH$_3$).

5-Fluoro-4-methoxy-1-benzothiophene (2Z)-3-(3-Fluoro-2-methoxyphenyl)-2-mercapto-2-propenoic acid (4.865 g, 21.315 mmol) was added in one portion to a solution of iodine (8.255 g, 31.973 mmol) in dimethoxyetheane (30 mL). This was heated in the microwave with 300 W at 120° C. for 25 mins. After this time the reaction was allowed to cool to room temperature and poured onto saturated sodium metabisulphite (200 mL) and ether (400 mL). Ether layer was separated and product extracted with aqueous sodium hydroxide (2 N, 2×100 mL). This was then acidified to pH 2 with aqueous hydrochloric acid (2 N, 250 mL), and product extracted with ether (2×150 mL). The combined organic extracts were dried (MgSO$_4$) and concentrated in vacuo to give a tan coloured solid (3.240 g, 14.322 mmol, 67%). Which was used without further purification in the next step. 5-Fluoro-4-methoxy-1-benzothiophene-2-carboxylic acid (0.883 g, 3.903 mmol) was added in one portion to DBU (2.04 mL, 13.661 mmol) and dimethyl acetamide (10 mL). This was heated in the microwave with 300 W at 200° C. for 1 h. Reaction was allowed to cool and poured onto water (100 mL). Product was extracted with hexane (2×100 mL), washed with aqueous hydrochloric acid (2 N, 50 mL), aqueous sodium hydroxide (2 N, 50 mL), and the combined organic extracts were dried (MgSO$_4$) and concentrated in vacuo. The residue was purified by flash chromatography eluting silica gel with hexane:ethyl acetate [96:4] to give a pale yellow oil (0.167 g, 23%); δ$_H$ (300 MHz, CDCl$_3$) 7.60-6.80 (4H, m, Ar), 4.10 (3H, s, OCH$_3$).

7-Fluoro-4-methoxy-1-benzothiophene a) 2-(5-Fluoro-2-methoxyphenyl)-2-hydroxy-N,N-dimethylethanethioamide

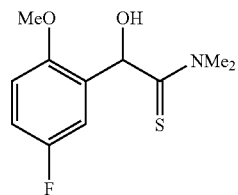

To a solution of lithium diisopropylamide, 2M in THF/n-heptane (210 mL, 583 mmol) was added THF (100 mL) and the solution cooled to −78° C. under nitrogen. This was then added dropwise over 1 h to a solution of the 5-fluoro-2-methoxybenzaldehyde (50 g, 0.32 mmol) and N,N-dimethylthioformamide (34.7 g, 389 mmol) in dry THF (200 mL). This was warmed to −5° C. and quenched with water (400 mL). The solution was filtered and washed with diethyl ether, the aqueous layer was extracted with ether (1 L). The combined organic layers were washed with water (500 mL), dried (MgSO$_4$) and the solvent removed in vacuo to give a crystalline suspension in oil. This was triturated in ether and filtered to give a crystalline solid (21.8 g, 28%); δ$_H$ (300 MHz, CDCl$_3$) 7.16-6.81 (3H, m, ArH), 5.81-5.75 (1H, m, CHOH), 5.31-5.22 (1H, m, OH), 4.89 (1H, s, OCH$_3$), 3.50 (3H, s, N(CH$_3$)$_2$) and 3.08 (3H, s, N(CH$_3$)$_2$).

b) N-(7-Fluoro 4-methoxy-1-benzothien-2-yl)-N,N-dimethylamine

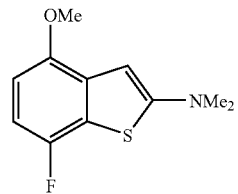

A solution of 2-(5-fluoro-2-methoxyphenyl)-2-hydroxy-N,N-dimethylethanethioamide (0.5 g, 2.1 mmol) in Eaton's reagent (i.e. P$_2$O$_5$/MeSO$_3$H) (5 mL) were combined and heated rapidly to 60° C. and left for 1 h. After cooling to room temperature over 2 hours the mixture was dropwise addition into prechilled aqueous sodium hydroxide (2 N, 16.25 mL) with constant stirring. This solution was then extracted with methyl tert-butyl ether (5×20 mL) and the combined organic extracts were dried (MgSO$_4$) and the solvent removed in vacuo to give a yellow solid. This was purified by flash chromatography with a gradient of 0-2% diethyl ether in hexane and gave 0.2 g of yellow solid containing an impurity, this was triturated with hexane to leave a colourless solid (0.155 g, 34%) of the title compound; $\delta_H$ (300 MHz, CDCl$_3$) 6.70-6.52 (2H, m, ArH), 6.12-6.10 (1H, m, ArH) 3.90 (3H, s, OCH$_3$) and 3.2 (6H, s, N(CH$_3$)$_2$), M+H=226.1.

c) 7-Fluoro-4-methoxy-1-benzothiophen-2(3H)-one

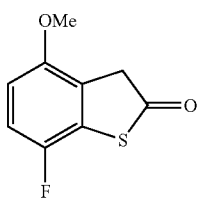

To a solution of N-(7-fluoro-4-methoxy-1-benzothien-2-yl)-N,N-dimethylamine (1.73 g, 7.7 mmol) in THF (25 mL) was added aqueous hydrochloric acid (1 N, 25 mL) and this was heated to 80° C. for 3 h. After cooling to room temperature then extracted with ether (100 mL), dried (MgSO$_4$) and the solvent evaporated in vacuo to give a yellow solid. The residue was purified by flash chromatography in 5% ethyl acetate in hexane to give (1.3 g, 84%) of the title compound; $\delta_H$ (300 MHz, CHCl$_3$) 6.97-6.87 (1H, m, ArH), 6.62-6.55 (1H, m, ArH), 3.91 (2H, s, CH$_2$) and 3.85 (3H, s, OCH$_3$).

d) 7-Fluoro-4-methoxy-1-benzothiophene

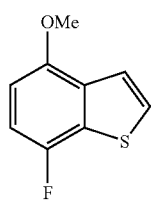

To a solution of 7-fluoromethoxy-4-methoxy-1-benzothiophen-2(3H)-one (1.06, 5.4 mmol) in dichloromethane (10 mL) at 0° C. was added slowly a solution of diisobutylaluminium hydride in dichloromethane (1 M, 8.04 mL, 8.0 mmol). After 30 mins the reaction was quenched by careful addition of aqueous hydrochloric acid (6 N, 25 mL). The mixture was concentrated to remove the dichloromethane, the aqueous residue was then stirred at 35° C. for 2 h. The aqueous solution was extracted with diethyl ether (3×50 mL), washed with aqueous sodium hydroxide (2 N, 50 mL), brine (50 mL) then dried (MgSO$_4$) and the solvent evaporated in vacuo to give the title compound (0.86 g, 87%) as a purple oil; $\delta_H$ 7.44-7.38 (1H, m, ArH), 7.36-7.24 (1H, m, ArH), 6.88-6.80 (1H, m, ArH), 6.57-6.49 (1H, m, ArH) and 3.82 (3H, s, OCH$_3$).

7-Fluoro-4-methoxy-1-benzothiophene a) 2,3-Difluoro-6-methoxybenzaldehyde

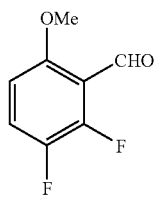

A solution of lithium diisopropylamide, 2M in THF/n-heptane (171 mL, 341 mmol) was further diluted with dry THF (250 mL) and cooled under nitrogen to −75° C. 3,4-Difluoroanisole (46.8 g, 325 mmol) in dry THF (100 mL) was added dropwise and the mixture stirred at −75° C. for 1 h. Dry N,N-dimethylformamide (27.6 mL, 358 mmol) was added dropwise and the mixture stirred for 10 mins at −70° C. Acetic acid (30 mL) and water (400 mL) were added, warming the temperature to 10° C. Extracted into diethyl ether (2×300 mL). Combined extracts were washed with water (250 mL), aqueous hydrochloric acid (0.2 N, 400 mL) and brine (2×250 mL), dried (MgSO$_4$) and the solvent evaporated in vacuo to give a red/orange oil which crystallised. Purification was by recrystallisation from diethyl ether/petroleum ether 40-60 to give (53.0 g, 95%) of solid; $\delta_H$ (300 MHz, CDCl$_3$) 10.40 (1H, s, CHO), 7.37 (1H, q, ArH), 6.71 (1H, m, ArH), and 3.93 (3H, s OCH$_3$).

b) Methyl 7-fluoro-4-methoxy-1-benzothiophene-2-carboxylate

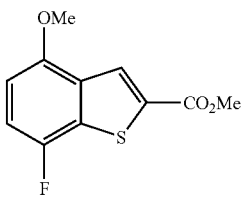

Methyl thioglycolate (28.8 mL, 320 mmol) was added under nitrogen to a solution of triethylamine (86.6 mL) in dry N,N-dimethylformamide (220 mL) at 80° C. Stirred at 100° C. for 15 mins. A solution of 2,3-difluoro-6-methoxybenzaldehyde (55.1 g, 320 mmol) in N,N-dimethylformamide (80 mL) was added and the mixture heated at 130° C. for 3 h. Allowed to cool then poured onto ice-water (2 L). The resulting yellow solid was filtered, washing with water (2×200 mL). Dried under vacuum over phosphorus pentoxide at room temperature overnight to give the title compound (67.2 g, 87%); $\delta_H$ (300 MHz, CDCl$_3$) 8.20 (1H, d, ArH), 7.06 (1H, t, ArH), 6.68 (1H, m, ArH) and 3.99 (6H, s, OCH$_3$ and CO$_2$CH$_3$).

c) 7-Fluoromethoxy-1-benzothiophene-2-carboxylic acid

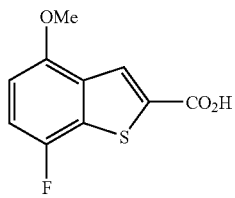

A mixture of methyl 7-fluoro-4-methoxy-1-benzothiophene-2-carboxylate (67.2 g, 280 mmol), sodium hydroxide (45 g, 1.12 mol), methanol (800 mL) and water (400 mL) were stirred at ambient overnight. The methanol was evaporated and the mixture cooled to 0° C. Acidified with concentrated hydrochloric acid and stirred for 20 mins. The yellow solid was filtered, washing with water (3×100 ml). Dried under vacuum at 45° C. overnight, over phosphorus pentoxide to give the title compound (61.4 g, 97%); $\delta_H$ (300 MHz, $d_6$-DMSO) 8.10 (1H, d, ArH) 7.44 (1H, t, ArH) 7.00 (1H, m, ArH) and 4.02 (3H, s, OCH$_3$).

d) 7-Fluoro-4-methoxy-1-benzothiophene

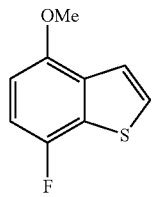

A mixture of 7-fluoro-methoxy-1-benzothiophene-2-carboxylic acid (61.4 g, 271 mmol) and copper powder (22.4 g, 352 mmol) in quinoline (500 mL) was heated at 190° C. for 1 h. Cooled to ambient and poured onto aqueous hydrochloric acid (2 N, 750 mL). Stirred with ethyl acetate (500 mL) for 15 minutes. Filtered through Celite, washing with ethyl acetate. The aqueous layer was extracted into ethyl acetate and the combined organic layers were washed with aqueous hydrochloric acid (2 N, 500 mL), water (500 mL), brine (500 mL), dried over MgSO$_4$ and evaporated in vacuo. Purified by column chromatography, eluting silica gel with iso-hexane/diethyl ether 0-5% to give the product as a brown oil which crystallised to give the title compound (41.3 g, 84%); $\delta_H$ (300 MHz, CDCl$_3$) 7.51 (1H, m, ArH), 7.38 (1H, d, ArH), 6.98 (1H, t, ArH), 6.65 (1H, dd, ArH) and 3.92 (3H, s, OCH$_3$).

3-Chloro-4-fluoro-7-methoxy-1-benzothiophene a) (2E)-3-(2-Fluoro-5-methoxyphenyl)-2-propenoic acid

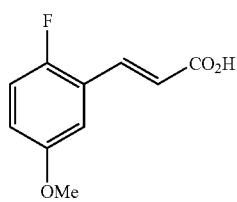

A solution of 2-fluoro-5-methoxybenzaldehyde (10.00 g, 64.9 mmol), malonic acid (13.4 g, 128.8 mmol), piperidine (2.00 mL) and pyridine (100 mL) was heated to 110° C. for 2 h. After this time the solvent was removed in vacuo and the residue taken up in ethyl acetate and washed with aqueous hydrochloric acid (2N, 100 mL). The organic solvent was dried (MgSO$_4$) and the solvent evaporated in vacuo. The solid was recrystallised from hot ethanol to give a white solid (12.2 g, 95%); $\delta_H$ (300 MHz, DMSO) 7.60 (1H, d, J 7 Hz, CH=C), 7.31-7.28 (1H, m, Ar), 7.20 (1H, t, Ar), 7.07-6.97 (1H, m, Ar), 6.62 (1H, d, J 8 Hz, CH=CH), 3.80 (3H, s, OCH$_3$).

b) Methyl 3-chloro-4-fluoro-7-methoxy-1-benzothiophene-2-carboxylate

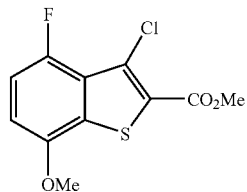

Thionyl chloride (3.7 mL, 50.8 mL) was added to a stirred solution of (2E)-3-(2-fluoro-5-methoxyphenyl)-2-propenoic acid (2.5 g, 12.7 mmol) and pyridine (100 µl). The resulting yellow suspension was stirred at 120° C. for 2 h before being allowed to cool to room temperature. The mixture was diluted with dichloromethane (50 mL) and concentrated in vacuo. The resulting yellow solid was taken up in methanol (100 mL) and heated to 70° C. for 1 hr. After this time the solvent was removed in vacuo to leave a white solid (984 mg, 28%); $\delta_H$ (300 MHz, CDCl$_3$) 7.09-6.98 (1H, m, Ar), 6.80-6.71 (1H, dd, Ar), 3.98 (6H, s, OCH$_3$ and CO$_2$CH$_3$).

c) 3-Chloro-4-fluoro-7-methoxy-1-benzothiophene-2-carboxylic acid

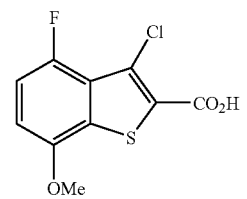

Methyl 3-chloro-4-fluoro-7-methoxy-1-benzothiophene-2-carboxylate (2.00 g, 7.29 mmol) was suspended in THF:H$_2$O [10:1] and lithium hydroxide (260 mg) added, the resulting suspension was heated to 40° C. for 1 h. After cooling to room temperature the mixture was extracted with diethyl ether (50 mL) and the aqueous phase acidified to pH 2 and the solid collected by filtration and vacuum dried to give a white solid (1.09 g, 58%); $\delta_H$ (300 MHz, DMSO) 7.32-7.20 (1H, m, Ar), 7.15-7.05 (1H, dd, Ar), 3.98 (3H, s, OCH$_3$).

d) 3-Chloro-4-fluoro-7-methoxy-1-benzothiophene

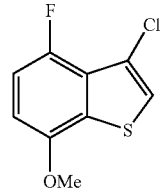

A mixture of 3-chloro-4-fluoro-7-methoxy-1-benzothiophene-2-carboxylic acid (1.09 g, 4.19 mmol) and diazobicycloundecane (DBU) (2 mL) in dimethylacetamide (15 mL) was heated in a sealed vessel in a microwave (300 W, 100%) for 1 h. After cooling to room temperature the mixture was diluted with diethyl ether (100 mL) and washed with brine (2×100 mL). The organic phase was dried (MgSO$_4$) and the solvent removed in vacuo. The residue was purified by flash chromatography eluting silica gel with hexane:diethyl ether [10:1] to yield a white solid (520 mg, 57%); $\delta_H$ (300 MHz, CDCl$_3$) 7.24 (1H, s, Ar), 7.05-6.92 (1H, m, Ar), 6.70-6.60 (1H, dd, Ar), 3.96 (3H, s, OCH$_3$).

4-Fluoro-7-methoxy-3-methyl-1-benzothiophene

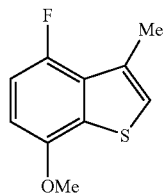

1-[(5-fluoro-2-methoxyphenyl)thio]acetone (1.00 g, 4.67 mmol) was added to a stirred solution of polyphosphoric acid (2.00 g) and chlorobenzene (70 mL). The resulting solution was stirred rapidly at 160° C. for 18 h. After this time the solution was allowed to cool to room temperature and washed with water (50 mL). The aqueous phase was extracted with dichloromethane (3×30 mL) and the combined organic extracts dried (MgSO$_4$). The solvent was removed in vacuo and the residue purified by flash chromatography eluting silica gel with hexane:ethyl acetate [10:1] to give a pale yellow oil (700 mg, 76%); R$_f$=0.72 in hexane:ether [10:1]; $\delta_H$ (300 MHz, CDCl$_3$) 7.44-7.20 (1H, m, Ar), 6.99-6.82 (1H, m, Ar), 6.62-6.55 (1H, dd, Ar), 3.95 (3H, s, OCH$_3$), 2.56 (3H, s, CH$_3$).

Similarly prepared was

7-Fluoro-4-methoxy-3-methyl-benzothiophene as an oil (1.43 g, 91%); $\delta_H$ (300 MHz, CDCl$_3$) 7.22 (1H, s, ArH), 6.89-6.81 (1H, m, ArH), 6.59-6.52 (1H, m, ArH), 3.81 (3H, s, OCH$_3$) and 2.56 (3H, s, CH$_3$).

2-Fluoro-7-methoxy-1-benzothiophene

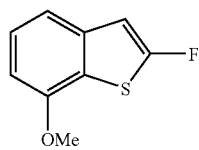

A solution of 1-benzothien-7-yl methyl ether (230 mg, 1.40 mmol) in dry THF (5 mL) was added dropwise to a freshly prepared solution of 2,2,6,6 tetramethyl-4-lithio-piperidine (1.68 mmol) in THF (10 mL) at −78° C. The resulting solution was stirred at this temperature for 30 mins before perchloryl fluoride gas was condensed into the reaction. After the strong exotherm had stopped the mixture was allowed to stir at −78° C. for a further 30 mins. After this time the reaction was quenched with NH$_4$Cl (sat, 20 mL) and diluted with diethyl ether. The organic phase was dried (MgSO$_4$) and the solvent removed in vacuo. The residue was purified by flash chromatography eluting silica gel with hexane to yield a colourless oil (128 mg, 50%); $\delta_H$ (300 MHz, CDCl$_3$) 7.32-7.20 (2H, m, Ar), 6.80-6.62 (2H, m, Ar), 3.95 (3H, s, OCH$_3$).

Similarly prepared was

2-Fluoro-4-methoxy-1-benzothiophene as a colourless oil (420 mg, 48%); $\delta_H$ (300 MHz, CDCl$_3$) 7.32-7.20 (2H, m, Ar), 6.80-6.62 (2H, m, Ar), 3.95 (3H, s, OCH$_3$).

7-Methoxy-1-benzothiophene-2-carbonitrile

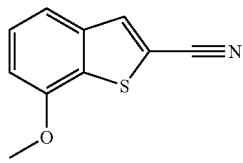

To a solution of 1-benzothien-7-yl methyl ether (1 g, 6.1 mmol) in THF (12 mL) at −78° C. was added a solution of 2.5 M n-butyllithium in hexanes (2.9 mL, 7.3 mmol). After stirring for 1.5 hr this solution was added dropwise to a solution of tosyl cyanide (1.66 g, 9.1 mmol) in THF (8 mL), this was left stirring at −78° C. for 0.5 hr and then warmed to room temperature. After 16 h this was poured onto ice-water and extracted with dichloromethane (3×50 mL). The combined organic extracts were washed with water, dried (MgSO$_4$) and the solvent removed in vacuo to give an oil. This was purified by flash chromatography with a gradient of 0-30% ethyl acetate in hexane to give the title compound (0.31 g, 27%); $\delta_H$ (300 MHz, CDCl$_3$) 7.79 (1H, s, 3-ArH), 7.46-7.38 (1H, m, 4-ArH), 7.37-7.31 (1H, m, 5-ArH), 6.88-6.82 (1H, m, 6-ArH) and 3.94 (3H, s, OCH$_3$). Starting material 1-benzothien-7-yl methyl ether was recovered from the reaction (0.56 g, 56%); $\delta_H$ (300 MHz, CDCl$_3$) 7.45-7.29 (4H, m, ArH), 6.75 (1H, m, ArH), 4.00 (3H, s, OCH$_3$).

7-Methoxy-1-benzothiophene-2-carbonitrile a) 2-Iodo-7-methoxy-1-benzothiophene

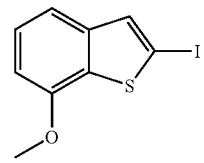

In a 4 L mechanically stirred reactor, a solution of 1-benzothien-7-yl methyl ether (105 g, 0.64 mol) in anhydrous THF (2 L) is cooled down to −74° C. n-Butyl lithium in hexane is added (2.5 N, 285 mL, 0.71 mol) within 45 min, keeping temperature below −70° C. The mixture is stirred 30 min at −78° C. and a solution of iodine (179 g, 0.70 mol) in anhydrous THF (1 L) is added within 1 h, keeping temperature below −70° C. After addition, the mixture is allowed to come up to room temperature over 2 h and brine (500 mL) is added. The layers are roughly separated and the organic layer is partially evaporated. Additional brine (200 mL) is added to the residual aqueous layer (mixed with some THF). After decantation, the organic and aqueous layers are separated. The aqueous layer is extracted with ethyl acetate (500 mL). The organic layers are pooled, washed with aqueous sodium thiosulphate, dried (MgSO$_4$) and the solvent evaporated in vacuo to give the crude iodo derivative (173.6 g, 93%) The solid is recrystallized from isopropanol (150 mL) to give pure compound (145.5 g, 88%); $\delta_H$ (600 MHz, CDCl$_3$) 7.51 (s, 1H), 7.32 (d(br), J=7.89 Hz, 1H), 7.26 (t, J=7.89 Hz, 1H), 6.72 (d(br), J=7.89 Hz, 1H), 3.97 (s, 3H).

b) 7-Methoxy-1-benzothiophene-2-carbonitrile

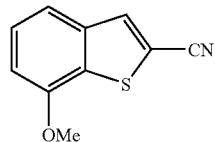

A solution of 2-iodo-7-methoxy-1-benzothiophene (10.0 g, 0.35 mol), copper (1) cyanide (6.17 g, 0.68 mol) and anhydrous N,N-dimethylformamide (40 mL) are warmed to 130° C. After 2.5 h at 130° C. no starting material is detectable as measured by HPLC at 220 nm. The reaction is cooled to 40° C. and a solution 25% v/v ethylenediamine in water (30 mL) and toluene (20 mL) are added. The mixture is stirred to room temperature. Additional toluene (30 mL) is added and the heterogeneous mixture is filtered. The layers of the mother liquors are separated and the aqueous layer is extracted with toluene (3×50 mL). The combined organic extracts were washed with water (2×50 mL), dried (MgSO$_4$) and the solvent evaporated in vacuo to give the title compound (5.78 g, 88%), which was used without further purification; $\delta_H$ (300 MHz, CDCl$_3$) 7.79 (1H, s, 3-ArH), 7.46-7.38 (1H, m, 4-ArH), 7.37-7.31 (1H, m, 5-ArH), 6.88-6.82 (1H, m, 6-ArH) and 3.94 (3H, s, OCH$_3$).

4-Methoxy-1-benzothiophene-2-carbonitrile

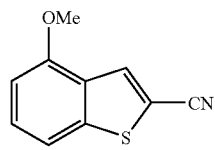

(Ref: Cheutin et al.; C. R. Hebd. Seances Acad. Sci; 261; 1965; 705.) A solution of 4-methoxy-1-benzothiophene-2-carboxylic acid (1.19 g, 5.7 mmol) in pyidine (25 mL) at 0° C. was treated with methanesulfonyl chloride (0.49 mL, 6.3 mmol) keeping the temperature at 0° C., stirring was continued for 2 h. Ammonia gas was then bubbled through the mixture for 5 minutes, followed by nitrogen for 10 mins. The reaction mixture was then treated with a large excess of mesyl chloride (4.43 mL, 57 mmol) and stirred for 16 h at room temperature. The solvent evaporated in vacuo to give a brown residue which was purified by flash chromatography with 10% ethyl acetate in hexane to give a colourless solid (800 mg, 74%); $\delta_H$ (300 MHz, CDCl$_3$) 8.00 (1H, s, 3-Ar), 7.48-7.35 (2H, m, ArH), 6.80-6.77 (1H, m, ArH) and 3.92 (3H, s, OCH$_3$).

4-Fluoro-7-methoxy-1-benzothiophene-2-carbonitrile a) 4-Fluoro-7-methoxy-1-benzothiophene-2-carboxamide

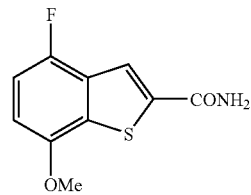

A solution of 4-fluoro-7-methoxy-1-benzothiophene-2-carboxylic acid (1.5 g, 6.6 mmol) in thionyl chloride (4 mL) was heated to 50° C. for 30 minutes, then the solvent removed in vacuo. The residue was taken up in dichloromethane (60 mL) and methanol (0.5 mL) and then added to a solution of concentrated ammonium hydroxide (40 mL) and dichloromethane (40 mL) at 5° C. After 10 min the solution was warmed to room temperature and stirred for 2 h. The dichloromethane was evaporated in vacuo and the solid filtered to give a pale browm solid (0.75 g, 51%); $\delta_H$ (300 MHz, D$_4$-Methanol) 7.95 (1H, s, 3—ArH), 7.02-6.92 (1H, m, ArH), 6.83-6.77 (1H, m, ArH), 3.89 (3H, s, OCH$_3$) and 3.23-3.28 (2H, m, CONH$_2$).

b) 4-Fluoro-7-methoxy-1-benzothiophene-2-carbonitrile

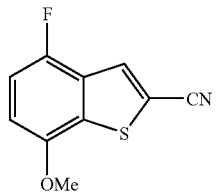

A solution of 4-fluoro-7-methoxy-1-benzothiophene-2-carboxamide (0.756 g, 3.3 mmol) in phosphorus oxychloride (6.2 mL, 6.6 mmol) was refluxed for 3 h then cooled and the solvent evaporated in vacuo to give the title compound. Purified by flash chromatography with a gradient of 0-30% ethyl acetate in iso-hexane to give a colourless solid (0.635 g, 91%); $\delta_H$ (300 MHz, CDCl$_3$) 7.95 (1H, s, 3-ArH), 7.10-7.01 (1H, m, ArH), 6.85-6.77 (1H, m, ArH) and 3.98 (3H, s, OCH$_3$).

4-Cyano-7-methoxy benzo[b]thiophene

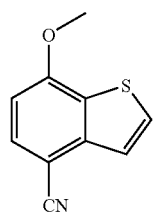

To a stirred solution of 4-bromo-7-methoxy benzo[b]thiophene (1.05 g, 4.32 mmol, 1 equiv.) in dry DMF (40 mL) was added copper(I)cyanide (3.885 g, 43.4 mmol, 10 equiv.)

and the reaction mixture was heated at 150° C. overnight. The reaction mixture was cooled to ~120° C. and then solid iron (III)chloride (1.58 g, 9.74 mmol) was added followed by 1 N HCl (CAUTION: HCN evolution—perform in a well vented hood!) The reaction mixture was heated at ~100° C. for 2 hr before cooling to room temperature. Water, brine, and ethyl acetate were added and the layers were separated. The organic layer was washed with brine (3 times), dried over anhydrous magnesium sulfate, filtered, and concentrated under reduced pressure. The crude residue thus obtained was purified via medium pressure liquid chromatography eluting with 10% ethyl acetate/90% hexanes to afford the title compound (564 mg, 69%) as a colorless solid; ☐$_H$ (400 MHz, CDCl$_3$) 4.06 (3H, s), 6.81 (1H, d, J=8 Hz), 7.56 (1H, d, J=6 Hz), 7.65 (1H, d, J=6 Hz), 7.71 (1H, d, J=8 Hz).

Ref: (J. Chem. Soc. Perkin Trans 1 1983, 2973).

6-Methoxy-1-benzothiophene-2-carbonitrile a) O-(2-Formyl-5-methoxyphenyl)dimethylthiocarbamate

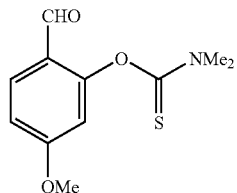

A solution of N,N-dimethylcarbamoyl chloride (4.46 g, 35.7 mmol) in THF (20 mL) was added over 15 minutes to a stirred cooled (0° C.), solution of 2-hydroxy-4-methoxybenzaldehyde (5 g, 32.9 mmol) and potassium hydroxide (2 g, 35.7 mmol) in water (25 mL) such that the temperature did not rise above 10° C. The mixture was stirred for 10 minutes at room temperature then extracted with ethyl acetate (3×50 mL), the combined organic layers were washed successively with 2M sodium hydroxide (100 mL), 2N hydrochloric acid (100 mL), brine (100 mL) then dried MgSO$_4$) and the solvent removed in vacuo to give a yellow solid (6.8 g, 86%) which was used without further purification; δ$_H$ (300 MHz, CDCl$_3$) 7.88-7.80 (1H, m, ArH), 7.95-7.85 (1H, m, ArH), 6.65-6.60 (1H, m, ArH), 3.88 (3H, s, OCH$_3$), 3.46 (3H, s, N(CH$_3$)$_2$) and 3.40 (3H, s, N(CH$_3$)$_2$).

b) S-(2-Formyl-5-methoxyphenyl)dimethylthiocarbamate

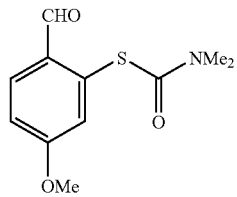

A pre-warmed solution of O-(2-formyl-5-methoxyphenyl) dimethylthiocarbamate (2 g, 8.3 mmol) in diphenyl ether (4 mL) was added to diphenyl ether (36 mL) at 230° C. The mixture was heated at 230° C. for 1.5 h. The reaction mixture was loaded neat onto flash chromatography column and solvent eluted with iso-hexane. Product eluted with a gradient of 0-30% ethyl acetate in iso-hexane. Further purified by flash chromatography with a gradient of 0-20% ethyl acetate in dichloromethane, followed by triturating with iso-hexane gave a solid which was recrystallised from ethyl acetate hexane to give the title compound (1.21 g, 61%); δ$_H$ (300 MHz, CDCl$_3$) 8.04-7.95 (1H, m, ArH), 7.09-6.99 (2H, m, ArH), 3.89 (3H, s, OCH$_3$), 3.16 (3H, br. s, N(CH$_3$)$_2$) and 3.02 (3H, br. s, N(CH$_3$)$_2$).

6-Methoxy-1-benzothiophene-2-carbonitrile

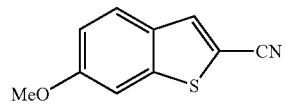

(Ref: Gallagher, T; Pardoe, D. A.; Porter, R. A.; Tetrahedron Lett.; 2000, 41(28), 5415-5418.) To a solution of S-(2-formyl-5-methoxyphenyl)dimethylthiocarbamate (1.08 g, 4.5 mmol) in water (4 mL) and methanol (8 mL) was added sodium hydroxide (199 mg, 4.9 mmol), this was heated to reflux for 16 hours. The reaction was cooled to room temperature and chloroacetonitrile (0.28 mL, 4.5 mmol) was added in one portion and the mixture the stirred at room temperature for 1 hour. The methanol was removed in vacuo, and water (10 mL) added. The aqueous layer was extracted with diethyl ether (3×20 mL), dried (MgSO$_4$) and the solvent removed in vacuo. The residue was purified by flash chromatography with a gradient of 0-30% ethyl acetate in iso-hexane to give the title compound as a colourless solid (390 mg, 46%); δ$_H$ (300 MHz, CDCl$_3$) 7.80-7.70 (1H, m, ArH), 7.29 (2H, m, ArH), 7.11-7.01 (1H, m, ArH) and 3.85 (3H, s, OCH$_3$). M+23=212.0. v$_{max}$/cm$^{-1}$ [film] 2213.50 (m).

1-Benzothiophen-4-ol a) 5-Bromo-6,7-dihydro-1-benothiophen-4(5H)-one

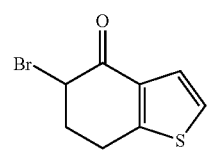

Ref: J. Chem. Res. (S) 1993, 192-193. Bromine (6.4 g, 40 mmol) in dry carbon tetrachloride containing a few drops of diethyl ether (20 mL) was added dropwise to a well stirred solution 6,7-dihydro-1-benzothiophen-4(5H)-one (6.08 g; 40 mmol) in dry diethyl ether (250 mL) allowing the solution to decolourise between additions and the temperature maintained at −10° C. Once the addition was complete, the solution was allowed to warm slowly to room temperature. Water (200 mL) was slowly added and the mixture transferred to a separating funnel with ether (100 mL). The organic phase was washed with water (100 mL), dried over magnesium sulfate and evaporated to an oil which solidified on standing (8.56 g, 88%), this material was used without further purifictaion. δ$_H$ (300 MHz, CD$_3$OD) 7.36 (1H, d, Ar) 7.30 (1H, d, Ar), 4.63 (1H, t, CH) 3.20 (2H, m, CH$_2$), 2.56 (2H, m, CH$_2$).

b) 1-Benzothiophen-4-ol

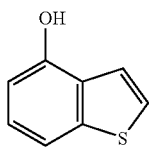

5-Bromo-6,7-dihydro-1-benzothiophen-4(5H)-one (11.4 g, 50 mmol), lithium bromide (10 g) and lithium carbonate (7.4 g) were refluxed for 3 h in dry N,N-dimethylformamide (250 mL) under nitrogen. The solvent was evaporated in vacuo and the residue treated with cold aqueous hydrochloric acid (1 N, 250 mL). Extracted into diethyl ether (3×200 mL). The ethereal layer was extracted with 10% aqueous sodium hydroxide solution (2×). Combined aqueous layers were acidified and extracted into ether. Dried over magnesium sulfate and evaporated to an oil. Purified by chromatography eluting silica gel with ethyl acetate-hexane (4-6%). Combined fractions were evaporated to a light yellow oil which crystallised on standing, this material was triturated with cyclohexane to give white plates (3.6 g; 51%). $\delta_H$ (300 MHz, $CD_3OD$) 7.45 (1H, d, Ar), 7.30-7.40 (2H, m, Ar), 7.12 (1H, m, Ar), 6.70 (1H, m, Ar).

5-Fluoro-benzo[b]thiophen-4-ol a) 5-Fluoro-6,7-dihydro-5H-benzo[b]thiophen-4-one

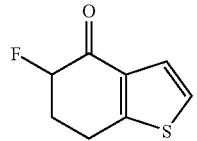

Add trimethylsilyl trifluoromethanesulfonate (18.5 mL, 102 mmol, 1.3 equiv.) over 5 minutes to a cold (0° C.) stirred solution of solution 6,7-dihydro-1-benothiophen-4(5H)-one (12.04 g, 79.1 mmol, 1 equiv.) and triethylamine (33 mL, 237 mmol, 3 equiv.) in dry dichloromethane (200 mL). Stir the reaction mixture at 0° C. for 5 minutes and then warm to room temperature for 1 h 10 min before adding water. Separate the layers, extract the aqueous layer twice with dichloromethane, dry the combined organic extracts over anhydrous magnesium sulfate, filter, and concentrate under reduced pressure. Dissolve the resulting crude silylenol ether in anhydrous dimethylformamide (200 mL), place the reaction mixture in a room temperature water bath, and add 1-(chloromethyl)-4fluoro-1,4-diazoniabicyclo[2.2.2]octanebis(tetrafluoroborate) (Selectfluor™) (31.06 g, 87.7 mmol, 1.1 equiv.) in one portion. Stir the reaction mixture at room temperature for 15 minutes then add tetrabutylammonium fluoride (1M in TBF, 87 mL, 87 mmol, 1.1 equiv.) and stir at room temperature for 1 hr before adding water and ethyl acetate. Separate the layers, extract the aqueous layer three times with ethyl acetate, wash the combined organic extracts successively with water (2 times) then 0.1N HCl (2 times), dry the combined organic extracts over anhydrous magnesium sulfate, filter, and concentrate under reduced pressure. Purify the resultant crude material by medium pressure liquid chromatography eluting with 0 to 20% ethyl acetate in hexanes to afford the title compound as an orange solid (9.725 g, 72%). $\delta_H$ (400 MHz, $CDCl_3$) 2.41-2.54 (m, 1H), 2.56-2.67 (m, 1H), 3.10-3.20 (m, 1H), 3.23-3.33 (m, 1H), 5.12 (ddd, 1H, J=47, 11, 4 Hz), 7.15 (d, 1H, J=6 Hz), 7.41 (d, 1H, J=6 Hz).

b) 5-Bromo-5-fluoro-6,7-dihydro-5H-benzo[b]thiophen-4-one

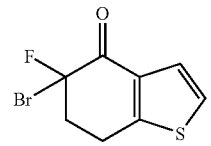

Add a solution of bromine (10.08 g, 63.1 mmol, 1.1 equiv.) in dry carbon tetrachloride (60 mL) dropwise via addition funnel over 1 h 20 min to a cold (0° C.) solution of 5-fluoro-6,7-dihydro-5H-benzo[b]thiophen-4-one (9.72 g, 57.1 mmol, 1 equiv.) in dry diethyl ether (300 mL). Once all the bromine is added warm to room temperature for 2 hours and add more bromine (0.7 M in $CCl_4$, 7 mL, 4.9 mmol, 0.09 equiv.) and stir the reaction mixture at room temperature for 1 hr before adding saturated aqueous sodium thiosulfate. The layers are separated and the aqueous layer is extracted with diethyl ether (three times). The combined organic extracts are dried over anhydrous magnesium sulfate, filtered, and concentrated under reduced pressure. Purify the resultant crude material by medium pressure liquid chromatography eluting with 0 to 20% ethyl acetate in hexanes to afford the title compound (6.976 g, 49%). $\delta_H$ (400 MHz, $CDCl_3$) 2.67-2.78 (m, 1H), 2.93 (dddd, 1H, J=14, 4, 4, 4 Hz), 3.24-3.31 (m, 2H), 7.21 (d, 1H, J=6 Hz), 7.45 (d, 1H, J=6 Hz).

c) 5-fluoro-benzo[b]thiophen-4-ol

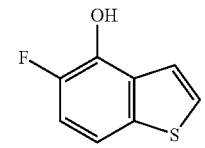

Heat a mixture of 5-bromo-5-fluoro-6,7-dihydro-5H-benzo[b]thiophen-4-one (6.97 g, 28.0 mmol 1 equiv.), lithium carbonate (4.34 g, 58.7 mmol, 2.1 equiv.), and lithium bromide (5.61 g, 64.6 mmol, 2.3 equiv.) in dry dimethylformamide (150 mL) at 150° C. (internal temperature) for 2 hours. Cool the reaction mixture to room temperature, add ice water, and then carefully add 5N HCl until gas evolution ceases and the mixture is acidic. Add ethyl acetate, separate the layers, and extract the aqueous layer with ethyl acetate (3 times). Extract the combined organic extracts with 2N sodium hydroxide (2 times), reacidify the aqueous layers with hydrochloric acid, and then re-extract the aqueous layer with dichloromethane (3 times). Dry the dichloromethane extracts over anhydrous magnesium sulfate, filter, and concentrate under reduced pressure. Purify the resultant crude material by medium pressure liquid chromatography eluting with 0 to 10% ethyl acetate in hexanes to afford the title compound as a colorless solid (3.738 g, 79%). $\delta_H$ (400 MHz, $CDCl_3$) 5.35

(br s, 1H), 7.13 (dd, 1H, J=10, 8 Hz), 7.34 (ddd, 1H, J=8, 4, 1 Hz), 7.42 (d, 1H, J=6 Hz), 7.49 (dd, 1H, J=6, 1 Hz).

Boron Tribromide Demethylation: General Procedure

1-Benzothiophen-7-ol

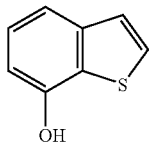

A solution of boron tribromide (115 µl, 1.21 mmol) was added dropwise at room temperature to a stirred solution of 7-methoxy-benzothiophene (200 mg, 1.21 mmol) in dry dichloromethane (10 mL). The resulting solution was allowed to stir at room temperature for a further 1 hr, after which the solvent was removed in vacuo and the residue taken up in ethyl acetate (20 mL) and extracted with aqueous hydrochloric acid (2 N, 10 ml). The organic phase was dried (MgSO$_4$) and the solvent was removed in vacuo. The resulting dark yellow oil was purified by flash chromatography eluting silica gel with hexane:ethyl acetate [4:1] to yield a white solid (68 mg, 38%); $\delta_H$ (300 MHz, CDCl$_3$) 7.50-7.39 (2H, m, Ar), 7.29-7.21 (1H, m, Ar), 7.21-7.15 (1H, m, Ar), 6.70 (1H, d, Ar), 5.15 (1H, bs, OH).

Similarly prepared were

5-Fluoro-1-benzothiophen-7-ol as a brown crystalline solid (393 mg, 42%); $\delta_H$ (300 MHz, CDCl$_3$) 7.50 (1H, d, Ar), 7.28 (1H, d, Ar), 7.10 (1H, dd, Ar), 6.58 (1H, dd, Ar), 5.40 (1H, s, OH).

4-Trifluoromethyl-1-benzothiophen-6-ol as a brown crystalline solid (1.576 g, 62%); $\delta_H$ (300 MHz, CDCl$_3$) 7.50-7.40 (3H, m, Ar), 7.22 (1H, d, Ar), 5.30 (1H, bs, OH).

5-Fluoro-1-benzothiophen-4-ol as a white crystalline solid (0.074 g, 21%); $\delta_H$ (300 MHz, CDCl$_3$) 7.50 (1H, d, Ar), 7.42 (1H, d, Ar), 7.35 (1H, m, Ar), 7.10 (1H, t, Ar), 5.40 (1H, bs, OH).

4-Methyl-1-benzothiophen-7-ol as an oil (290 mg, 79%); $\delta_H$ (300 MHz, CDCl$_3$) 7.44 (1H, d, Ar), 7.32 (1H, d, Ar), 7.00 (1H, d, Ar), 6.61 (1H, d, Ar), 4.92 (1H, s, OH), 2.52 (3H, s, CH$_3$).

7-Fluoro-1-benzothiophen-4-ol as a solid (0.68 g, 79%); $\delta_H$ 7.45 (1H, m, ArH), 7.40 (1H, d, ArH), 6.90 (1H, t, ArH) and 6.74 (1H, m, ArH) and 5.00 (1H, br. s, OH).

3-Chloro-4-fluoro-1-benzothiophen-7-ol as a white solid (145 mg, 97%); $\delta_H$ (300 MHz, CDCl$_3$) 7.25 (1H, s, Ar), 7.05-6.85 (1H, m, Ar), 6.72-6.61 (1H, dd, Ar).

3-Methyl-4-fluoro-1-benzothiophen-7-ol as a white solid (447 mg, 69%); $\delta_H$ (300 MHz, CDCl$_3$) 7.28 (1H, s, Ar), 6.99 (1H, s, OH), 6.90-6.78 (1H, m, Ar), 6.60 (1H, dd, Ar), 2.57 (3H, s, CH$_3$).

7-Fluoro-3-methyl-1-benzothiophen-4-ol as a solid (0.77 g, 70%); $\delta_H$ (300 MHz, CDCl$_3$) 7.26 (1H, s, ArH), 6.85-6.77 (1H, m, ArH), 6.58-6.50 (1H, m, ArH), 4.98 (1H, s, OH) and 2.65 (3H, s, CH$_3$).

2-Fluoro-1-benzothiophen-7-ol as a colourless oil (502 mg, 50%); $\delta_H$ (300 MHz, CDCl$_3$) 7.35-7.12 (3H, m, Ar), 6.72-6.63 (1H, dd, Ar).

2-Fluoro-1-benzothiophen-4-ol as a colourless oil (213 mg, 55%); $\delta_H$ (300 MHz, CDCl$_3$) 7.44 (1H, d, Ar), 7.41-7.12 (2H, m, Ar), 6.72-6.63 (1H, dd, Ar).

7-Hydroxy-1-benzothiophene-2-carbonitrile as a solid (3.9 g, 74%). $\delta_H$ (250 MHz, DMSO-D6) 6.98 (dd, J=7.87, 0.94 Hz, 1H) 7.37 (t, J=7.87 Hz, 1H) 7.49 (dd, J=7.87, 0.94 Hz, 1H) 8.34 (s, 1H) 10.87 (s, 1H). Negative FIA: M−1=174.1.

4-Hydroxy-1-benzothiophene-2-carbonitrile as a solid (0.65 g, 95%) $\delta_H$ (300 MHz, CDCl$_3$) 8.05 (1H, s, 3—ArH), 7.43-7.34 (2H, m, ArH), 7.80-7.75 (1H, m, ArH) and 5.68 (1H, br. s, OH). Negative FIA: M−1=174.1.

4-Fluoro-7-hydroxy-1-benzothiophene-2-carbonitrile as a solid (160 mg, 27%); $\delta_H$ (300 MHz, CDCl$_3$) 7.94 (1H, s, 3—ArH), 7.04-6.92 (1H, m, ArH), 6.85-6.76 (1H, m, ArH) and 5.52 (1H, br. s, OH).

6-Hydroxy-1-benzothiophene-2-carbonitrile as a solid; (0.36 g, 64%); $\delta_H$ (300 MHz, D$_4$-Methanol) 7.85 (1H, s, ArH), 7.73-7.62 (1H, m, ArH), 7.16 (1H, s, ArH) and 6.95-6.83 (1H, m, ArH). M+1=176.1.

6-Fluoro-1-benzothiophene-7-ol

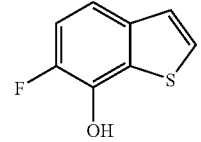

(Ref: Briner, K; Burkholder, T. P; Conway, R. G; Cunningham, B. E; Finley, D. R; Heinz, L. J; Jesudason, C. D; Kohlman, D. T; Liang, S. X; Xu, Y. C. Preparation and use of serotonergic benzothiophenes. WO 0109126 A1. Chem. Abs. 134:162912). To a solution of 7-bromo-6-fluoro-1-benzothiophene (0.2 g, 0.9 mmol) and trimethylborate (0.2 mL, 1.8 mmol) at −78° C. was added tert-butyllithium dropwise. After 10 mins at −78° C. the reaction was quenched by pouring onto saturated ammonium chloride. This was extracted with ethyl acetate (3×10 mL) and the solvent removed in vacuo from the combined organic extracts. The residue was taken up in ethyl acetate (4 mL) and 10% aqueous hydrochloric acid (4 mL) was added, the mixture was stirred at room temperature for 1 h. The organic layer was separated and the aqueous layer extracted with ethyl acetate (2×10 mL). The combined organic extracts were dried (MgSO$_4$) and the solvent removed in vacuo. The residue was taken up in THF (10 mL), water (2 mL) and cooled to 0° C. then 10% aqueous sodium hydroxide (2 mL) and 28% hydrogen peroxide (1 mL) were added to this and stirred for 0.5 h at 0° C. The mixture was warmed to room temperature and stirred for 2 hours, before a acetic acid (3 mL) was added. The mixture was extracted with ethyl acetate (3×10 mL), dried (MgSO$_4$) and the solvent removed in vacuo, to give a purple solid. This was purified by flash chromatography with a gradient of 0-20% ethyl acetate in iso-hexane to give the title compound (56 mg, 38%); $\delta_H$ (300 MHz, CDCl$_3$) 7.41 (4H, m, ArH).

4-Cyano-7-hydroxy benzo[b]thiophene

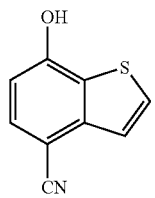

To a solution of 4-cyano-7-methoxy benzo[b]thiophene (450 mg, 2.38 mmol, 1 equiv.) in dry DMF (20 mL) was added sodium ethanethiolate (80% technical grade, 1.34 g, ~13 mmol, ~5 equiv.) and the reaction mixture was heated at 150° C. for 2 hr. The mixture was cooled to room temperature and ethyl acetate and 1N HCl were added and the layers were separated. The aqueous layer was extracted with ethyl acetate and the combined organic extracts were washed with brine (3 times), dried over anhydrous magnesium sulfate, filtered, and concentrated under reduced pressure. The acquired material thus obtained was purified via medium pressure liquid chromatography eluting with 30% ethyl acetate/70% hexanes to afford the title compound (414 mg, 99%) as a colorless solid; $\delta_H$ (400 MHz, CD$_3$OD) 6.80 (1H, d, J=8 Hz), 7.47 (1H, d, J=6 Hz), 7.64 (1H, d, J=8 Hz), 7.83 (1H, d, J=6 Hz).

1-Benzofuran-7-ol

1-Benzofuran-7-ol was synthesised from 7-methoxy-1-benzofuran, (Ref.: Musser, J. H.; Chakraborty, U; Bailey, K; Sciortino, S; Whyzmuzis, C; Amin, D; Sutherland, C. A. J. Med. Chem. (1987), 30(1), 62-7.) as a solid (0.73 g, 82%); $\delta_H$ (300 MHz, CDCl$_3$) 7.61 (1H, d, Ar), 7.16 (2H, m, Ar), 6.82 (2H, m, Ar), 5.37 (1H, bs, —OH).

2-Methyl-benzofuran-7-ol

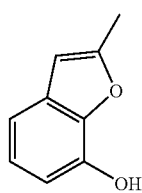

A solution of 7-methoxy-benzofuran (1.5 g, 10 mmol) in 50 mL of THF was cooled to –78° C. n-Butyl lithium (8.3 mL, 13 mmol) was then added and after 0.25 h the reaction was warmed to –20° C. and stirred a further 1 h. Methyl iodide (1.83 mL, 30 mmol) was added and the reaction was stirred overnight at room temperature. The reaction was diluted with ethyl acetate and NH$_4$Cl (sat). After separation, the reaction was extracted 2 more times with CH$_2$Cl$_2$ and the combined organics were dried MgSO$_4$, filtered and concentrated in vacuo. This material was purified by flash chromatography, eluting silica gel with hexane:ethyl acetate (100:0 to 3:1) to give the product. (1.37 g, 86%). This material was dissolved in 25 mL of CH$_2$Cl$_2$ was added 1M BBr$_3$ in CH$_2$Cl$_2$ (18.9 mL, 18.9 mmol) via syringe. The resulting solution was allowed to stir at room temperature for 24 h. The solution was poured into a rapidly stirring solution of 1N HCl and CH$_2$Cl$_2$. After stirring for 15 min, the solution was allowed to separate and the aqueous phase was extracted 2 times with CH$_2$Cl$_2$. The combined organic layers were dried (MgSO$_4$), filtered and concentrated in vacuo. This material was purified by flash chromatography, eluting silica gel with hexane:ethyl acetate (100:0 to 5:1) to give the product. (1.06 g, 85%); $\delta_H$ (300 MHz, CDCl$_3$) 7.06-7.01 (2H, m), 6.78-6.72 (1H, m), 6.37 (1H, s), 5.31 (1H, bs), 2.45 (3H, s).

1-Methyl-1H-indol-5-ol

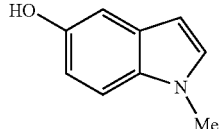

(Ref: Taborsky, R. G.; Delvigs, P; Palaic, D; Bumpus, F. M. J. Med. Chem. (1967), 10(3), 403-7). To a solution of 5-benzyloxy-1-methyl-1H-indole (2 g, 8.9 mmol) in ethanol (20 mL) was added potassium hydroxide (0.62 g, 11.2 mmol). The resulting solution was allowed to stir at room temperature for 10 mins before evaporating the ethanol in vacuo. The residue was taken up in acetone (75 mL) and sodium sulfate (6.4 g, 44.8 mmol) was added, followed by dimethyl sulfate (0.87 mL, 8.9 mmol) via syringe. The solution was stirred for 0.5 h, then filtered and evaporated in vacuo. The resulting residue was then taken up in ethanol (50 mL) and 10% palladium on charcoal (0.4 g) was added. This solution was stirred under a hydrogen atmosphere for 4 h, then filtered through celite and the solvent evaporated in vacuo. This material was purified by flash chromatography, eluting silica gel with hexane:ethyl acetate (100:0 to 50:50) to give the product. (0.48 g, 37%); $\delta_H$ (300 MHz, CDCl$_3$) 7.15 (1H, d, Ar), 7.01 (2H, m, Ar), 6.8 (1H, m, Ar), 6.32 (1H, m, Ar), 3.73 (3H, s, NCH$_3$).

1-Methyl-1H-indol-7-ol a) 7-Benzyloxy-1-methyl-1H-indole

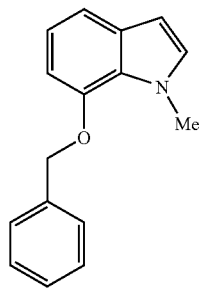

To a solution of 7-benzyloxy-1H-indole (Ref: Dobson, D; Todd, A; Gilmore, J. Synth. Commun. (1991), 21(5), 611-17) (1.29 g, 5.78 mmol) in ethanol (30 mL) was added potassium hydroxide (0.41 g, 7.23 mmol) and dichloromethane (5 mL) of to help solubilize the starting material. The resulting solution was allowed to stir at room temperature for 10 min before evaporating the solvent in vacuo. The residue was taken up in acetone (75 mL) and sodium sulfate (4.9 g, 34.7 mmol) was added followed by dimethyl sulfate via syringe (0.62 mL, 6.3 mmol). The solution was stirred for 1 h, then filtered and evaporated in vacuo. This material was purified by flash chromatography, eluting silica gel with hexane:ethyl acetate (100:0 to 10:1) to give the product. (1.12 g, 82%); Mass spectrum (ion spray): m/z=238.1 (M+1).

b) 1-Methyl-1H-indol-7-ol

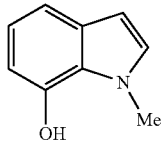

To a solution of 7-benzyloxy-1-methyl-1H-indole in 20 mL of ethanol was added 10% palladium on charcoal (0.2 g). This solution was stirred under balloon pressure hydrogen atmosphere for 4 h, then filtered through celite and concentrated in vacuo. This material was purified by flash chromatography, eluting silica gel with hexane:ethyl acetate (100:0 to 50:50) to give the product (0.58 g, 87%); Mass spectrum (TOF): m/z=147.1 (M).

O-(1-benzothien-4-yl)-dimethylthiocarbamate

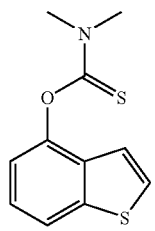

A solution of N,N-dimethylthiocarbamoyl chloride (4.55 g, 36.6 mmol, 1.1 eq) in THF (10 ml) was added to a cooled solution (0° C.) of 4-hydroxybenzothiophene (5 g, 33.2 mmol, 1 eq) and potassium hydroxide (2.05 g, 36.6 mmol, 1.1 eq) in water (25 ml) at a rate such that the temperature did not exceed 10° C. The reaction was stirred at room temperature for 10 minutes then extracted with ethyl acetate (3×50 ml). The combined organic extracts were washed successively with 2N NaOH (50 ml), water (50 ml), 2N HCl (50 ml) and brine (50 ml), then dried (MgSO$_4$) and the solvent removed in vacuo to give the crude product which was purified by flash chromatography in dichloromethane to give 4.33 g, 55% yield of title compound as a colourless solid; $\delta_H$ (300 MHz, CDCl$_3$) 7.81-7.75 (1H, m, ArH), 7.44-7.34 (2H, m, ArH), 7.26-7.23 (1H, m, ArH), 7.08-7.06 (1H, m, ArH), 3.51 (3H, s, N(CH$_3$)$_2$) and 3.44 (3H, s, N(CH$_3$)$_2$).

Similarly prepared was

O-(1-benzothien-7-yl)-dimethylthiocarbamate

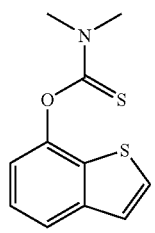

(2.01 g, 42% yield) of title compound; $\delta_H$ (300 MHz, CDCl$_3$) 7.73-7.70 (1H, m, ArH), 7.46-7.34 (3H, m, ArH), 7.13-7.07 (1H, m, ArH) 3.50 (3H, s, N(CH$_3$)$_2$) and 3.44 (3H, s, N(CH$_3$)$_2$).

S-(1-benzothien-4-yl)-dimethylthiocarbamate

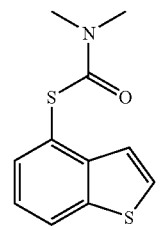

The O-(1-benzothien-4-yl)-dimethylthiocarbamate (2.75 g, 11.6 mmol, 1 eq) was placed in a 50 ml round bottom flask fitted with a reflux condensor and under nitrogen. The vessel was irradiated with focused microwaves at 150 Watt power, to 175° C. for 10 minutes. The product was purified by flash chromatography with a gradient of 0-40% ethyl acetate/isohexane over 25 minutes to give the title compound as a colourless solid 2.33 g, 85% yield; $\delta_H$ (300 MHz, CDCl$_3$) 7.91 (1H, d, J=7.9 Hz, ArH), 7.62-7.48 (3H, m, ArH), 7.36 (1H, t, J=7.9 Hz, ArH), 3.18 (3H, br. s, N(CH$_3$)$_2$) and 3.03 (3H, br. s, N(CH$_3$)$_2$).

S-(1-benzothien-7-yl)-dimethylthiocarbamate

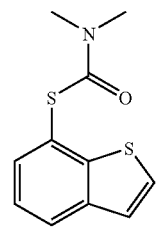

The O-(1-benzothien-7-yl)-dimethylthiocarbamate (2 g, 8.4 mmol, 1 eq) was absorbed onto graphite powder (4 g) and placed in a 50 ml round bottom flask fitted with a reflux condenser and under nitrogen. The vessel was irradiated with focused microwaves at 50-100 Watt power for 45 minutes. The product was washed off the graphite and the solvent removed in vacuo. The crude product was purified by flash chromatography with a gradient of 0-40% ethyl acetate/isohexane to give the title compound as a colorless solid (0.36 g, 18% yield); $\delta_H$ (300 MHz, CDCl$_3$) 7.83 (1H, d, J=7.9 Hz, ArH), 7.50 (1H, d, J=7.4 Hz, ArH), 7.42-7.28 (3H, m, ArH), 3.10 (3H, br. s, N(CH$_3$)$_2$) and 2.98 (3H, br. s, N(CH$_3$)$_2$).

Isoquinolin-4-ol

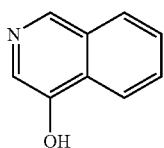

The title compound was prepared as described in *Tetrahedron*, 1963, 19, 827-832.

Isoquinolin-6-ol a) 6-Methoxy-isoquinoline

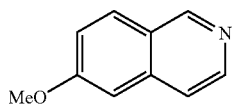

The title compound was prepared as described in *Synth. Commun.*, 1999, 29, 1617-1625.

b) Isoquinolin-6-ol

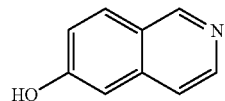

Heat a mixture of 6-methoxy-isoquinoline (2.1 g, 13.2 mmol) and pyridine hydrochloride (30 g) in a heavy walled screw cap sealed tube at 160° C. overnight. Cool to room temperature, add water and concentrated ammonium hydroxide to bring the pH of the mixture to 10-11, extract with ethyl acetate (4 times), wash the combined organic extracts with water (4 times), and concentrate under reduced pressure. Purification by medium pressure liquid chromatography eluting with 0-3% of 2N $NH_3$/MeOH in dichloromethane afford the title compound (520 mg, 27%): $\delta_H$ (DMSO-d6, 400 MHz): 7.09 (s, 1H), 7.19 (dd, 1H, J=9, 2 Hz), 7.56 (d, 1H, J=6 Hz), 7.94 (d, 1H, J=9 Hz), 8.29 (d, 1H, J=6 Hz), 9.05 (s, 1H), 10.36 (s, 1H).

[1.7]Naphthyridin-5-ol

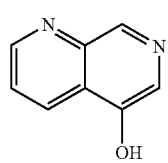

The title compound was prepared as described in *Liebigs Annalen Der Chemie*, 1979, 443-445.

5-Hydroxyisoquinoline

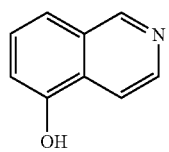

The title compound is commercially available and was purchased from the Aldrich Chemical Company.

5-Quinolinol

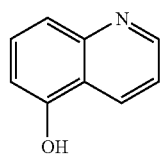

The title compound is commercially available and was purchased from the Aldrich Chemical Company.

Benzo[d]isothiazol-4-ol a) 4-Methoxy-benzo[d]isothiazole

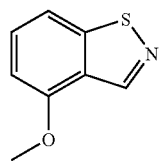

To a solution of 2-fluoro-6-methoxybenzaldehyde (2.0 g, 13.0 mmol) in 2-methoxyethanol (10 mL) in a sealed tube was added sulfur (416 mg, 13.0 mmol) and aqueous ammonium hydroxide (10 mL). The solution was heated to 160 degC for 18 h and was then cooled to rt. The reaction was partitioned between dichloromethane and water. The organic layer was separated and the aqueous layer was extracted with 2×50 mL dichloromethane. The combined organic phases were dried ($MgSO_4$) and concentrated in vacuo. The residue was purified by flash chromatography eluting silica gel with EtOAc:hexane [0:100 to 4:6] to yield the title compound as an oil (1.51 g, 70%); Mass spectrum (ion spray): m/z=165.9 (m+1).

b) Benzo[d]isothiazol-4-ol

To a sealed tube was added 4-methoxy-benzo[d]isothiazole (760 mg, 4.60 mmol) and pyridine hydrochloride (5.5 g, 48 mmol). The reaction was heated to 150° C. for 18 h and was then cooled to rt. The mixture was partitioned between dichloromethane and water. The organic phase was separated and the aqueous layer was extracted with 2×30 mL dichloromethane. The combined organic phases were dried (MgSO$_4$) and concentrated in vacuo. The residue was purified by flash chromatography eluting silica gel with EtOAc:hexane [0:100 to 3:7] to yield the title compound as a solid (223 mg, 32%); Mass spectrum (ion spray): m/z=151.9 (m+1).

7-methyl-benzo[d]isothiazol-4-ol a) 7-Bromo-4-methoxy-benzo[d]isothiazole

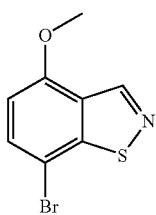

To a solution of 4-methoxy-benzo[d]isothiazole (prepared as described above) (1.0 g, 6.05 mmol) in carbon tetrachloride (20 mL) at 0° C. was added bromine (310 µL, 6.05 mmol) in carbon tetrachloride (10 mL). The reaction was allowed to stir at 0° C. for 3 h and was then warmed to rt. Saturated aqueous NaHCO$_3$ and dichloromethane were added and the organic phase was separated. The aqueous phase was extracted with 2×20 mL dichloromethane. The combined organic phases were dried (MgSO$_4$) and concentrated in vacuo. The residue was purified by flash chromatography eluting silica gel with EtOAc:hexane [0:100 to 1:20] to yield the title compound (980 mg, 66%): δ$_H$ (300 MHz, CDCl$_3$): 9.09 (1H, s), 7.52 (1H, d, J=8.1 Hz), 6.67 (1H, d, J=8.4 Hz), 4.00 (3H, s).

b) 7-methyl-benzo[d]isothiazol-4-ol

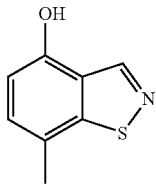

A solution of 7-bromo-4-methoxy-benzo[d]isothiazole (460 mg, 1.88 mmol), K$_2$CO$_3$ (780 mg, 5.64 mmol), and Pd(PPh$_3$)$_4$ (217 mg, 0.188 mmol) in 1,4-dioxane (5 mL) was added trimethylboroxine (290 µL, 2.07 mmol) and the solution was heated to 110° C. for 18 h. The reaction was cooled to rt and diluted with water and dichloromethane. The organic phase was separated and the aqueous phase was extracted with 2×30 mL dichloromethane. The combined organic phases were dried (MgSO$_4$) and concentrated in vacuo. The residue was purified by flash chromatography eluting silica gel with EtOAc:hexane [0:100 to 1:10] to yield 4-methoxy-7-methyl-benzo[d]isothiazole (88 mg, 26%). A method similar to that described for the preparation of benzo[d]isothiazol-4-ol (above) using 4-methoxy-7-methyl-benzo[d]isothiazole (88 mg, 0.491 mmol) and pyridine hydrochloride (567 mg, 5 mol) gave the title compound (30 mg, 37%): δ$_H$ (300 MHz, CDCl$_3$): 8.99 (1H, s), 7.15 (1H, d, J=7.5 Hz), 6.70 (1H, d, J=7.5 Hz), 2.45 (3H, s).

Benzo[d]isothiazol-7-ol a) 2-Fluoro-3,N-dimethoxy-N-methyl-benzamide

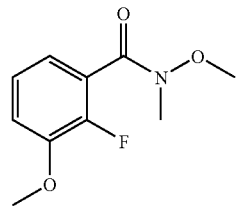

To a solution of 2-fluoro-3-methoxy-benzoic acid (5.0 g, 29.4 mmol) and PyBOP (13.7 g, 29.4 mmol) in 7:1 CH$_2$Cl$_2$:THF was added triethylamine (4.10 mL, 29.4 mmol) over a 10 min period. N,O-Dimethylhydroxylamine hydrochloride (2.87 g, 29.4 mL) was then added and the reaction was allowed to stir at rt for 3 h. The reaction was then partitioned between dichloromethane and water. The organic phase was separated and the aqueous phase was extracted with 2×100 mL dichloromethane. The combined organic phases were dried (MgSO$_4$) and concentrated in vacuo. The residue was taken up in ethyl acetate and was washed successively with 1N HCl, saturated aqueous NaHCO$_3$, and brine. The organic phase was again dried (MgSO$_4$) and concentrated in vacuo to yield the title compound (2.30 g, 37%).

b) 2-Fluoro-3-methoxy-benzaldehyde

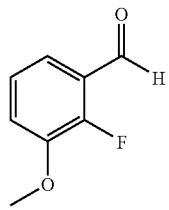

To a solution of 2-fluoro-3,N-dimethoxy-N-methyl-benzamide (2.30 g, 10.8 mmol) in THF (20 mL) at −78° C. was added 1M DIBAL-H in toluene (12 mL, 12 mmol). The reaction stirred at −78° C. for 3 h and then the remaining 1M DIBAL H in toluene (4.2 mL, 4.2 mmol) was added to the reaction. The reaction was allowed to stir at −78° C. for 30 min and was then warmed to rt. The reaction was quenched slowly with saturated aqueous NH$_4$Cl. The organic phase was separated and the aqueous phase was extracted with 2×50 mL ethyl acetate. The combined organic phases were washed successively with 1N HCl and brine. The organic phase was dried (MgSO$_4$) and concentrated in vacuo. The residue was purified by flash chromatography eluting silica gel with EtOAc:hexane [0:100 to 1:1] to yield the title compound (1.41 g, 85%): δ$_H$ (300 MHz, CDCl$_3$): 10.38 (1H, s), 7.43-7.40 (1H, m), 7.24-7.15 (2H, m), 3.95 (3H, s).

c) 7-methoxy-benzo[d]isothiazole

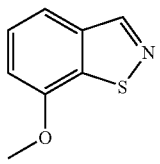

A method similar to 4-methoxy-benzo[d]isothiazole using 2-fluoro-3-methoxy-benzaldehyde (410 mg, 2.66 mmol), sulfur (85 mg, 2.66 mmol), NH$_4$OH (5 mL), and 2-methoxyethanol (5 mL) gave the title compound (60 mg, 14%); Mass spectrum (ion-spray): m/z=165.8 (m+1).

d) Benzo[d]isothiazol-7-ol

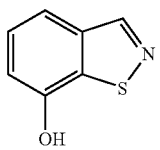

A method similar to that used in the preparation of benzo[d]isothiazol-4-ol using 7-methoxy-benzo[d]isothiazole (60 mg, 0.363 mmol) and pyridine hydrochloride (500 mg, 4.33 mmol) gave the title compound (26 mg, 47%); Mass spectrum (ion-spray): m/z=151.9 (m+1).

4-Hydroxy-benzothiazole a) 4-Methoxy-benzothiazole

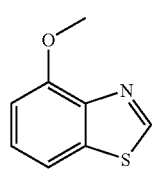

2-Amino-4-methoxy-benzothiazole (1.00 g, 5.54 mmol) was added to a stirred solution of polyphosphoric acid (85%, 40 ml) at 60° C. The resulting mixture was stirred at 60° C. until all the benzothiazole had dissolved. The resulting solution was then cooled to −10° C. and a solution of sodium nitrite (2.3 g, 33.3 mmol) in water (5 ml) was added so as to keep the internal temperature below −4° C. After complete addition the resulting solution was added to a solution of hypophosphoric acid (50%, 15 ml) at 0° C. After the evolution of gas had ceased the mixture was diluted with water and basified with NaHCO$_3$ (sat). The aqueous solution was extracted with CHCl$_3$ (3×200 ml) with the combined organic extracts dried (MgSO$_4$) and the solvent removed in vacuo. The resulting solid was recrystallised from EtOH:H$_2$O to give an orange solid (300 mg).

The liquor was concentrated and purified by flash chromatography eluting silica gel with hexane:EtOAc [4:1] to hexane:EtOAc [1:1] to give a further 210 mg of product. R$_f$=0.38 in hexane:ether [1:1]; δ$_H$ (300 MHz, CDCl$_3$) 8.91 (1H, s, CH), 7.53 (1H, d, Ar), 7.39 (1H, t, Ar), 6.93 (1H, d, Ar), 4.07 (3H, s, OCH$_3$).

b) 4-Hydroxy-benzothiazole

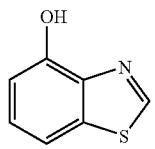

Boron tribromide (3.09 ml, 1M solution in DCM, 3.09 mmol) was added dropwise at 0° C. to a stirred solution of 4-methoxy-benzothiazole (510 mg, 3.09 mmol) in dry DCM (30 ml). The resulting solution was warmed to 40° C. and allowed to stir overnight. The resulting solution was concentrated in vacuo and diluted with water and HCl (2N). The aqueous phase was neutralised to pH ~7 with NaHCO$_3$ and the solution extracted with EtOAc (3×100 ml) and the combined organic extracts dried (MgSO$_4$) and the solvent removed in vacuo. The resulting oil was purified by flash chromatography eluting silica gel with hexane:EtOAc [4:1] to hexane:EtOAc [7:3] to give the title compound as a tan solid (730 mg, 80%); δ$_H$ (300 MHz, CDCl$_3$) 7.59 (1H, s, CH), 7.46 (1H, dd, Ar), 7.36 (1H, t, Ar), 7.02 (1H, dd, Ar).

Thieno[3,2-c]pyridin-7-ol

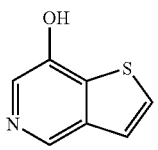

The title compound was prepared as described in Patent GB 2010249A.

Thieno[2,3-c]pyridin-4-ol

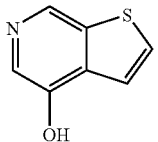

The title compound was prepared as described in Patent GB 2010249A.

4-Fluoro-2,3-dihydrobenzo[b]thiophen-7-ol a) 5-(2-Fluoro-5-methoxybenzylidene)-2-thioxo-1,3-thiazolidin-4-one

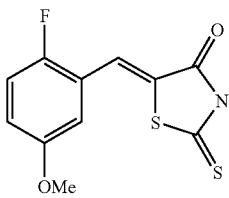

To a suspension of 2-fluoro-5-methoxybenzaldehyde (5.00 g, 32.46 mmol) and rhodanine (4.31 g, 32.46 mmol) in dry toluene (1000 mL) was added ammonium acetate (50 mg) and acetic acid (2 mL). The resulting suspension was allowed to stir at 120° C. for 12 h under Dean-Stark apparatus before being allowed to cool and filtered. Resultant solid was washed with hexane and allowed to dry in vacuo to give an orange crystalline solid (8.00 g, 91%); $\delta_H$ (300 MHz, CDCl$_3$) 7.50 (1H, s, CH=C); 7.31 (1H, t, Ar), 7.20-7.11 (1H, m, Ar), 6.95-6.89 (1H, m, Ar), 3.80 (3H, s, OCH$_3$).

b) (2Z)-3-(2-Fluoro-5-methoxyphenyl)-2-mercapto-2-propenoic acid

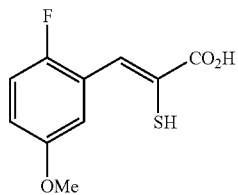

5-(2-Fluoro-5-methoxybenzylidene)-2-thioxo-1,3-thiazolidin-4-one (8.00 g, 9.7 mmol) was added in one portion to 25% w/v sodium hydroxide solution (40 mL). This was allowed stir at reflux for 1 h. After this time the reaction was allowed to cool to room temperature and poured onto water (50 mL). This was washed with dichloromethane (50 mL), and the aqueous layer acidified to pH 2 with aqueous hydrochloric acid (2 N, 50 mL) to give a white suspension. Product was extracted with ether (2×60 mL), dried (MgSO$_4$) and solvent removed in vacuo to give a white solid (6.71 g, 100%); $\delta_H$ (300 MHz, CD$_3$OD) 7.85 (1H, s, Ar), 7.46-7.35 (1H, m, Ar), 7.11 (1H, t, Ar), 7.01-6.75 (2H, m, CH=, and SH), 3.80 (3H, s, OCH$_3$).

c) 4-Fluoro-7-methoxy-1-benzothiophene-2-carboxylic acid

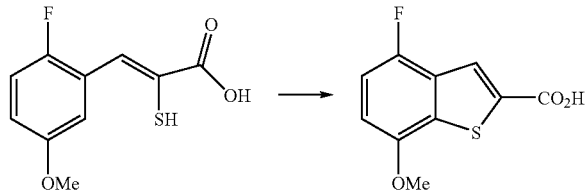

(2Z)-3-(2-Fluoro-5-methoxyphenyl)-2-mercapto-2-propenoic acid (1.00 g, 4.38 mmol) was added in one portion to a solution of iodine (1.66 g, 6.56 mmol) in dimethoxyethane (10 mL). This was heated in the microwave with 300 W at 160° C. for 10 mins. After this time the reaction was allowed to cool to room temperature and poured onto saturated sodium metabisulphite (200 mL) and ether (400 mL). Ether layer was separated and product extracted with aqueous sodium hydroxide (2 N, 2×100 mL). This was then acidified to pH 2 with aqueous hydrochloric acid (2 N, 250 mL), and product extracted with ether (2×150 mL). The combined organic extracts were dried (MgSO$_4$) and concentrated in vacuo to give a white solid (580 mg, 30%); $\delta_H$ (300 MHz, CD$_3$OD) 8.00 (1H, s, Ar), 7.30-7.19 (1H, m, Ar), 7.10-7.00 (1H, m, Ar), 3.95 (3H, s, OCH$_3$).

d) 4-Fluoro-7-methoxy-1-benzothiophene

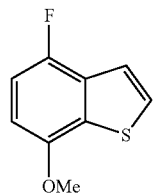

4-Fluoro-7-methoxy-1-benzothiophene-2-carboxylic acid (2.00 g, 8.84 mmol) was added in one portion to DBU (8 mL) and dimethyl acetamide (10 mL). This was heated in the microwave with 300 W at 200° C. for 1 h. The reaction mixture was allowed to cool and poured onto water (100 mL). Product was extracted with hexane (2×100 mL), washed with aqueous hydrochloric acid (2 N, 50 mL), aqueous sodium hydroxide (2 N, 50 mL), and the combined organic extracts were dried (MgSO$_4$) and concentrated in vacuo. The residue was purified by flash chromatography eluting silica gel with hexane:ethyl acetate [96:4] to give an oil (1.12 g, 70%): $\delta_H$ (300 MHz, CDCl$_3$) 7.4 (2H, s, Ar), 6.9 (1H, t, Ar), 6.60 (1H, dd, Ar), 3.91 (3H, s, OCH$_3$).

e) 4-Fluoro-7-methoxy-2,3-dihydrobenzo[b]thiophene

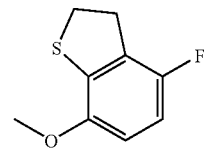

To a solution of 4-fluoro-7-methoxy-1-benzothiophene (1.55 g, 8.5 mmol, 1 eq) in trifluoroacetic acid (40 ml) was added triethylsilane (3.40 ml, 21.25 mmol, 2.5 eq). The mixture was heated to 60° C. for 48 hours, then cooled to room temperature and the solvent removed in vacuo. The crude product was purified by flash chromatography with a gradient of 40-60% chloroform in heptane to give 1.24 g, 80% recovered starting material and 199 mg, 13% yield of the title compound as a colourless oil: $\delta_H$ (300 MHz, CDCl$_3$) 3.78-6.58 (2H, m, ArH), 3.82 (3H, s, CH$_3$) and 3.44-3.30 (4H, m, SCH$_2$CH$_2$).

f) 4-Fluoro-2,3-dihydrobenzo[b]thiophen-7-ol

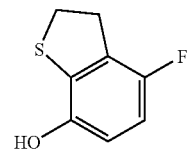

A BBr3 demethylation of 4-fluoro-7-methoxy-2,3-dihydrobenzo[b]thiophene similar to that described for 4-hydroxy benzothiazole affords the title compound as a brown solid 251 mg: $\delta_H$ (300 MHz, CDCl$_3$) 6.57-6.48 (2H, m, ArH), 4.67 (1H, br. s, OH) and 3.43-3.23 (4H, m, SCH$_2$CH$_2$).

(2)-3-(3-Fluoro-phenyl)-prop-2-en-1-ol

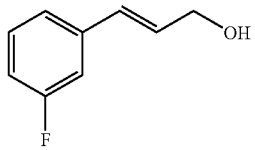

Add lithium hydroxide monohydrate (6.89 g, 164 mmol, 1.1 equiv.) to a stirred solution of (E)-3-fluoro-cinnamic acid (24.8 g, 149 mmol, 1 equiv, commercially available from the Aldrich Chemical Company) in THF (600 mL) and then heat at reflux for 30 minutes to give a thick, colorless slurry. Cool the reaction mixture slightly and add neat dimethyl sulfate (15.8 mL, 167 mmol, 1.1 equiv.) and heat at reflux to give a homogeneous pale yellow solution. Heat the reaction mixture at 60° C. overnight, cool to 0° C. and add sodium hydride (60% in oil, ~13 g, ~325 mmol, ~2.1 equiv.). Add diisobutyl aluminum hydride (1M in dichloromethane, 800 mL, 800 mmol, ~5 equiv.) over 30-45 minutes and stir at 0° C. for 1 hr. Pour the reaction mixture into a 4 l Erlenmeyer flask, add dry ice to the reaction mixture to keep it cool, and then slowly add 5N HCl and more dry ice to keep the quenching under control. Once the initial quench of excess Dibal-H is complete add more 5N HCl and conc. HCl and stir vigorously to give two homogeneous layers. Separate the layers, extract the aqueous layer with dichloromethane (3 times), dry the combined organic extracts over anhydrous magnesium sulfate, filter, and concentrate under reduced pressure. The crude oil thus obtained is purified via medium pressure liquid chromatography eluting with 50% to 100% dichloromethane in hexanes to afford the title compound as a pale yellow oil (9.29 g, 41%); $\delta_H$ (CDCl$_3$, 400 MHz): 4.33 (dd, 2H, J=5, 2 Hz), 6.36 (ddd, 1H, J=16, 5, 5 Hz), 6.59 (d, 1H, J=16 Hz), 6.93 (dddd, 1H, J=8, 8, 2, 0.4 Hz), 7.07 (ddd, 1H, J=10, 2, 2 Hz), 7.13 (d, 1H, J=8 Hz), 7.27 (ddd, 1H, J=8, 8, 6 Hz).

(2R,3R)-[3-(3-Fluoro-phenyl)-oxiranyl]-methanol

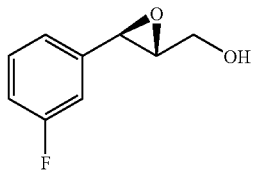

Add neat titanium(IV)tetraisopropoxide to a cold (−20° C.) stirred solution of (−)-diethyl tartrate (330 mg, 1.60 mmol, 0.12 equiv.) and crushed, dried 4A molecular sieves (6.6 g) in dichloromethane (112 mL) and stir at −20° C. for 15 minutes. Add a solution of (E)-3-(3-fluoro-phenyl)-prop-2-en-1-ol (2.01 g, 13.21 mmol, 1 equiv.) via canula using dichloromethane (20 mL) and stir at −20° C. for 25 minutes. Add a cold (−20° C.) dried solution of tert-butylhydroperoxide in dichloromethane (6.6 mL, ~5M in CH$_2$Cl$_2$, ~33 mmol, ~2.5 equiv.) and stir at −20° C. for 5 hr. Add neat dimethyl sulfide (7 mL), stir at −20° C. for 1 hr and then add a 30% (w/v) solution of sodium hydroxide in brine (1.6 mL) and stir for 30 minutes while warming to room temperature. Add diethyl ether (7 mL), Celite (4 g), and magnesium sulfate (4 g) and stir at room temperature for 30 minutes before filtering the reaction mixture through Celite and eluting with dichloromethane. The filtrate is concentrated under reduced pressure to afford a crude oil which is purified by medium pressure liquid chromatography eluting with 10-20% ethyl acetate in 80-90% hexanes to afford the title compound as a colorless oil (1.654 g, 74%) Chiral HPLC analysis indicates 94.7% ee; $\delta_H$ (CDCl$_3$, 400 MHz): 1.84 (dd, 1H, J=8, 6 Hz), 3.05-3.10 (m, 1H), 3.81 (ddd, 1H, J=13, 8, 4 Hz), 3.93 (d, 1H, J=3 Hz), 4.00-4.09 (m, 1H), 6.95-7.03 (m, 2H), 7.08 (d, 1H, J=8 Hz), 7.31 (ddd, 1H, J=8, 8, 6 Hz).

Prepared similarly was (2S,3S)-[3-(3-Fluoro-phenyl)-oxiranyl]-methanol

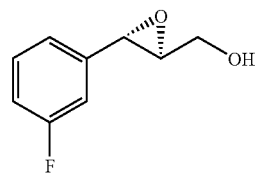

substituting (+)-diethyl tartrate for (−)-diethyl tartrate to afford the title compound as a pale yellow oil (907 mg, 81%). Chiral HPLC indicates 94.5% ee. $\delta_H$ (CDCl$_3$, 400 MHz): 1.84 (dd, 1H, J=8, 6 Hz), 3.05-3.10 (m, 1H), 3.81 (ddd, 1H, J=13, 8, 4 Hz), 3.93 (d, 1H, J=3 Hz), 4.00-4.09 (m, 1H), 6.95-7.03 (m, 2H), 7.08 (d, 1H, J=8 Hz), 7.31 (ddd, 1H, J=8, 8, 6 Hz).

(2R,3S)-3-(Naphthalen-1-yloxy)-3-phenyl-propane-1,2-diol

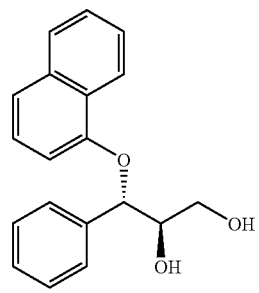

To a solution of (2R,3R)-3-phenylglycidol (5 g, 33 mmol) in 50 mL of 1:1 THF:water, was added 1-naphthol (5.3 g, 37 mmol) and 25 mL of 1 N NaOH. The resulting solution was heated at 75° C. for 4 h, then cooled to room temperature and allowed to stir overnight. The solution was diluted with ethyl acetate and water. The layers were separated and the aqueous phase was further extracted 2 times with CH$_2$Cl$_2$. The combined organic phase was dried (MgSO$_4$) and concentrated in vacuo. The residue was purified by flash chromatography eluting silica gel with hexane:ethyl acetate [100:0 to 1:1] to yield the title compound (6.37 g, 66%); $\delta_H$ (300 MHz, DMSO): 8.43 (1H, m), 7.83 (1H, m), 7.57-7.21 (9H, m), 6.72 (1H, d, J=7.65 h), 5.47 (1H, d, J=5.12), 5.06 (1H, d, J=5.49), 4.69 (1H, t, J=5.49), 4.03 (1H, m), 3.55 (2H, m).

Similarly prepared were (2R,3S)-3-(Benzo[b]thiophen-4-yloxy)-3-phenyl-propane-1,2-diol

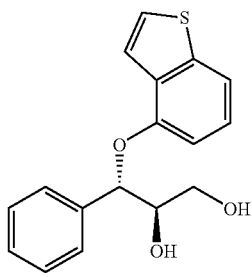

(897 mg, 44%) as a colorless foam; $\delta_H$ (CDCl$_3$, 400 MHz): 2.24 (Or s, 2H), 3.91 (d, 2H, J=4, 4 Hz), 4.09 (ddd, 1H, J=6, 4, 4 Hz), 5.36 (d, 1H, J=6 Hz), 6.55 (d, 1H, J=8 Hz), 7.08 (dd, 1H, J=8, 8 Hz), 7.25-7.47 (m, 7H), 7.59 (d, 1H, J=6 Hz).

(2R,3S)-3-(7-Fluoro-benzo[b]thiophen-4-yloxy)-3-phenyl-propane-1,2-diol

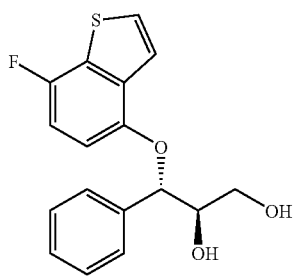

(710 mg, 75%) of the title compound; $\delta_H$ (300 MHz, CDCl$_3$): 7.59-7.56 (1H, m), 7.43-7.31 (6H, m), 6.76 (1H, t, J=8.8), 6.47 (1H, dd, J=3.7, 8.8), 5.30 (1H, d, J=6.2), 4.10-4.05 (1H, m), 3.93-3.90 (2H, m), 1.91 (2H, bs).

(2R,3S)-3-(2-Methyl-benzofuran-7-yloxy)-3-phenyl-propane-1,2-diol

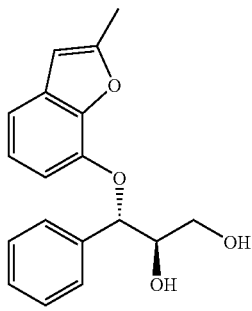

(0.718 g, 52%) of the title compound; Mass spectrum (FAB): m/z=299.1 (m+1).

(2R,3S)-3-(Benzofuran-7-yloxy)-3-phenyl-propane-1,2-diol

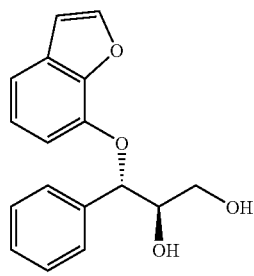

(1.24 g, 63%) of the title compound; $\delta_H$ (300 MHz, CDCl$_3$): 7.63 (1H, s), 7.55-7.21 (5H, m), 7.19-7.12 (1H, m), 6.96 (1H, t), 6.86 (1H, s), 6.81 (1H, d), 5.44 (1H, d), 4.15-3.81 (3H, m).

(2R, 3S)-3-Benzo[d]isothiazol-4-yloxy-3-phenyl-propane-1,2-diol

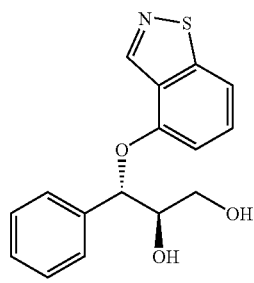

(400 mg, 52%) of the title compound; Mass spectrum (ion spray): m/z=302.0 (m+1).

(2R,3S)-3-(Benzo[b]thiophen-7-yloxy)-3-phenyl-propane-1,2-diol

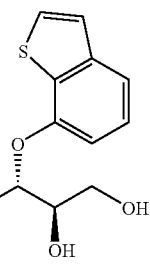

(341 mg, 42%) as a colorless sticky oil. $\delta_H$ (CDCl$_3$, 400 MHz): 2.91 br s, 2H), 3.89 (d, 2H, J=4 Hz), 4.04 (ddd, 1H, J=6, 4, 4 Hz), 5.37 (d, 1H, J=6 Hz), 6.57 (d, 1H, J=8 Hz), 7.12 (dd, 1H, J=8, 8 Hz), 7.25-7.36 (m, 3H), 7.37-7.45 (m, 4H).

(2R,3S)-3-(2-Fluoro-benzo[b]thioiphen-4-yloxy)-3-phenyl-propane-1,2-diol

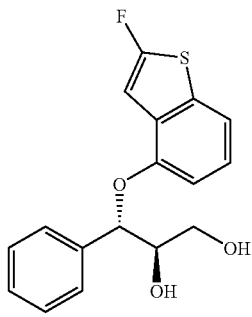

δ$_H$ (MeOH): 7.60 (1H, d), 7.30 (2H, m), 7.20 (6H, m), 6.60 (1H, d), 5.30 (1H, d), 4.20 (1H, m), 3.50 (1H, m), 3.20 (4H, m), 2.80 (2H, br s).
prepared similarly using (2S,3S)-3-phenylglycidol instead of (2R,3R)-3-phenylglycidol (2S,3R)-3-(Naphthalen-1-yloxy)-3-phenyl-propane-1,2-diol

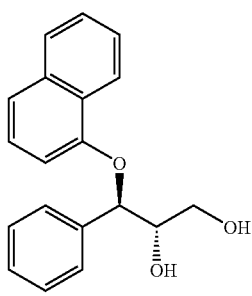

(13.8 g, 70%) of the title compound; δ$_H$ (300 MHz, DMSO): 8.43 (1H, m), 7.83 (1H, m), 7.57-7.21 (9H, m), 6.72 (1H, d, J=7.65 h), 5.47 (1H, d, J=5.12), 5.06 (1H, d, J=5.49), 4.69 (1H, t, J=5.49), 4.03 (1H, m), 3.55 (2H, m).

(2S,3R)-(Benzo[b]thiophen-4-yloxy)-3-phenyl-propane-1,2-diol

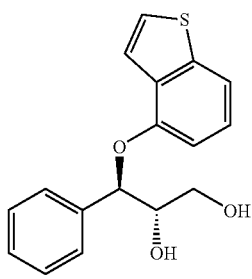

(1.16 g, 39%) as a colorless foam; δ$_H$ (CDCl$_3$, 400 MHz): 2.24 (br s, 2H), 3.91 (d, 2H, J=4 Hz), 4.09 (ddd, 1H, J=6, 4, 4 Hz), 5.36 (d, 1H, J=6 Hz), 6.55 (d, 1H, J=8 Hz), 7.08 (dd, 1H, J=8, 8 Hz), 7.25-7.47 (m, 71), 7.59 (d, 1H, J=6 Hz).

(2R, 3S)-3-Benzo[d]isothiazol-4-yloxy-3-phenyl-propane-1,2-diol

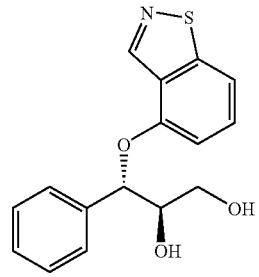

(386 mg, 2.55 mmol) of the title compound (400 mg, 52%); Mass spectrum (ion spray): m/z=302.0 (m+1).

(2S, 3R)-3-Benzo[d]isothiazol-4-yloxy-3-phenyl-propane-1,2-diol

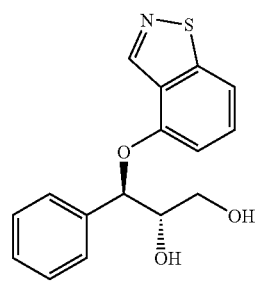

(400 mg, 48%) of the title compound; Mass spectrum (ion spray): m/z 302.0 (m+1).

(2S,3R)-3-(Benzo[b]thiophen-7-yloxy)-3-Phenyl-propane-1,2-diol

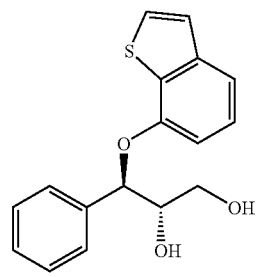

(269 mg, 33%) as a sticky oil; δ$_H$ (CDCl$_3$, 400 z): 2.91 (br s, 2H), 3.89 (d, 2H, J=4 Hz), 4.04 (ddd, 1H, J=6, 4, 4 Hz), 5.37 (d, 1H, J=6 Hz), 6.57 (d, 1H, J=8 Hz), 7.12 (dd, 1H, J=8, 8 Hz), 7.25-7.36 (m, 3H), 7.37-7.45 (m, 4H).

Prepared similarly using (2R,3R)-[3-(3-fluoro-phenyl)-oxiranyl]-methanol 2R,3S)-3-(Benzo[b]thiophen-4-yloxy)-3-(3-fluoro-phenyl)-propane-1,2-diol

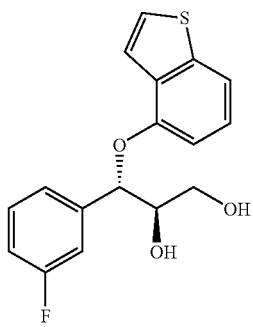

(423 mg, 50%) as a colorless sticky oil; δ$_H$ (CDCl$_3$, 400 MHz): 3.06 (br s, 2H), 3.84 (d, 2H, J=4 Hz), 4.01 (ddd, 1H, J=6, 4, 4 Hz), 5.27 (d, 1H, J=6 Hz), 6.51 (d, 1H, J=8 Hz), 6.97 (ddd, 1H, J=8, 2, 2 Hz), 7.08 (dd, 1H, J=8, 8 Hz), 7.11-7.19 (m, 2H), 7.27 (ddd, 1H, J=8, 8, 6 Hz), 7.43 (d, 1H, J=7 Hz), 7.57 (d, 1H, J=6 Hz).

(2R,3S)-3-(4-Fluoro-naphthalen-1-yloxy)-3-(3-fluoro-phenyl)-propane-1,2-diol

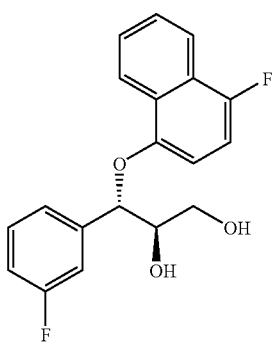

(1.30 g, 71%); (CDCl$_3$, 400 MHz): 2.07 (br s, 1H), 2.35 (br d, 1H, J=4 Hz), 3.96 (br s, 2H), 4.10-4.20 (m, 1H), 5.34 (d, 1H, J=7 Hz), 6.48 (dd, 1H, J=8, 4 Hz), 6.85 (dd, 1H, J=10, 8 Hz), 7.03 (ddd, 1H, J=8, 8, 2 Hz), 7.18 (ddd, 1H, J=10, 2, 2 Hz), 7.22 (d, 1H, J=8 Hz), 7.33 (ddd, 1H, J=8, 8, 6 Hz), 7.55-7.63 (m, 2H), 8.00-8.07 (m, 1H), 8.27-8.33 (m, 1H).

(2R,3S)-3-(5-Fluoro-benzo[b]thiophen-4-yloxy-3-(3-fluoro-phenyl)-propane-1,2-diol

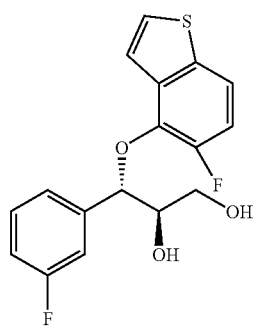

(4.24 g, 57%) as a sticky colorless oil; (CDCl$_3$, 400 MHz): 2.00-2.35 (br m, 2H), 3.88-3.97 (m, 2H), 4.18-4.23 (m, 1H), 5.40 (d, 1H, J=6 Hz), 6.96-7.02 (m, 1H), 7.04 (dd, 1H, J=11, 8 Hz) 7.17-7.22 (m, 2H), 7.26-7.32 (m, 1H), 7.36-7.45 (m, 3H).

Prepared similarly using (2S,3S)-[3-(3-fluoro-phenyl)-oxiranyl]-methanol (2S,3R)-3-(Benzo[b]thiophen-4-yloxy)-3-(3-fluoro-phenyl)-propane-1,2-diol

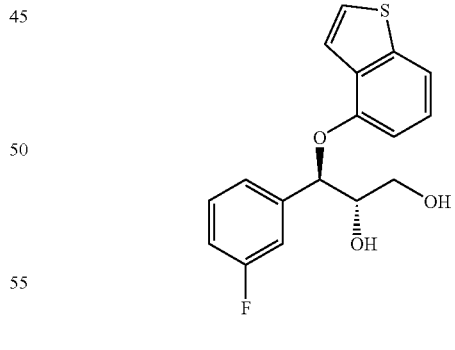

(490 mg, 58%) as a sticky colorless oil; (CDCl$_3$, 400 MHz): 3.06 (br s, 2H), 3.84 (d, 2H, J=4 Hz), 4.01 (ddd, 1H, J=6, 4, 4 Hz), 5.27 (d, 1H, J=6 Hz), 6.51 (d, 1H, J=8 Hz), 6.97 (ddd, 1H, J=8, 2, 2 Hz), 7.08 (dd, 1H, j=8, 8 Hz), 7.11-7.19 (m, 2H), 7.27 (ddd, 1H, J=8, 8, 6 Hz), 7.43 (d, 1H, J=7 Hz), 7.57 (d, 1H, J=6 Hz).

(2S, 3R)-3-(Benzo[b]thiophen-4-ylsulfanyl)-3-phenyl-propane-1,2-diol

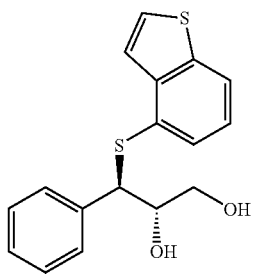

To a stirred solution of S-(1-benzothieny-4-yl)-dimethylthiocarbamate (500 mg, 2.1 mmol, 1 eq) in THF (5 ml) was added potassium hydroxide (237 mg, 4.2 mmol, 2 eq) in methanol (1 ml). The mixture was degassed by bubbling with nitrogen. After 16 hours at room temperature the mixture was poured onto crushed ice and acidified to pH 2 with 2N hydrochloric acid. The aqueous layer was extracted with ethyl acetate (3×50 ml), and the combined organics washed with water (50 ml) and brine (50 ml), then dried (MgSO$_4$) and the solvent removed in vacuo to give 355 mg, 100% which was used without further purification in the next step.

To a stirred solution of the thiol (355 mg, 2.1 mmol, 1 eq), triethylamine (0.36 ml, 2.6 mmol, 1.2 eq) in methanol (4 ml) was added S,S-3-phenylglycidol (321 mg, 2.1 mmol, 1 eq), and the mixture stirred at room temperature overnight. The reaction mixture was diluted with ether (20 ml), washed successively with saturated sodium hydrogen carbonate (20 ml), 2M hydrochloric acid (20 ml), water (20 ml), brine (20 ml) then dried (MgSO$_4$) and the solvent removed in vacuo. The crude compound was purified by flash chromatography with a gradient of 20-50% ethyl acetate in iso-hexane to give the title compound as a colourless solid, 236 mg, 35% yield. δ$_H$ (300 MHz, CDCl$_3$) 7.83-7.75 (1H, m, ArH), 7.55-7.53 (1H, m, ArH), 7.46-7.44 (1H, m, ArH), 7.30-7.17 (7H, m, ArH), 4.31 (1H, d, J=6.9 Hz, CHS), 4.10-4.04 (1H, m, CHOH), 3.84-3.77 (1H, m, CHHOH) and 3.69-3.63 (1H, m, CHHOH), 2.52 (1H, br. s, OH) and 2.16 (1H, br. s, OH).

Prepared similarly using (R,R)-3-phenylglycidol (2R, 3S)-3-(Benzo[b]thiophen-4-ylsulfanyl-3-phenyl-propane-1,2-diol

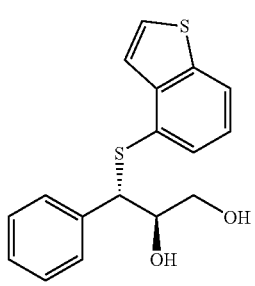

(76 mg) of the title compound; δ$_H$ (300 MHz, CDCl$_3$) 7.83-7.75 (1H, m, ArH), 7.55-7.53 (1H, m, ArH), 7.46-7.44 (1H, m, ArH), 7.30-7.17 (7H, m, ArH), 4.31 (1H, d, J=6.9 Hz, CHS), 4.10-4.04 (1H, m, CHOH), 3.84-3.77 (1H, m, CHHOH) and 3.69-3.63 (1H, m, CHHOH), 2.52 (1H, br. s, OH) and 2.16 (1H, br. s, OR).

(2R, 3S)-3-(2-Chloro-phenylsulfanyl)-3-phenyl-propane-1,2-diol

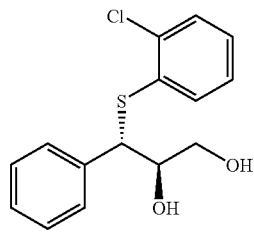

(R,R)-3-Phenylglycidol (0.5 g, 3.3 mmol), triethylamine (0.39 g, 3.3 mmol) and 2-chlorothiophenol (0.47, 3.3 mmol) were dissolved in methanol (5 ml). The reaction mixture was then stirred under nitrogen for 16. The reaction was diluted with ether, washed with diethyl ether followed by sodium hydrogen carbonate, 2M HCl and brine. The combined organics were dried over magnesium sulfate and evaporated in vacuo. The title compound (0.686 g, 70%) was isolated after column chromatography (ISCO system) eluting with 0-50% Ethyl acetate:Hexane ramp over 40 mins. δ$_H$(CDCl$_3$) δ=7.35 (7H, m), 7.15 (2H, m), 4.5 (1H, d), 3.7 (1H, m), 3.7 (1H, m), 2.3 (1H, m), 1.9 (1H, m).

Prepared similarly was (2S, 3R)-3-(2-Chloro-phenylsulfanyl)-3-phenyl-propane-1,2-diol

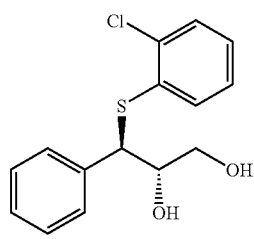

using (S,S)-3-phenylglycidol instead of (R,R)-3-phenylglycidol. δ$_H$(CDCl3) δ=7.35 (7H, m), 7.15 (2H, m), 4.5 (1H, d), 3.7 (1H, m), 3.7 (1H, m), 2.3 (1H, m), 1.9 (1H, m).

(2S)-2-[(S)-(Benzo[b]thiophen-7-yloxy)-phenyl-methyl]-oxirane,

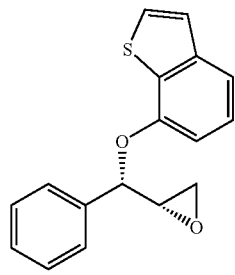

Add 4,4-(dimethyl-1,1-dioxido-1,2,5-thiadiazolidin-2-yl)-triphenyl phosphonium (530 mg, 1.29 mmol, 1.2 equiv. Prepared as described in *J. Org. Chem.* 1994, 59, 2289) to a solution of (2S)-oxiranyl-(R)-phenyl-methanol (175 mg, 1.17 mmol, 1.1 equiv. Prepared as described in *Tetrahedron Lett.,* 1986, 41, 4987.) and 7-hydroxy benzothiophene (157 mg, 1.04 mmol, 1 equiv.) in THF (26 mL) and stir at room temperature for 5 days. Add ethyl acetate and brine, separate the layers, and extract the aqueous layer with ethyl acetate. The combined organic extracts are washed with brine, dried over anhydrous magnesium sulfate, filtered, and concentrated under reduced pressure. Purification by medium pressure liquid chromatography eluting with 0-5% ethyl acetate in hexanes affords the title compound as a colorless oil (187 mg, 64%); $\delta_H$ (CDCl$_3$, 400 MHz): 2.81 (dd, 1H, J=5, 2 Hz), 2.88 (dd, 1H, J=5, 5 Hz), 3.52 (ddd, 1H, J=6, 5, 2 Hz), 5.13 (d, 1H, J=6 Hz), 6.66 (d, 1H, J=8 Hz), 7.15 (d, 1H, J=8 Hz), 7.29-7.52 (m, 8H).

Similarly prepared was

(2S)-2-[(S)-(Benzo[b]thiophen-4-yloxy)-phenyl-methyl]-oxirane

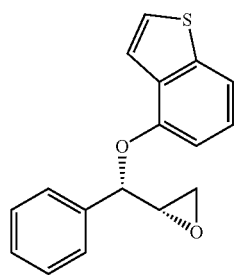

(1.2 g, 64%) of the title compound; $\delta_H$ (CDCl$_3$, 400 MHz): 2.82 (dd, 1H, J=5, 2 Hz), 2.90 (dd, 1H, J=5, 5 Hz), 3.53 (ddd, 1H, J=6, 5, 2 Hz), 5.08 (d, 1H, J=6 Hz), 6.64 (d, 1H, J=8 Hz), 7.12 (d, 1H, J=8 Hz), 7.30-7.50 (m, 7H), 7.69 (d, 1H, J=6 Hz).

Similarly prepared using (2R)-oxiranyl-(S)-phenyl-methanol instead of (2S)-oxiranyl-(R)-phenyl-methanol (Prepared as described in *Tetrahedron Lett,* 1986, 41, 4987.) was

(2R)-2-[(R)-(Benzo[b]thiophen-7-yloxy)-phenyl-methyl]-oxirane

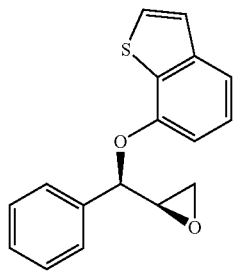

453 mg, 60% ) as a colorless oil; %); $\delta_H$ (CDCl$_3$, 400 MHz): 2.81 (dd, 1H, J=5, 2 Hz), 2.88 (dd, 1H, J=5, 5 Hz), 3.52 (ddd, 1H, J=6, 5, 2 Hz), 5.13 (d, 1H, J=61 Hz), 6.66 (d, 1H, J=8 Hz), 7.15 (d, 1H, J=8 Hz), 7.29-7.52 (m, 8H).

Similarly prepared was

(2R)-2-(R)-(Benzo[b]thiophen-4-yloxy)-phenyl-methyl]-oxirane

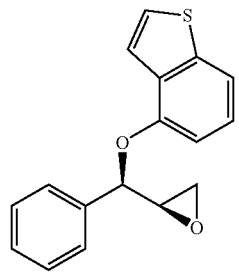

(1.2 g, 59%) of the title compound; $\delta_H$ (CDCl$_3$, 400 MHz): 2.82 (dd, 1H, J=5, 2 Hz), 2.90 (dd, 1H, J=5, 5 Hz), 3.53 (ddd, 1H, J=6, 5, 2 Hz), 5.08 (d, 1H, J=6 Hz), 6.64 (d, 1H, J=8 Hz), 7.12 (d, 1H, J=8 Hz), 7.30-7.50 (m, 7H), 7.69 (d, 1H, J=6 Hz).

(1R,2R)-3-Azido-1-(benzo[b]thiophen-4-yloxy)-1-phenyl-propan-2-ol

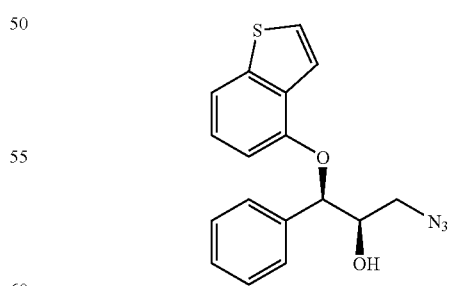

To a solution of (2R)-2-[(R)(Benzo[b]thiophen-4-yloxy)-phenyl-methyl]-oxirane (1.11 g, 3.8 mmol) in 10 mL DMF was added NaN$_3$ (3.7 g, 57 mmol). The resulting solution was heated at 50° C. for 6 h. The solution was diluted with Et$_2$O and water. The layers were separated and the aqueous phase was extracted 2 more times with Et$_2$O. The combined organic phase was dried (MgSO$_4$) and concentrated in vacuo. The residue was purified by flash chromatography eluting silica gel with hexane:ethyl acetate [100:0 to 4:1] to yield the title compound (0.53 g, 42%). $\delta_H$ (300 MHz, CDCl$_3$): 7.62 (1H, d), 7.55-7.22 (7H, m), 7.09 (1H, t), 6.60 (1H, d), 5.39 (1H, d), 4.25-4.18 (1H, m), 3.55-3.45 (1H, m) 3.21-3.12 (1H, m).

Similarly prepared was (1S,2S)-3-Azido-1-(benzo[b]thiophen-4-yloxy)-1-phenyl-propan-2-ol

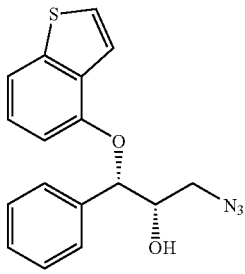

(0.53 g, 42%) of the title compound; $\delta_H$ (300 MHz, DMSO): 7.72 (2H, dd, J=5.49, 24.52), 7.48-7.25 (5H, m), 7.12% (1H, t, J=8.05), 6.67 (1H, d, J=8.05), 5.76 (1H, d, J=5.85), 5.43 (1H, d, J=5.12), 4.08-4.03 (1H, m) 3.29-3.18 (2H, m).

(1S,2R)-3-Azido-1-(naphthalen-1-yloxy)-1-phenyl-propan-2-ol

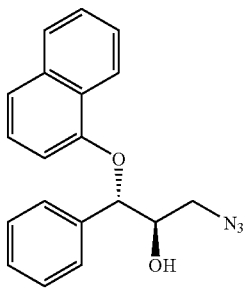

To a solution of (2R,3S)-3-(Naphthalen-1-yloxy)-3-phenyl-propane-1,2-diol (11.18 g, 38 mmol) in 200 mL of CH$_2$Cl$_2$ was added 15 mL of pyridine. This mixture was cooled to −10° C. after which was added mesyl chloride (2.8 mL, 36.1 mmol). The solution was allowed to warm to rt overnight. The reaction was diluted with CH$_2$Cl$_2$ and water. The layers were separated and the aqueous phase was further extracted 2 times with CH$_2$Cl$_2$. The combined organic phase was dried (MgSO$_4$) and concentrated in vacuo. A portion of the residue (7.71 g) was taken up in 80 mL of DMF and to this solution was added NaN$_3$ (21.1 g, 0.32 mol), the resulting solution was heated to 65° C. for 5 h, then cooled to rt and stirred for a further 48 h. The solution was diluted with Et$_2$O and water. The layers were separated and the aqueous phase was extracted 2 more times with Et$_2$O. The combined organic phase was dried (MgSO$_4$) and concentrated in vacuo. The residue was purified by flash chromatography eluting silica gel with hexane:ethyl acetate [100:0 to 3:1] to yield the title compound (4.83 g, 70%); $\delta_H$ (300 MHz, CDCl$_3$): 8.39-8.30 (1H, m) 7.85-7.78 (1H, m), 7.59-7.16 (9H, m), 6.61 (1H, d), 5.39 (1H, d), 4.35-4.21 (1H, m), 3.77-3.62 (2H, m).

Similarly prepared were (1R,2S)-3-Azido-1-(naphthalen-1-yloxy)-1-phenyl-propan-2-ol

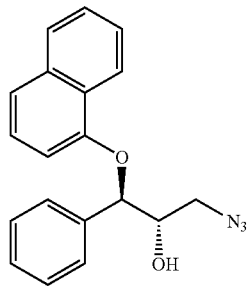

(4.71 g, 67%) of the title compound; $\delta_H$ (300 MHz, CDCl$_3$) 8.39-8.30 (1H, m) 7.85-7.78 (1H, m), 7.59-7.16 (9H, m), 6.61 (1H, d), 5.39 (1H, d), 4.35-4.21 (1H, m), 3.77-3.62 (2H, m).

(2R,3S)-3-Azido-1-(benzofuran-7-yloxy)-1-phenyl-propan-2-ol

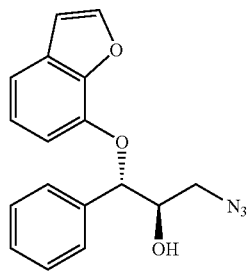

(0.641 g, 74%) of the title compound; $\delta_H$ (300 MHz, CDCl$_3$) 7.63 (1H, d) 7.72-7.24 (5H, m), 7.18 (1H, d), 6.95 (1H, t), 6.75 (1H, d), 6.63 (1H, d), 5.38 (1H, d), 4.24-4.17 (1H, m), 3.77-3.60 (2H, m).

(1R,2S)-3-Azido-1-(benzofuran-7-yloxy)-1-phenyl-propan-2-ol

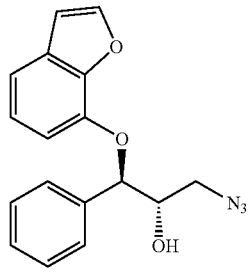

(0.528 g, 79%) of the title compound; $\delta_H$ (300 MHz, DMSO): 7.97 (1H, d, J=2.2), 7.46 (2H, m), 7.35-7.23 (3H, m), 7.14 (1H, d, J=8.05), 6.98 (1H, t, J=8.05), 6.91 (1H, d, J=2.2), 6.74 (1H, d, J=7.69), 5.64 (1H, d, J=6.22), 5.38 (1H, d, J=6.69), 4.10-4.03 (1H, m), 3.53-3.49 (2H, m).

(1S,2R)-3-Azido-1-(2-methyl-benzofuran-7-yloxy)-1-phenyl-propan-2-ol

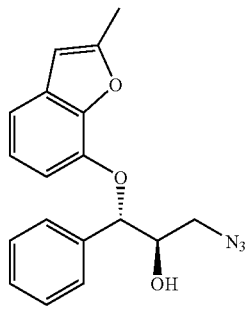

(0.497 g, 70%) of the title compound; Mass spectrum (TOF): m/z=346.1169 (m+23 Na).

(1S,2R)-3-Azido-1-(benzo[b]thiophen-4-yloxy)-1-phenyl-propan-2-ol

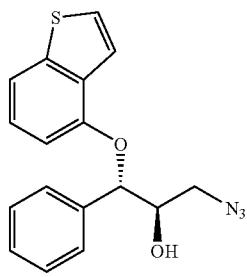

A solution of (2R,3S)-3-(Benzo[b]thiophen-4-yloxy)-3-phenyl-propane-1,2-diol (3.7 g, 12.3 mmol) in 50 mL of pyridine was cooled to −10° C. To this mixture was added tosyl chloride (0.173 mL, 2.23 mmol). The solution was allowed to warm to rt overnight. The reaction was diluted with CH$_2$Cl$_2$ and water. The layers were separated and the aqueous phase was further extracted 2 times with CH$_2$Cl$_2$. The combined organic phase was dried (MgSO$_4$) and concentrated in vacuo. The residue was taken up in 40 mL of DMF and to this solution was added NaN$_3$ (9.3 g, 0.14 mol), the resulting solution was heated to 75° C. for 5 h, then cooled to rt and stirred for a further 24 h. The solution was diluted with Et$_2$O and water. The layers were separated and the aqueous phase was extracted 2 more times with Et$_2$O. The combined organic phase was dried (MgSO$_4$) and concentrated in vacuo. The residue was purified by flash chromatography eluting silica gel with hexane:ethyl acetate [100:0 to 3:1] to yield the title compound (2.55 g, 62%). $\delta_H$ (300 MHz, DMSO): 7.67 (1H, s) 7.48-7.40 (2H, m), 7.34-7.23 (3H, m), 7.12 (1H, t, J=8.05), 6.66 (1H, d, J=8.05), 5.67 (1H, d, J=6.2), 5.37 (1H, d, J=6.57), 4.13-4.09 (1H, m), 3.56-3.44 (2H, m).

(1R,2S)-3-Azido-1-(benzo[b]thiophen-yloxy)-1-phenyl-propan-2-ol

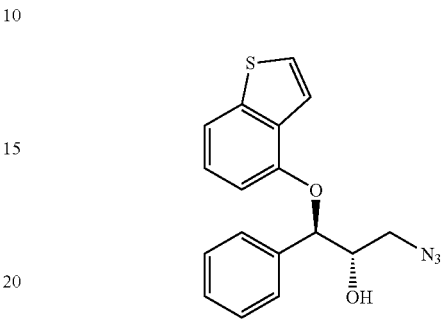

(2.01 g, 82%) of the title compound. $\delta_H$ (300 MHz, CDCl$_3$) 8.02 (1H, s), 7.59 (1H, d), 7.47-7.28 (6H, m), 7.09 (1H, t), 6.56 (1H, d), 5.32 (1H, d), 4.23-4.16 (1H, m), 3.66-3.61 (2H, m).

(2R,3S)-Toluene-4-sulfonic acid 3-(benzo[b]thiophen-4-yloxy)-2-hydroxy-3-phenyl-propyl ester

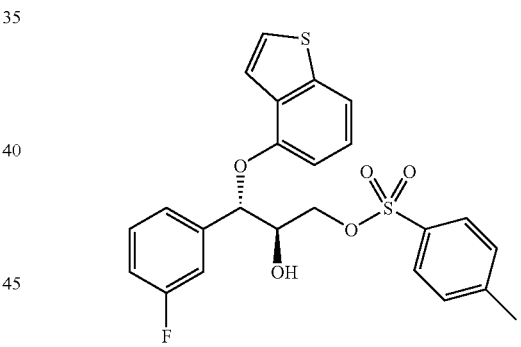

Add p-toluenesulfonyl chloride (2.9 g, 15 mmol, 1.2 equiv.) to a stirred solution of (2R,3S)-3-(benzo[b]thiophen-4-yloxy)-3-(3-fluoro-phenyl)-propane-1,2-diol (4.0 g, 12.5 mmol, 1.0 equiv.) in pyridine (60 ml) and store at 0° C. for 2 days. Add 1 N HCl and ethyl acetate, separate the layers, extract the aqueous layer with ethyl acetate (three times), wash the combined organic extracts over anhydrous sodium sulfate, filter, and concentrate under reduced pressure. Purification by medium pressure liquid chromatography affords the title compound (3.0 g, 51% yield); $\delta_H$ (CDCl$_3$, 400 MHz): 2.15 (s, 3H), 4.03 (ddd, 1H, J=7, 5, 2 Hz), 4.18 (dd, 1H, J=10, 5 Hz), 4.25 (dd, 1H, J=10, 2), 5.27 (d, 1H, J=7 Hz), 6.30 (d, 1H, J=8 Hz), 6.80 (ddd, 1H, J=8, 8, 2 Hz), 6.88-6.98 (m, 4H), 7.01 (d, 1H, J=8 Hz), 7.11 (ddd, 1H, J=8, 8, 6 Hz), 7.19 (d, 1H, J=6 Hz), 7.14-7.36 (m, 2H), 7.51 (d, 2H, J=8 Hz).

Similarly prepared was (2R,3S)-Toluene-4-sulfonic acid 3-(5-fluoro-benzo[b]thiophen-4-yloxy)-3-(3-fluoro-phenyl)-2-hydroxy-propyl ester

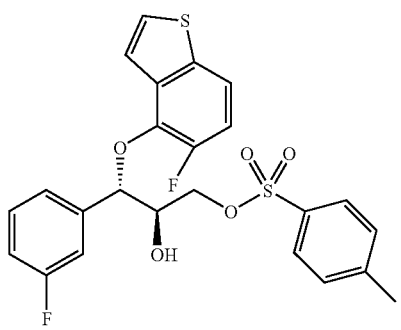

(4.99 g, 84% yield) as a colorless solid; $\delta_H$ (CDCl$_3$, 400 MHz): 2.35 (s, 3H), 2.70-2.91 (br s, 1H), 4.30-4.40 (m, 3H), 5.35-5.42 (m, 1H), 6.87-7.04 (m, 2H), 7.07-7.14 (m, 2H), 7.15-7.26 (m, 3H), 7.27-7.31 (m, 1H), 7.32-7.42 (m, 2H), 7.73-7.80 (m, 2H).

(1R,2S)-3-Azido-1-(benzo[b]thiophen-4-yloxy)-1-phenyl-propan-2-ol

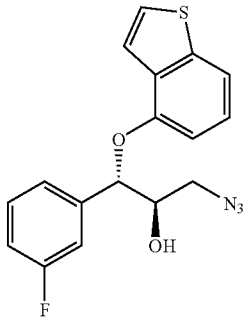

Add sodium azide (6.56 g, 101 mmol, 16 equiv.) to a stirred solution of (2R,3S)-toluene-4-sulfonic acid 3-(benzo[b]thiophen-4-yloxy)-2-hydroxy-3-phenyl-propyl ester (2.98 g, 6.31 mmol, 1 equiv.) in DMF (50 mL) and heat at 85° C. for 5 hr then cool to room temperature and stir at this temperature for 2 days. Add ethyl acetate and water, separate the layers, and extract the aqueous layer with ethyl acetate (3 times). Wash the combined organic extract with brine (twice), dry over anhydrous magnesium sulfate, filter, and concentrate under reduced pressure. Purification by medium pressure liquid chromatography eluting with 0-10% ethyl acetate in hexanes affords the title compound as a colorless solid (1.748 g, 81%); $\delta_H$ (CDCl$_3$, 400 MHz): 2.21 (d, 1H, J=6 Hz), 3.58-3.70 (m, 2H), 4.14-4.22 (m, 1H), 5.31 (d, 1H, J=6 Hz), 6.53 (d, 1H, J=8 Hz), 7.02 (dddd, 1H, J=8, 8, 2, 1 Hz), 7.11 (dd, 1H, J=8, 8 Hz), 7.16 (ddd, 1H, J=10, 2, 2 Hz), 7.23 (d, 1H, J=8 Hz), 7.35 (ddd, 1H, J=8, 8, 6 Hz), 7.42 (d, 1H, J=5 Hz), 7.45 (d, 1H, J=8 Hz), 7.57 (dd, 1H, J=6, 1 Hz).

Similarly prepared was (1R,2S)-3-Azido-1-(5-fluoro-benzo[b]thiophen-4-yloxy)-1-(3-fluoro-phenyl)-propan-2-ol

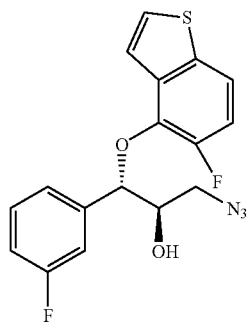

(3.21 g, 84%) as a colorless solid; $\delta_H$ (CDCl$_3$, 400 MHz): 2.17 (d, 1H, J=5 Hz), 3.57-3.68 (m, 2H), 4.25-4.34 (m, 1H), 5.35 (d, 1H, J=7 Hz), 6.97-7.03 (m, 1H), 7.05 (dd, 1H, J=12, 9 Hz), 7.17-7.23 (m, 2H), 7.27-7.35 (m, 2H), 7.40-7.47 (m, 2H).

(1S,2S)-4-(3-Azido-2-fluoro-1-phenyl-propoxy)-benzo[b]thiophene

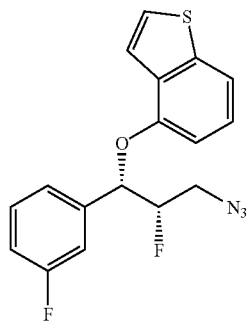

Add neat [bis(2-methoxyethyl)amino]-sulfur trifluoride (Deoxofluor) (0.76 mL, 4.12 mmol, 7 equiv.) to a cold (−78° C.) stirred solution of 4-dimethyl-aminopyridine (DMAP) (217 mg, 1.78 mmol, 3 equiv.) and (1R,2S)-3-azido-1-(benzo[b]thiophen-4-yloxy)-1-phenyl-propan-2-ol (202 mg, 0.588 mmol, 1 equiv.) and gradually allow to warm to room temperature overnight. Carefully add the reaction mixture dropwise into stirred saturated aqueous sodium bicarbonate and stir for 3 hr. Separate the layers, extract the aqueous layer with dichloromethane (three times), dry the combined organic extracts over anhydrous magnesium sulfate, filter, and concentrate under reduced pressure. Purification by medium pressure liquid chromatography eluting with 0-5% ethyl acetate in hexanes affords the title compound as a colorless oil (67.5 mg, 33%); $\delta_H$ (CDCl$_3$, 400 MHz): 3.43 (ddd, 1H, J=22, 14, 6 Hz), 3.60 (ddd, 1H, J=25, 14, 3 Hz), 4.98 (dddd, 1H, J=47, 6, 6, 3 Hz), 5.52 (dd, 1H, J=16, 6 Hz), 6.54 (d, 1H, J=8 Hz), 7.04 (dddd, 1H, J=8, 8, 3, 1 Hz), 7.11 (dd, 1H, J=8, 8 Hz), 7.18 (ddd, 1H, J=9, 2, 2 Hz), 7.25 (d, 1H, J=8 Hz), 7.36 (ddd, 1H, J=8, 8, 6 Hz), 7.41 (d, 1H, J=6 Hz), 7.46 (d, 1H, J=8 Hz), 7.61 (dd, 1H, J=6, 1 Hz).

(1S,2S)-4-[3-Azido-2-fluoro-1-(3-fluoro-phenyl)-propoxy]-5-fluoro-benzo[b]thiophene

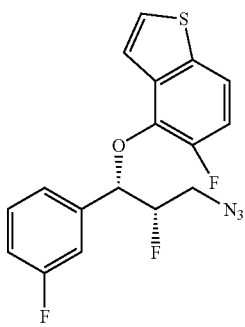

Add a solution of 4-dimethyl-aminopyridine (DMAP) (7 mL/flask, 0.5M in CH$_2$Cl$_2$, 3.5 mmol/flask, 3.2 equiv./flask) to each of seven separate flasks each containing (1R,2S)-3-azido-1-(5-fluoro-benzo[b]thiophen-4-yloxy)-1-(3-fluoro-phenyl)-propan-2-ol (~400 mg/flask for a total of 2.798 g, 7.74 mmol, 1 equiv.). Cool the reaction mixture to −78° C. and add neat [bis(2-methoxyethyl)amino]-sulfur trifluoride (Deoxofluor) (1.4 mL/flask, 7.6 mmol/flask, 10 equiv./flask) and gradually allow to warm to room temperature overnight. Carefully add all seven reaction mixtures dropwise with stirred into the same flask containing saturated aqueous sodium bicarbonate. Separate the layers, extract the aqueous layer with dichloromethane (three times), wash the combined organic extracts with 0.1N HCl until the aqueous layer is basic, dry the organic extracts over anhydrous magnesium sulfate, filter, and concentrate under reduced pressure. Purification by medium pressure liquid chromatography eluting with 0-9% ethyl acetate in hexanes affords the title compound (643 mg, 23%); $\delta_H$ (CDCl$_3$, 400 MHz): 3.35 (ddd, 1H, J=23, 14, 6 Hz), 3.57 (ddd, 1H, J=24, 14, 3 Hz), 5.01 (dddd, 1H, J=47, 6, 6, 3 Hz), 5.56 (dd, 1H, J=15, 6 Hz), 6.99-7.08 (m, 2H), 7.17-7.25 (m, 2H), 7.32 (dd, 1H, J=8, 6 Hz), 7.42-7.48 (m, 3H).

R,R)-(3-Propyl-oxiranyl)-methanol

Add trans-2-hexen-1-ol (12 mL, 102 mmol), (−)-diethyl tartrate (2.1 mL, 12.3 mmol), and Ti(O$^i$Pr)$_4$ (3.0 mL, 10.2 mmol) to a cooled (−20° C.) solution of activated, dried, crushed 4 Å molecular sieves (50 g) in dichloromethane (700 mL). After 30 minutes, add a dry [JACS, 1987, 109, 5765] solution of tBuOOH in dichloromethane (~5M in dichloromethane, 57 mL, 285 mmol). Stir for 4 hours at −20° C. and filter the solids. Add 700 mL of 15% L-tartaric acid to the filtrate and stir for 20 minutes. Separate the layers, extract the aqueous layer with dichloromethane, and concentrate the combined organic extracts in vacuo. Add 300 mL diethyl ether to residue and cool to 0° C. Add cool (0° C.) 15% NaOH, stir for 15 minutes, separate, and extract aqueous layer with diethyl ether. Wash the organic layer with aqueous saturated sodium chloride, dry over anhydrous MgSO$_4$, filter, and concentrate in vacuo. Purify on silica gel eluting with 0-50% EtOAc/hexanes to give (R,R)-(3-propyl-oxiranyl)-methanol (5.69 g, 48%). $^1$H NMR (CDCl$_3$) δ 3.97-3.88 (m, 1H), 3.68-3.59 (m, 1H), 3.00-2.91 (m, 2), 1.83-1.68 (m, 1H), 1.61-1.41 (m, 4H), 0.97 (t, 3H). A similarly carried out Sharpless asymmetric epoxidation of trans-2-hexen-1-ol is described in *J. Org. Chem.* 1994, 59, 4461 and is reported to proceed in >95% ee by $^1$H NMR analysis of the Mosher esters.

(2R,3S)-3-(3,5-Dichloro-phenoxy)-hexane-1,2-diol

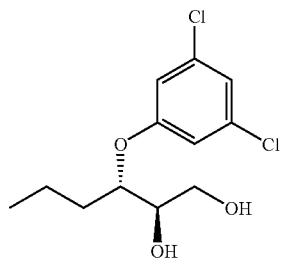

Add sodium hydroxide (1N, 9 mL) to a stirred solution of 3,5-dichlorophenol in THF (9 mL) followed by a solution of (R,R)-(3-propyl-oxiranyl)-methanol in THF (5 mL). Heat the reaction mixture at 75° C. overnight, cool to room temperature, add water, brine and dichloromethane, and separate the layers. The aqueous layer is extracted with dichloromethane, the combined organic extracts are washed successively with 1N sodium hydroxide and water, dried over anhydrous magnesium sulfate, and concentrated under reduced pressure. Analysis of the crude reaction mixture by $^1$H NMR reveals a ~2:1 mixture of the C-3:C-1 adducts. Purification of the crude residue on silica gel eluting with 0-25% EtOAc/hexanes gives the major title compound (332 mg, 26%). $^1$H NMR (DMSO-d6): 0.86 (dd, 3H, J=4, 4 Hz), 1.21-1.48 (m, 2H), 1.52-1.72 (m, 2H), 3.28-3.45 (m, 2H), 3.60-3.67 (m, 2H), 4.37-4.44 (m, 1H), 4.69 (dd, 1H, J=6, 6 Hz), 4.88 (d, 1H, J=5 Hz), 7.01-7.10 (m, 3H).

(2R,3S)-3-(2,4-Dichloro-phenoxy)-hexane-1,2-diol

Using a method similar to that for described for the preparation of (2R,3S)-3-(3,5-dichloro-phenoxy)-hexane-1,2-diol, the title compound is obtained as a powder (317 mg, 33%). $^1$H NMR (DMSO-d6): 0.85 (dd, 3H, J=7, 7 Hz), 1.23-1.50 (m, 2H), 1.56-1.77 (m, 2H), 3.35-3.50 (m, 2H), 3.63-3.70 (m, 2H), 4.38-4.44 (m, 1H), 4.65 (dd, 1H, J=6, 6 Hz), 4.89 (d, 1H, J=5 Hz), 7.20 (d, 1H, J=9 Hz), 7.31 (dd, 1H, J=9, 3 Hz), 7.51 (d, 1H, J=3 Hz).

(2S, 3S)-Toluene-4-sulfonic acid 3-(3,5-dichlorophenoxy)-2-hydroxy-hexyl ester

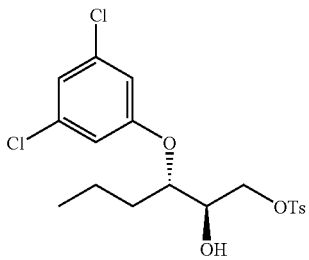

Add p-toluenesulfonyl chloride (339 mg, 1.78 mmol, 1.5 equiv.) to a cold (0° C.) stirred solution of (2R,3S)-3-(2,4-dichloro-phenoxy)-hexane-1,2-diol (332 mg, 1.19 mmol, 1 equiv.) and stir at 0° C. for 6 hr before slowly warming to room temperature overnight. Add dichloromethane and 1 N hydrochloric acid, separate the layers, extract the aqueous layer with dichloromethane (three times), washed the combined organic extracts with 1N hydrochloric acid, dry over anhydrous magnesium sulfate, filter, and concentrate under reduced pressure. Purification of the crude residue on silica gel eluting with 0-15% EtOAc/hexanes gives the title compound as a colorless oil (306 mg, 59%). $^1$H NMR (CD$_3$OD): 0.86 (dd, 3H, J=7, 7 Hz), 1.23-1.47 (m, 2H), 1.63-1.71 (m, 2H), 2.42 (s, 3H) 3.83-3.88 (m, 1H), 4.00 (dd, 1H, J=10, 5 Hz), 4.15 (dd, 1H, J=10, 4 Hz), 4.29-4.37 (m 1H), 6.79 (d, 1H, J=2 Hz), 6.98 (dd, 1H, J=2 Hz), 7.32 (d, 1H, J=8 Hz), 7.67 (dd, 1H, J=8 Hz).

(2S, 3S)-Toluene-4-sulfonic acid 3-(2,4-dichlorophenoxy)-2-hydroxy-hexyl ester

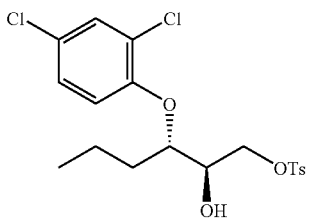

Using a method similar to that for described for the preparation of (2S, 3S)-toluene-4-sulfonic acid 3-(3,5-dichlorophenoxy)-2-hydroxy-hexyl ester, the title compound is obtained as a colorless viscous oil (266 mg, 55%). $^1$H NMR (CDCl$_3$): 0.90 (dd, 3H, J=7, 7 Hz), 1.30-1.52 (m, 2H), 1.57-1.80 (m, 2H), 2.44 (s, 3H) 3.99-4.06 (m, 1H), 4.17 (dd, 1H, J=10, 6 Hz), 4.25-4.36 (m 2H), 6.87 (d, 1H, J=9 Hz), 7.14 (d, 1H, J=9 Hz), 7.27-7.39 (m, 2H), 7.73 (d, 1H, J=8 Hz).

EXAMPLE 1

(2S,3S)-2-Fluoro-3-(naphthalen-1-yloxy)-3-phenyl-propylamine

To a solution of (1S,2R)-3-Azido-1-(naphthalen-1-yloxy)-1-phenyl-propan-2-ol (1.0 g, 3.1 mmol) in 5 mL of CH$_2$Cl$_2$ was added DMAP (0.37 g, 3.4 mmol). This mixture was cooled to −78° C. To this mixture was added DeOxo-Fluor (2.0 mL, 10.8 mmol). The solution was allowed to warm to rt over 5 h. The reaction was quenched by adding to a rapidly stirring solution of CH$_2$Cl$_2$ and NaHCO$_3$ (sat). The layers were separated and the aqueous phase was further extracted 2 times with CH$_2$Cl$_2$. The combined organic phase was dried (MgSO$_4$) and concentrated in vacuo. A portion of the residue (0.18 g) was taken up in 5 mL of THF and to this solution was added PPh$_3$ (0.146 g, 0.56 mmol) and 0.3 mL of water. The resulting solution was allowed to stir overnight. The reaction was poured directly onto an SCX ion exchange column (5 g, Varian). The column was washed with CH$_2$Cl$_2$ and MeOH. The product was removed with 2M NH$_3$ in MeOH and concentrated in vacuo. The residue was purified by flash chromatography eluting silica gel with CH$_2$Cl$_2$: MeOH (2M NH$_3$) [100:0 to 5:1] to yield the title compound (0.147 g, 41%). Mass spectrum (ion spray): m/z=296 (m+1).

Similarly prepared were

EXAMPLE 2

(2R,3R)-2-Fluoro-3-(naphthalen-1-yloxy)-3-phenyl-propylamine

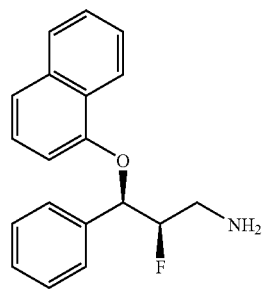

(0.89 g, 51%) of the title compound; Mass spectrum (ion spray): m/z=296 (m+1).

EXAMPLE 3

(2S,3S)-3-(Benzofuran-7-yloxy)-2-fluoro-3-phenyl-propylamine

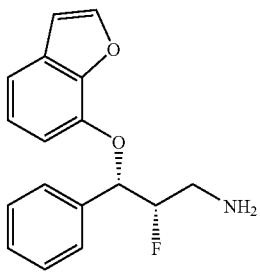

(0.183 g, 33%) of the title compound; Mass spectrum (ion spray): m/z=286.2 (m+1).

EXAMPLE 4

(2S,3R)-3-(Benzo[b]thiophen-4-yloxy)-2-fluoro-3-phenyl-propylamine

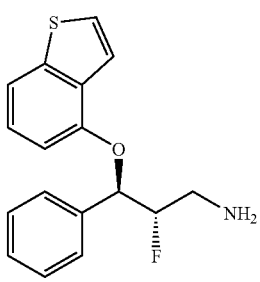

(64 mg, 48%) of the title compound; $\delta_H$ (300 MHz, CDCl$_3$) 7.62 (1H, d), 7.55-7.22 (5H, m), 7.15 (1H, d), 6.96 (1H, t), 6.78-6.65 (2H, m), 5.68-5.58 (1H, m), 5.03-4.79 (1H, m), 2.10-1.6 (2H, m).

EXAMPLE 5

(2S,3S)-3-(Benzo[b]thiophen-4-yloxy)-2-fluoro-3-phenyl-propylamine

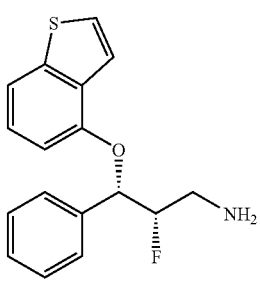

(173 mg, 46%) of the title compound; Mass spectrum (ion spray): m/z=302.2 (m+1).

EXAMPLE 6

(2R,3R)-3-(Benzo[b]thiophen-4-yloxy)-2-fluoro-3-phenyl-propylamine

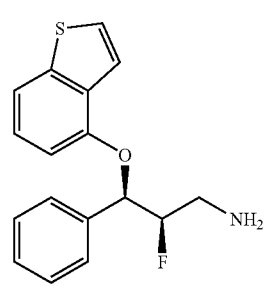

(0.193 g, 35%) of the title compound; Mass spectrum (ion spray): m/z=302.1 (m+1).

EXAMPLE 7

(2R,3S)-3-(Benzo[b]thiophen-4-yloxy)-2-fluoro-3-phenyl-propylamine

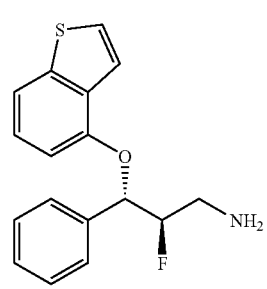

(136 mg, 25%) of the title compound; Mass spectrum (ion spray): m/z 302.1 (m+1).

EXAMPLE 8

(2R,3R)-3-(Benzofuran-7-yloxy)-2-fluoro-3-phenyl-propylamine

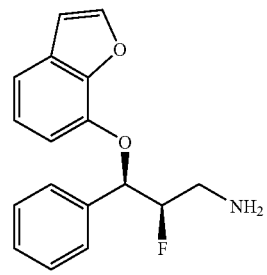

(0.107 g, 22%) of the title compound; Mass spectrum (ion spray): m/z=286.1 (m+1).

EXAMPLE 9

(2S,3S)-3-(2-Methyl-benzofuran-7-yloxy)-2-fluoro-3-phenyl-propylamine

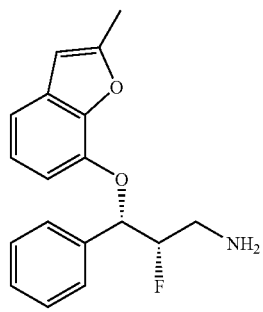

(93 mg, 21%) of the title compound; Mass spectrum (ion spray): m/z=300.2 (m+1).

EXAMPLE 10

(2R,3S)-3-(Benzofuran-7-yloxy)-2-fluoro-3-phenyl-propylamine

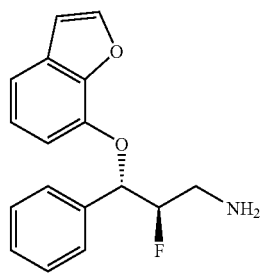

(105 mg, 27%) of the title compound; Mass spectrum (ion spray): m/z=286.2 (m+1).

EXAMPLE 11

(2S,3S)-2-Fluoro-3-(5-fluoro-benzo[b]thiophen-4-yloxy)-3-(3-fluoro-phenyl)-propylamine

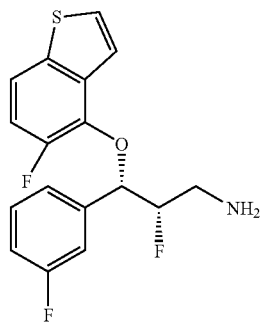

Sequentially add triethylamine (1.1 mL, 7.9 mmol, 4.6 equiv.) and thiophenol (1.1 mL, 11 mmol, 6.2 equiv.) to a room temperature solution of anhydrous tin(II)chloride (489 mg, 2.6 mmol, 1.5 equiv.) in dry dichloromethane (17 mL) and stir the reaction mixture at room temperature for 10 minutes. Add a of solution (1S,2S)-4-[3-azido-2-fluoro-1-(3-fluoro-phenyl)-propoxy]-5-fluoro-benzo[b]thiophene (628 mg, 1.73 mmol, 1 equiv.) in dry dichloromethane (15 mL) to the reaction mixture and stir at room temperature for 10 minutes before adding 2N sodium hydroxide and dichloromethane. The layers are separated and the aqueous layer is extracted with dichloromethane. The combined organic extracts are washed with 2N NaOH, dried over anhydrous magnesium sulfate, and concentrated in vacuo. The residue is purified by flash chromatography eluting silica gel with $CH_2Cl_2$:MeOH (2M $NH_3$) [100:0 to 96:4] to yield the title compound (534 mg, 92%); Mass spectrum (ion spray): m/z=338.1 (m+1). $\delta_H$ (400 MHz, MeOD) 2.60-2.93 (m, 2H), 4.77-5.00 (m, 1H), 5.56 (dd, 1H, J=16, 6 Hz), 6.99-7.10 (m, 2H), 7.20-7.35 (m, 3H), 7.46-7.61 (m, 3H).

EXAMPLE 12

(2S,3S)-[2-Fluoro-3-(naphthalen-1-yloxy)-3-phenyl-propyl]-dimethyl amine

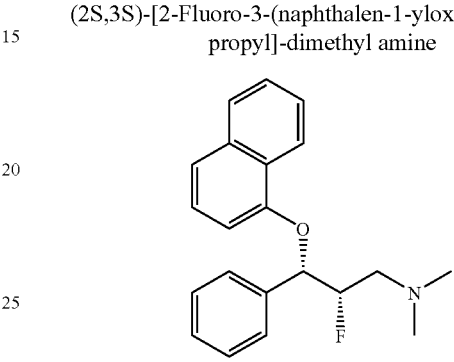

To a solution of (2S,3S)-2-Fluoro-3-(naphthalen-1-yloxy)-3-phenyl-propylamine (0.231 g, 0.78 mmol) in 5 mL of MeOH was added formaldehyde (1.26 mL, 15.6 mmol). This mixture was stirred for 0.5 h before $NaBH(OAc)_3$ (0.82 g, 3.9 mmol) was added. The reaction was allowed to stir overnight at room temperature. The reaction was diluted with $CH_2Cl_2$ and water. The layers were separated and the aqueous phase was further extracted 2 times with $CH_2Cl_2$. The combined organic phase was dried ($MgSO_4$) and concentrated in vacuo. The residue was purified by flash chromatography eluting silica gel with $CH_2Cl_2$:MeOH (2M $NH_3$) [100:0 to 10:1] to yield the title compound (93 mg, 37%); Mass spectrum (ion spray): m/z=324.2 (m+1).

Similarly prepared were

EXAMPLE 13

(2R,3R)-[2-Fluoro-3-(naphthalen-1-yloxy)-3-phenyl-propyl]-dimethyl amine

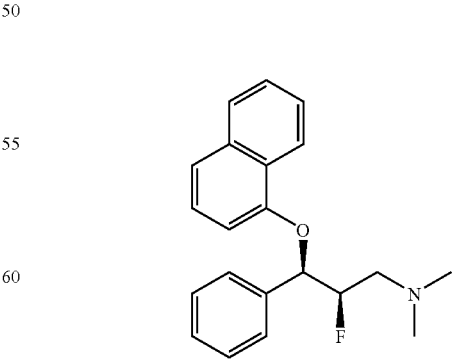

(93 mg, 37%) of the title compound; Mass spectrum (ion spray): m/z=324.2 (m+1).

EXAMPLE 14

(2S,3S)-[3-(Benzofuran-7-yloxy)-2-fluoro-3-phenyl-propyl]dimethylamine

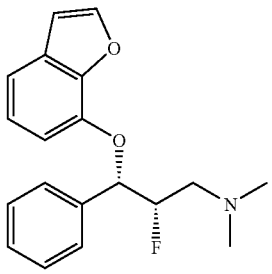

(142 mg, 71%) of the title compound; Mass spectrum (ion spray): m/z=314.2 (m+1).

EXAMPLE 15

(2S,3R)-[3-(Benzo[b]thiophen-4-yloxy)-2-fluoro-3-phenyl-propyl]-dimethyl amine

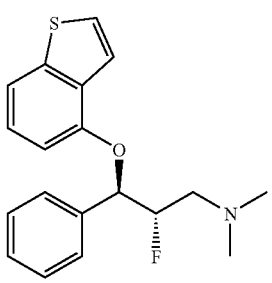

(123 mg, 94%) of the title compound; Mass spectrum (ion spray): m/z=330.2 (m+1).

EXAMPLE 16

(2S,3S)-[3-(Benzo[b]thiophen-4-yloxy)-2-fluoro-3-phenyl-propyl]-dimethyl amine

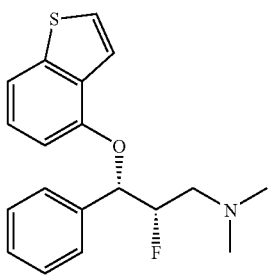

(139 mg, 76%) of the title compound; Mass spectrum (ion spray): m/z=330.1 (m+1).

EXAMPLE 17

(2R,3R)-[3-(Benzo[b]thiophen-4-yloxy)-2-fluoro-3-phenyl-propyl]-dimethyl amine

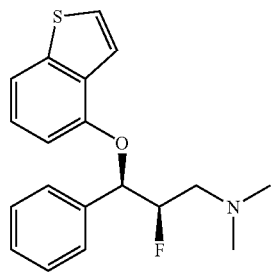

(0.173 g, 83%) of the title compound; Mass spectrum (ion spray): m/z=330.1 (m+1).

EXAMPLE 18

(2R,3S)-[3-(Benzo[b]thiophen-4-yloxy)-2-fluoro-3-phenyl-propyl]-dimethyl amine

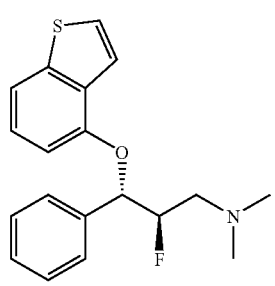

(142 mg, 96%) of the title compound; Mass spectrum (ion spray): m/z=330.1 (m+1).

EXAMPLE 19

(2R,3R)-[3-(Benzofuran-7-yloxy)-2-fluoro-3-phenyl-propyl]dimethylamine

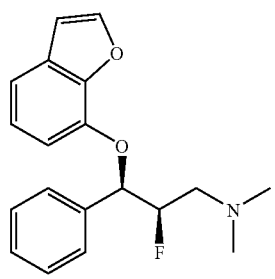

(76 mg, 70%) of the title compound (Carried on directly without characterization see Example 64).

EXAMPLE 20

(2S,3S)-[3-(2-Methyl-benzofuran-7-yloxy)-2-fluoro-3-phenyl-propyl]dimethylamine

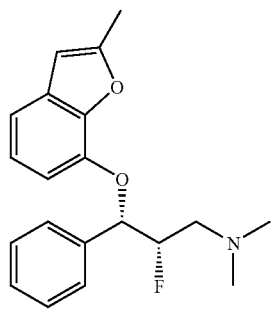

(29 mg, 81%) of the title compound: Mass spectrum (ion spray): m/z=328.2 (m+1).

EXAMPLE 21

(2R,3S)-[3-(Benzofuran-7-yloxy)-2-fluoro-3-phenyl-propyl]-dimethyl amine

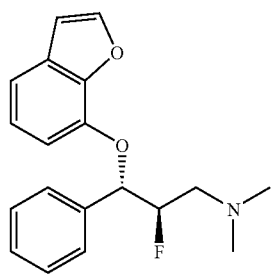

(100 mg, 92%) of the title compound; Mass spectrum (ion spray): m/z=314.2 (m+1).

EXAMPLE 22

(1S,2R)-3-Methylamino-1-(naphthalen-1-yloxy)]-1-phenyl-propan-2-ol hydrochloride

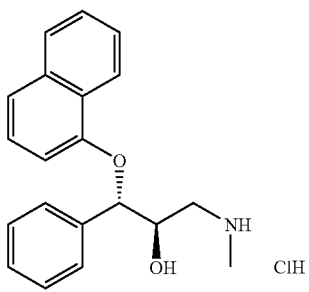

To a solution of (2R,3S)-3-(Naphthalen-1-yloxy)-3-phenyl-propane-1,2-diol (0.69 g, 2.35 mmol) in 20 mL of $CH_2Cl_2$ was added 3 mL of pyridine. This mixture was cooled to −10° C. and to this mixture was added mesyl chloride (0.173 mL, 2.23 mmol). The solution was allowed to warm to RT overnight. The reaction was diluted with $CH_2Cl_2$ and water. The layers were separated and the aqueous phase was further extracted 2 times with $CH_2Cl_2$. The combined organic phase was dried ($MgSO_4$) and concentrated in vacuo. The residue was taken up in 5 mL of EtOH and 20 mL of methylamine (40% in water), the resulting solution was heated to 100° C. in a sealed tube for 3 h. The reaction was allowed to cool to room temperature before the solvent was removed in vacuo. The residue was taken up in $CH_2Cl_2$ and washed with 0.5 N NaOH. The aqueous phase was extracted 2 times with a solution of 3:1 $CHCl_3$:IPA. The combined organic phase was dried ($MgSO_4$) and concentrated in vacuo. The residue was purified by flash chromatography eluting silica gel with $CH_2Cl_2$:MeOH (2M $NH_3$) [100:0 to 4:1] to yield the free-base of the title compound (0.543 g, 80%). A portion of the resulting residue (0.076 g) was dissolved in MeOH (5 mL) and $NH_4Cl$ (13.2 mg) was added. The mixture was sonicated at room temperature for 10 min and then the solvent removed in vacuo. The residue was dissolved in MeCN (0.5 mL) and water (1 mL), this solution was then frozen by immersion in a dry ice: acetone bath, the resulting frozen material was freeze-dried overnight to yield the target compound as a fluffy white solid (85 mg); Melting point of title compound: 84.5° C.

Similarly prepared were

EXAMPLE 23

(1R,2S)-3-Methylamino-1-(naphthalen-1-yloxy)]-1-phenyl-propan-2-ol hydrochloride

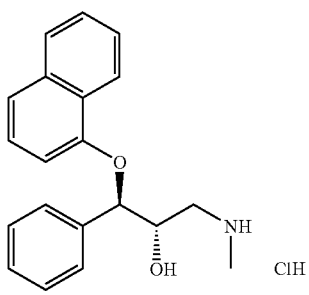

(1.47 g, 71%) of the title compound; Mass spectrum (ion spray): m/z=308.16 (m+1).

EXAMPLE 24

(1S,2R)-1-(Benzofuran-7-yloxy)]-3-methylamino-1-phenyl-propan-2-ol hydrochloride

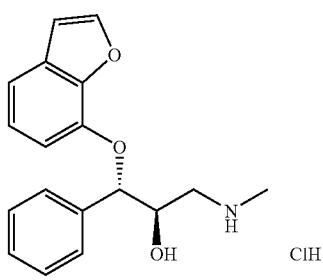

(4 mg, 48%) of the title compound; mass spectrum (ES+): m/z=298.14 (m+1).

EXAMPLE 25

(1S,2R)-1-(7-Fluoro-benzo[b]thiophen-4-yloxy)]-3-methylamino-1-phenyl-propan-2-ol hydrochloride

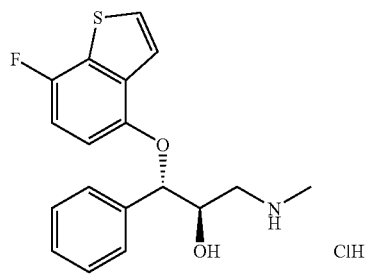

(39 mg, 54%) of the tide compound; mass spectrum (ES+): m/z=332.0 (m+1).

EXAMPLE 26

(1R,2S)-1-(7-Fluoro-benzo[b]thiophen-4-yloxy)]-3-methylamino-1-phenyl-propan-2-ol hydrochloride

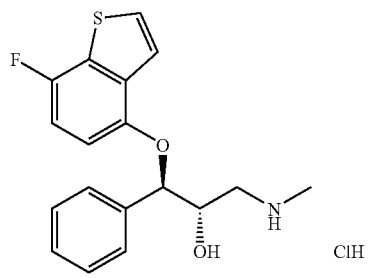

(65 mg, 44%) of the title compound; mass spectrum (ES+): m/z=332.0 (m+1).

EXAMPLE 27

(1R,2S)-1-(Benzo[d]isothiazol-4-yloxy)-3-methylamino-1-phenyl-propan-2-ol hydrochloride

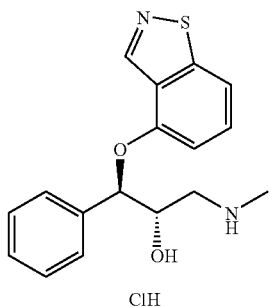

(300 mg, 1.57 mmol) of the title compound (260 mg, 56%); Mass spectrum (ion spray): m/z=315.1 (m+1).

EXAMPLE 28

(1R,2S)-1-(7-Fluoro-benzo[b]thiophen-4-yloxy)]-3-methylamino-1-phenyl-propan-2-ol hydrochloride

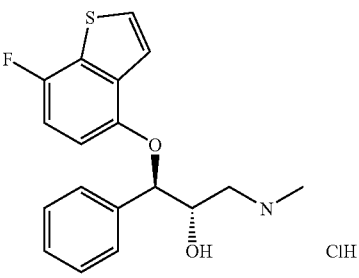

(65 mg, 44%) of the title compound; mass spectrum (ES+): m/z=332.0 (m+1).

EXAMPLE 29

(1R,2S)-1-(Benzo[b]thiophen-7-yloxy)-3-methylamino-1-phenyl-propan-2-ol Hydrochloride

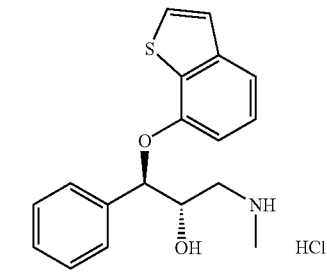

Add p-toluenesulfonyl chloride (240 mg, 1.26 mmol, 1.4 equiv.) to a cold (0° C.) stirred solution of (2S,3R)-3-(benzo[b]thiophen-7-yloxy)-3-phenyl-propane-1,2-diol (269 mg, 0.894 mmol, 1 equiv.) in dry pyridine (4 mL). Allow the reaction mixture to stand at 0° C. overnight and then add an additional aliquot of p-toluenesulfonyl chloride (53 mg, 0.28 mmol, 0.3 equiv.) and store at 0° C. for 8 hr before adding ethyl acetate and 1N HCl. The layers are separated, the aqueous layer is extracted with ethyl acetate (twice), the combined organic extracts are washed with 1N HCl, dried over anhydrous magnesium sulfate and concentrated under reduced pressure.

The crude tosylate thus obtained is dissolved in 1,4-dioxane (8 mL) in a heavy walled screw top sealed tube. Add methyl amine (40% in water, 4 mL), seal the tube, and heat at 50° C. for 2.5 hr. The mixture is cooled and concentrated under reduced pressure. Purification by medium pressure liquid chromatography eluting with 0-4% of 2N $NH_3$/MeOH in dichloromethane is followed by HCl salt formation by dissolving in methanol (15 mL), adding solid ammonium chloride (37 mg, 0.692 mmol) and sonicating for 15-20 minutes. The mixture is concentrated under reduced pressure and the residue is dissolved in water, frozen at −78° C., and freeze dried to afford the title compound as a colorless solid (212 mg, 68%); $\delta_H$ ($CD_3OD$, 400 MHz): 2.76 (s, 3H), 3.29 (dd, 1H, J=13, 10 Hz), 3.43 (dd, 1H, J=13, 3 Hz), 4.28 (ddd, 1H, J=10, 6, 3 Hz), 5.45 (d, 1H, J=6 Hz), 6.66 (d, 1H, J=8 Hz), 7.12 (dd, 1H, J=8, 8 Hz), 7.27-7.43 (m, 5H), 7.46-7.53 (m, 2H), 7.56 (d, 1H, J=5 Hz). Exact Mass cacld. for $C_{18}H_{20}O_2NS$ (M+1H, free base): 314.1215; found: 314.1208.

EXAMPLE 30

(1S,2R)-1-(Benzo[b]thiophen-4-yloxy)-3-methylamino-1-phenyl-propan-2-ol.HCl

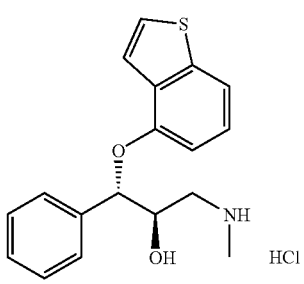

(63 mg, 49%) of the title compound; $\delta_H$ (CD$_3$OD, 400 MHz): 2.75 (s, 3H), 3.23-3.34 (m, 3H), 3.41 (dd, 1H, J=12, 3 Hz), 4.25-4.35 (m, 1H), 5.41 (d, 1H, J=5 Hz), 6.62 (d, 1H, J=8 Hz), 7.08 (dd, 1H, J=8 Hz), 7.30 (d, 1H, J=7 Hz), 7.33-7.40 (m, 2H), 7.47 (d, 1H, J=8 Hz), 7.45-7.50 (m, 2H), 7.51 (d, 1H, J=5 Hz), 7.70 (d, 1H, J=5 Hz). Exact Mass cacld. for $C_{18}H_{20}O_2NS$ (M+1H, free base): 314.1215; found: 314.1215.

EXAMPLE 31

(1R,2S)-1-(Benzo[b]thiophen-4-yloxy)-3-methylamino-1-phenyl-propanol.HCl

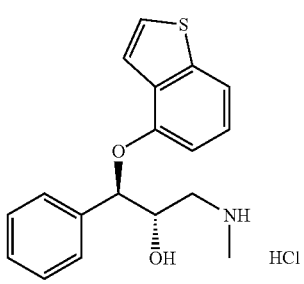

(259 mg, 64%) of the title compound; $\delta_H$ (CD$_3$OD, 400 MHz): 2.75 (s, 3H), 3.23-3.34 (m, 3H), 3.41 (dd, 1H, J=12, 3 Hz), 4.25-4.35 (m, 1H), 5.41 (d, 1H, J=5 Hz), 6.62 (d, 1H, J=8 Hz), 7.08 (dd, 1H, J=8 Hz), 7.30 (d, 1H, J=7 Hz), 7.33-7.40 (m, 2H), 7.47 (d, 1H, J=8 Hz), 7.45-7.50 (m, 2H), 7.51 (d, 1H, J=5 Hz), 7.70 (d, 1H, J=5 Hz). Exact Mass cacld. for $C_{18}H_{20}O_2NS$ (M+1H, free base): 314.1215; found: 314.1193.

EXAMPLE 32

(1S,2R)-1-(4-Fluoro-naphthalen-1-yloxy)-1-(3-fluoro-phenyl)-3-methylamino-propan-2-ol Hydrochloride

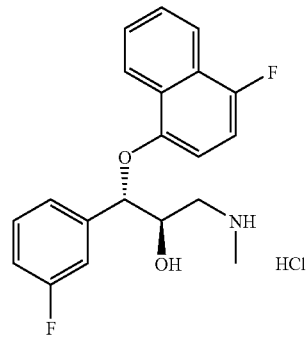

(800 mg, 53%) of the title compound; $\delta_H$ (CD$_3$OD, 400 MHz): 2.77 (s, 3H), 3.28 (dd, 1H, J=13, 10 Hz), 3.45 (dd, 1H, J=13, 3 Hz), 4.36 (ddd, 1H, J=10, 6, 3 Hz), 5.42 (d, 1H, J=1 Hz), 6.64 (dd, 1H, J=9, 4 Hz), 6.92 (dd, 1H, J=10, 9 Hz), 7.04 (dddd, 1H, J=9, 9, 2, 0.4 Hz), 7.23 (ddd, 1H, J=10, 3, 3 Hz), 7.37 (ddd, 1H, J=8, 8, 6 Hz), 7.58-7.67 (m, 2H), 7.97-8.03 (m, 1H), 8.44-8.50 (M, 1H). Mass spectrum (m/e): 344 (M+1H, free base). Ki (NET)=15.2 nM, Ki (SERT)=1.1 nM

EXAMPLE 33

(1S,2R)-1-(Benzo[b]thiophen-4-yloxy)-1-(3-fluorophenyl)-3-methylamino-propan-2-ol Hydrochloride

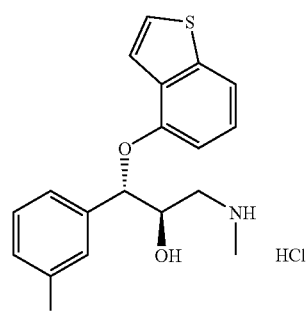

(310 mg, 65%) of the title compound; $\delta_H$ (CD$_3$OD, 400 MHz): 2.75 (s, 3H) 3.24 (dd, 1H, J=12, 10 Hz), 3.42 (dd, 1H, J=12, 3 Hz), 4.29 (ddd, 1H, J=10, 6, 3 Hz), 5.40 (d, 1H, J=6 Hz), 6.63 (d, 1H, J=8 Hz), 7.04 (ddd, 1H, J=9, 9, 3 Hz), 7.10 (dd, 1H, J=8, 8 Hz), 7.22 (ddd, 1H, J=10, 3, 3 Hz), 7.29 (d, 1H, J=8 Hz), 7.38 (ddd, 1H, J=8, 6, 6 Hz), 7.44 (d, 1H, J=8 Hz), 7.52 (d, 1H, J=6 Hz), 7.69 (d, 1H, J=5 Hz). Exact Mass cacld. for $C_{18}H_{19}O_2NFS$ (M+1H free base): 332.1121; found: 332.1147.

EXAMPLE 34

(1R,2S)-1-(Benzo[b]thiophen-4-yloxy)-1-(3-fluoro-phenyl)-3-methylamino-propan-2-ol Hydrochloride

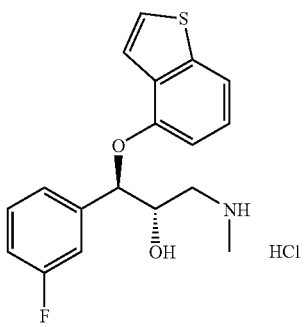

(384 mg, 69%) of the title compound; $\delta_H$ (CD$_3$OD, 400 MHz): 2.75 (s, 3H), 3.24 (dd, 1H, J=12, 10 Hz), 3.42 (dd, 1H, J=12, 3 Hz), 4.29 (ddd, 1H, J=10, 6, 3 Hz), 5.40 (d, 1H, J=6 Hz), 6.63 (d, 1H, J=8 Hz), 7.04 (ddd, 1H, J=9, 9, 3 Hz), 7.10 (dd, 1H, J=8, 8 Hz), 7.22 (ddd, 1H, J=10, 3, 3 Hz), 7.29 (d, 1H, J=8 Hz), 7.38 (ddd, 1H, J=8, 6, 6 Hz), 7.44 (d, 1H, J=8 Hz), 7.52 (d, 1H, J=6 Hz), 7.69 (d, 1H, J=5 Hz). Exact Mass cacld. for C$_{18}$H$_{19}$O$_2$NFS (M+1H, free base): 332.1121; found: 332.1131.

EXAMPLE 35

(1S,2R)-1-(5-Fluoro-benzo[b]thiophen-4-yloxy)-1-(3-fluoro-phenyl)-3-methylamino-propan-2-ol hydrochloride

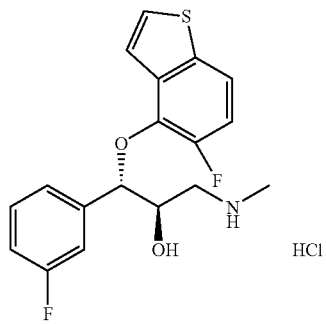

(531 mg, 69%) of the title compound; $\delta_H$ (CD$_3$OD, 400 MHz): 2.78 (s, 3H), 3.22 (dd, 1H, J=13, 10 Hz), 3.54 (dd, 1H, J=13, 3 Hz), 4.40-4.47 (m, 1H), 5.36 (d, 1H, J=6 Hz), 7.01 (dddd, 1H, J=9, 9, 2, 1 Hz), 7.09 (dd, 1H, J=12, 9 Hz), 7.20-7.33 (m, 3H), 7.44 (d, 1H, J=6 Hz), 7.51 (dd, 1H, J=9, 4 Hz), 7.55 (d, 1H, J=6 Hz). Exact Mass cacld. for C$_{18}$H$_{20}$O$_2$NS (M+, free base): 350.1026; found: 350.1029.

EXAMPLE 36

(1S,2R)-R-(Benzo[b]thiophen-7-yloxy)-3-methylamino-1-phenyl-propan-2-ol hydrochloride

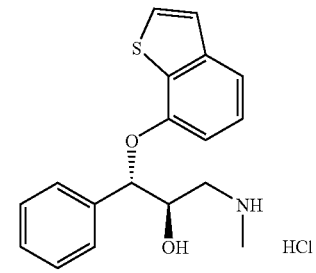

(280 mg, 71%) of the title compound; $\delta_H$ (CD$_3$OD, 400 MHz): 2.76 (s, 3H), 3.29 (dd, 1H, J=13, 10 Hz), 3.43 (dd, 1H, J=13, 3 Hz), 4.28 (ddd, 1H, J=10, 6, 3 Hz), 5.45 (d, 1H, J=6 Hz), 6.66 (d, 1H, J=8 Hz), 7.12 (dd, 1H, J=8, 8 Hz), 7.27-7.43 (m, 5H), 7.46-7.53 (m, 2H), 7.56 (d, 1H, J=5 Hz). Exact Mass cacld. for C$_{18}$H$_{20}$O$_2$NS (M+1H, free base): 314.1215; found: 312.1208.

EXAMPLE 37

(1R,2S)-1-(Benzo[b]thiophen-4-ylsulfanyl)-3-methylamino-1-phenyl-propan-2-ol

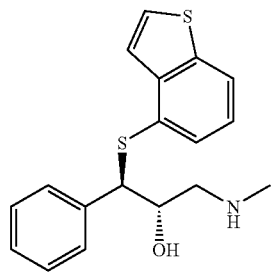

A solution of the (2S,3R)-3-(1-benzothien-4-yloxy)-3-phenylpropan-1,2-diol (236 mg, 0.7 mmol, 1 eq) in pyridine (2 ml) was cooled to 0° C. and tosyl chloride (171 mg, 0.9 mmol, 1.2 eq) was added. This was stirred at 0° C. for 6 hours, then 2N hydrochloric acid (10 ml) was added and the aqueous layer extracted with ethyl acetate (3×20 ml). The combined organics were washed with brine (50 ml) and dried (MgSO$_4$) and the solvent removed in vacuo to give the title compound, which was used without purification in the next step.

The tosylate (360 mg, 0.76 mmol, 1 eq), 40% aqueous methylamine (2.5 ml) and 1,4-dioxane were placed in a sealed vessel and heated to 60° C. for 3 hours. After cooling to room temperature the solvent was removed in vacuo. The crude residue was purified on a 5 g SCX-2 cation exchange resin, loading in methanol (5 ml), washed through with methanol (25 ml) and elute the product with 2M ammonia in methanol (25 ml). The solvent was removed in vacuo, and product triturated with ether to give the title compound as a white solid (146 mg, 63%). $\delta_H$ (300 MHz, CD$_3$OD) 7.70 (1H, d, J=8.0 Hz, ArH), 7.51-7.45 (2H, m, ArH), 7.29-7.22 (3H, m, ArH), 7.15-7.06 (4H, m, ArH), 4.20 (1H, d, J=5.8 Hz, CHS), 4.14-

4.07 (1H, m, CHOH), 2.79 (1H, dd, J=12.2 and 3.0 Hz, CHHOH) and 2.42 (1H, dd, J=9.2 and 3.0 Hz, CHHOH) and 2.28 (3H, s, NHCH$_3$).

Prepared similarly were

EXAMPLE 38

(1S,2R)-1-(Benzo[b]thiophen-4-ylsulfanyl)-3-methylamino-1-phenyl-propan-2-ol

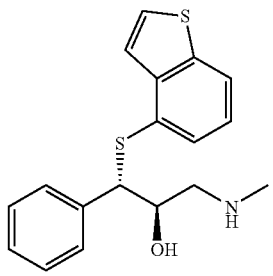

(76 mg) of the title compounds as a white solid; $\delta_H$ (300 MHz, CD$_3$OD) 7.70 (1H, d, J=8.0 Hz, ArH), 7.51-7.45 (2H, m, ArH), 7.29-7.22 (3H, m, ArH), 7.15-7.06 (4H, m, ArH), 4.20 (1H, d, J=5.8 Hz, CHS), 4.14-4.07 (1H, m, CHOH), 2.79 (1H, dd, J=12.2 and 3.0 Hz, CHHOH) and 2.42 (1H, dd, J=9.2 and 3.0 Hz, CHHOH) and 2.28 (3H, s, NHCH$_3$).

EXAMPLE 39

(1S,2R)-1-(Benzo[b]thiophen-7-ylsulfanyl)-3-methylamino-1-phenyl-propan-2-ol

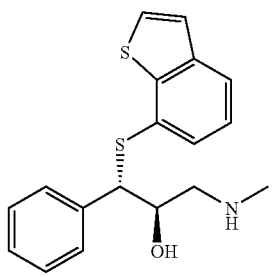

(102 mg) of the title compounds as a white solid; $\delta_H$ (300 MHz, CD$_3$OD) 7.75 (1H, dd, J=7.0 and 2.13 Hz, ArH), 7.58 (1H, d, J=5.5, ArH), 7.39 (1H, d, J=5.5 Hz, ArH), 7.34-7.31 (2H, m, ArH), 7.26-7.18 (5H, m, ArH), 4.42 (1H, d, J=6.0 Hz, CHS), 4.24-4.18 (1H, m, CHOH), 2.88 (1H, dd, J=12.2 and 3.0 Hz, CHHOH) and 2.50 (1H, dd, J=9.2 and 3.0 Hz, CHHOH) and 2.37 (3H, s, NHCH$_3$).

EXAMPLE 40

(1S,2R)-1-(2-Chloro-phenylsulfanyl)-3-methylamino-1-phenyl-propan-2-ol

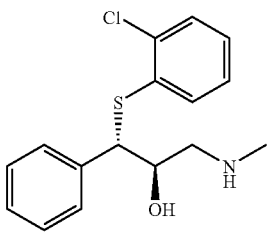

(0.120 g, 14%) of the title compound as an oil; $\delta_H$ (CD$_3$OD) 7.45 (3H, m), 7.2 (4H, m), 7.1 (2H, m), 4.50 (1H, d), 4.20 (1H, m), 3.70 (1H, s), 3.50 (3H, s), 2.80 (1H, dd), 2.50 (1H, m).

EXAMPLE 41

(1R,2S)-1-(2-Chloro-phenylsulfanyl)-3-methylamino-1-phenyl-propan-2-ol

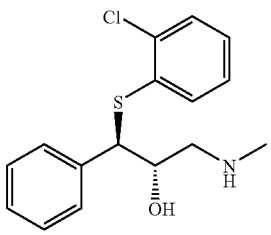

$\delta_H$ (CD$_3$OD) 7.45 (3H, m), 7.2 (4H, m), 7.1 (2H, m), 4.50 (1H, d), 4.20 (1H, m), 3.70 (1H, s), 3.50 (3H, s), 2.80 (1H, dd), 2.50 (1H, m).

EXAMPLE 42

(1S,2R)-1-(2-Fluoro-benzo[b]thiophen-4-yloxy)-3-methylamino-1-phenyl-propan-2-ol

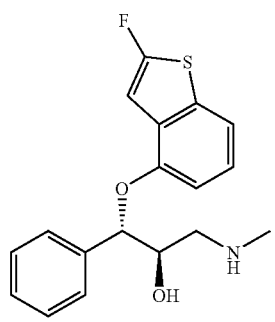

$\delta_H$ (MeOH) 7.60 (1H, d), 7.30 (2H, m), 7.20 (6H, m), 6.60 (1H, d), 5.30 (1H, d), 4.20 (1H, m), 3.50 (1H, m), 3.20 (4H, m), 2.80 (2H, brs).

EXAMPLE 43

(1R,2S)-1-(2-Fluoro-benzo[b]thiophen-4-yloxy)-3-methylamino-1-phenyl-propan-2-ol

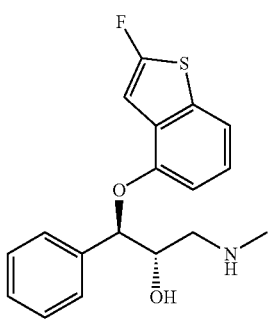

δ$_H$ (MeOH) 7.60 (1H, d), 7.30 (2H, m), 7.20 (6H, m), 6.60 (1H, d), 5.30 (1H, d), 4.20 (1H, m), 3.50 (1H, m), 3.20 (4H, m), 2.80 (2H, brs).

EXAMPLE 44

(1R,2R)-1-(Benzo[b]thiophen-7-yloxy)-3-methylamino-1-phenyl-propan-2R-ol Hydrochloride

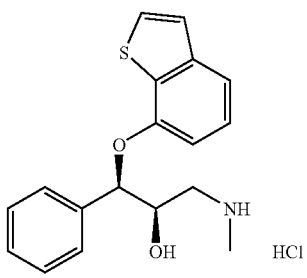

Add methyl amine (40 wt % in water, 3 mL) to a solution of (2R)-2-[(R)-(benzo[b]thiophen-7-yloxy)-phenyl-methyl]-oxirane (150 mg, 0.531 mmol, 1 equiv.) in methanol (3 mL) and 1,4-dioxane (3 mL) in a heavy walled screw cap sealed tube. The tube is sealed and heated at 50° C. overnight, cooled to room temperature, and concentrated under reduced pressure. Purification by medium pressure liquid chromatography eluting with 0-4% of 2N NH$_3$/MeOH in dichloromethane is followed by HCl salt formation by dissolving in methanol (5-10 mL), adding solid ammonium chloride (29.1 mg, 0.554 mmol) and sonicating for 20-25 minutes. The mixture is concentrated under reduced pressure and the residue is dissolved in water, frozen at −78° C., and freeze dried to afford the title compound as a colorless solid (180 mg, 96%). $^1$H nmr (CD$_3$OD, 400 MHz): 2.69 (s, 3H), 3.01 (dd, 1H, J=12, 3 Hz), 3.11 (dd, 1H, J=12, 12 Hz), 4.35 (ddd, 1H, J=12, 6, 3 Hz), 5.48 (d, 1H, J=6 Hz), 6.71 (d, 1H, J=8 Hz), 7.12 (dd, 1H, J=8, 8 Hz), 7.26-7.44 (m, 5H), 7.45-7.54 (m, 2H), 7.55 (d, 1H, J=5 Hz). Exact Mass cacld. for C$_{18}$H$_{20}$O$_2$NS (M+1H, free base): 314.1215; found: 314.1203.

Similarly prepared were

EXAMPLE 45

(1S,2S)-1-(Benzo[b]thiophen-7-yloxy)-3-methylamino-1-phenyl-propan-2-ol Hydrochloride

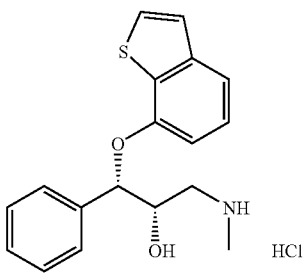

(166 mg, 72%) of the title compound as a colorless solid; δ$_H$ (CD$_3$OD, 400 MHz): 2.69 (s, 3H), 3.01 (dd, 1H, J=12, 3 Hz), 3.11 (dd, 1H, J=12, 12 Hz), 4.35 (ddd, 1H, J=12, 6, 3 Hz), 5.48 (d, 1H, J=6 Hz), 6.71 (d, 1H, J=8 Hz), 7.12 (dd, 1H, J=8, 8 Hz), 7.26-7.44 (m, 5H), 7.45-7.54 (m, 2H), 7.55 (d, 1H, J=5 Hz). Exact Mass cacld. for C$_{18}$H$_{20}$O$_2$NS (M+1H, free base): 314.1215; found: 314.1207.

EXAMPLE 46

(1S,2S)-1-(Benzo[b]thiophen-4-yloxy)-3-methylamino-1-phenyl-propan-2-ol Hydrochloride

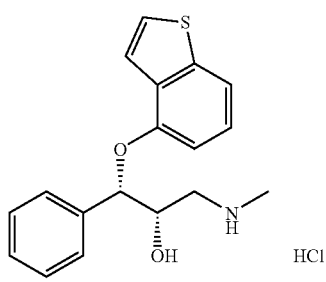

(40 mg, 41%) of the title compound as a colorless solid; δ$_H$ (CD$_3$OD, 400 MHz): 2.69 (s, 3H), 3.03 (dd, 1H, J=13, 3 Hz), 3.12 (dd, 1H, J=13, 11 Hz), 4.35 (ddd, 1H, J=11, 5, 3 Hz), 5.41 (d, 1H, J=5 Hz), 6.65 (d, 1H, J=8 Hz), 7.08 (dd, 1H, J=8, 8 Hz), 7.27-7.44 (m, 4H), 7.47 (d, 1H, J=9 Hz), 7.49 (d, 1H, J=8 Hz), 7.73 (d, 1H, J=5 Hz). Exact Mass cacld. for C$_{18}$H$_{20}$O$_2$NS (M+1H, free base): 314.1215; found: 312.1209.

EXAMPLE 47

(1R,2R)-1-(Benzo[b]thiophen-4-yloxy)-3-methy-lamino-1-phenyl-propan-2-ol Hydrochloride

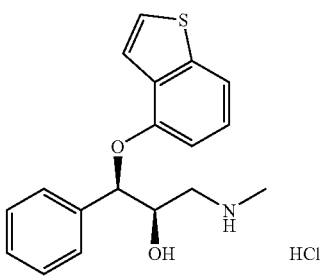

(105 mg, 70%) of the title compound as a colorless solid; $\delta_H$ (CD$_3$OD, 400 MHz): 2.69 (s, 3H), 3.03 (dd, 1H, J=13, 3 Hz), 3.12 (dd, 1H, J=13, 11 Hz), 4.35 (ddd, 1H, J=11, 5, 3 Hz), 5.41 (d, 1H, J=5 Hz), 6.65 (d, 1H, J=8 Hz), 7.08 (dd, 1H, J=8, 8 Hz), 7.27-7.44 (m, 4H), 7.47 (d, 1H, J=9 Hz), 7.49 (d, 1H, J=8 Hz), 7.73 (d, 1H, J=5 Hz). Exact Mass cacld. for C$_{18}$H$_{20}$O$_2$NS (M+1H, free base): 314.1215; found: 314.1193.

EXAMPLE 48

(1R,2R)-3-Amino-1-(benzo[b]thiophen-7-yloxy)-1-phenyl-propan-2-ol hydrochloride

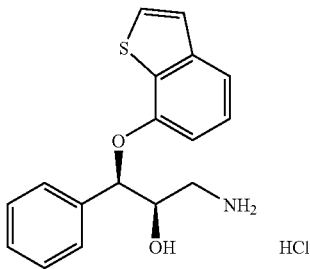

Add concentrated ammonium hydroxide (3 mL) to a solution of (2R)-2-[(R)-(benzo[b]thiophen-7-yloxy)-phenyl-methyl]-oxirane (150 mg, 0.531 mmol, 1 equiv.) in methanol (3 mL) and 1,4-dioxane (3 mL) in a heavy walled screw cap sealed tube. The tube is sealed and heated at 50° C. overnight, cooled to room temperature and concentrated under reduced pressure. Purification by medium pressure liquid chromatography eluting with 0-4% of 2N NH$_3$/MeOH in dichloromethane is followed by HCl salt formation by dissolving in methanol (5-10 mL), adding solid ammonium chloride (21.8 mg, 0.408 mmol) and sonicating for 20-25 minutes. The mixture is concentrated under reduced pressure and the residue is dissolved in water, frozen at −78° C., and freeze dried to afford the title compound as a colorless solid (145 mg, 81%); $\delta_H$ (CD$_3$OD, 400 MHz): 2.90-3.03 (m, 2H), 4.25-4.35 (m, 1H), 4.61 (br s, 1H), 5.50 (d, 1H, J=5 Hz), 6.71 (d, 1H, J=8 Hz), 7.13 (dd, 1H, J=8, 8 Hz), 7.27-7.43 (m, 5H), 7.45-7.53 (m, 2H), 7.55 (d, 1H, J=5 Hz). Exact Mass cacld. for C$_{17}$H$_{18}$O$_2$NS (M+1H, free base): 300.1058; found: 300.1040.

EXAMPLE 49

(1R,2R)-1-(Benzo[b]thiophen-7-yloxy)-3-ethy-lamino-1-phenyl-propan-2-ol hydrochloride

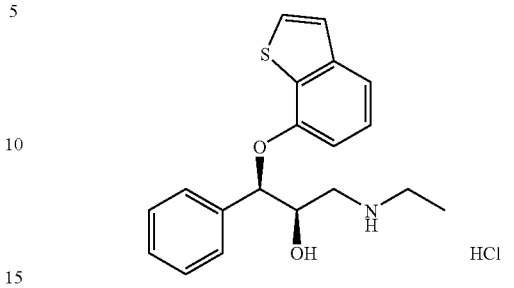

Add ethyl amine (2M in methanol, 3 mL) to a solution of (2R)-2-[(R)-(benzo[b]thiophen-7-yloxy)-phenyl-methyl]-oxirane (150 mg, 0.531 mmol, 1 equiv.) in methanol (3 mL), 1,4-dioxane (3 mL), and water (3 mL) in a heavy walled screw cap sealed tube. The tube is sealed and heated at 50° C. overnight, cooled to room temperature and concentrated under reduced pressure. Purification by medium pressure liquid chromatography eluting with 0-4% of 2N NH$_3$/MeOH in dichloromethane is followed by HCl salt formation by dissolving in methanol (5-10 mL), adding solid ammonium chloride (25.5 mg, 0.477 mmol) and sonicating for 20-25 minutes. The mixture is concentrated under reduced pressure and the residue is dissolved in water, frozen at −78° C., and freeze dried to afford the title compound as a colorless solid (146 mg, 76%); $\delta_H$ (CD$_3$OD, 400 MHz): 1.28 (dd, 3H, 7, 7 Hz), 2.98-3.15 (m, 4H), 4.31-4.40 (m, 1H), 5.49 (d, 1H, J=6 Hz), 6.70 (d, 1H, J=8 Hz), 7.13 (dd, 1H, J=8, 8 Hz), 7.27-7.42 (m, 5H), 7.46-7.53 (m, 2H), 7.55 (d, 1H, J=6 Hz). Exact Mass cacld. For C$_{19}$H$_{22}$O$_2$NS (M+1H, free base): 328.1371; found: 328.1360.

EXAMPLE 50

(1S,2R)-3-Amino-1-(naphthalen-1-yl-oxy)-1-phenyl-propan-2-ol hydrochloride

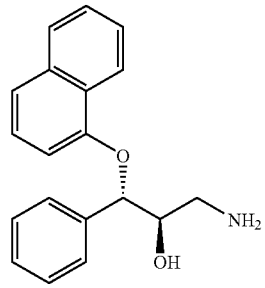

To a solution of (1S,2R)-3-Azido-1-(naphthalen-1-yloxy)-1-phenyl-propan-2-ol (0.456 g, 1.4 mmol) in 10 mL of THF was added PPh$_3$ (0.49 g, 1.8 mmol) and 0.1 mL of water. The solution was allowed to stir at rt overnight. The reaction was diluted with ethyl acetate and placed directly on an SCX column (5 g, Varian). The column was washed with MeOH and CH$_2$Cl$_2$ and the product was removed with 2M NH$_3$: MeOH and concentrated in vacuo. The residue was purified by flash chromatography eluting silica gel with CH$_2$Cl$_2$: MeOH (2M NH$_3$) [100:0 to 5:1] to yield the free-base of the title compound (0.325 g, 80%). The resulting residue was dissolved in MeOH and NH$_4$Cl was added. The mixture was sonicated at room temperature for 10 min and then the solvent removed in vacuo. The residue was dissolved in MeCN (0.5 mL) and water (1 mL), this solution was then frozen by immersion in a dry ice: acetone bath, the resulting frozen material was freeze-dried overnight to yield the title compound as a fluffy white solid; mass spectrum (ES+): m/z=294.15 (m+1).

EXAMPLE 51

(1S,2R)-3-Dimethylamino-1-(naphthalen-1-yl-oxy)-1-phenyl-propan-2-ol hydrochloride

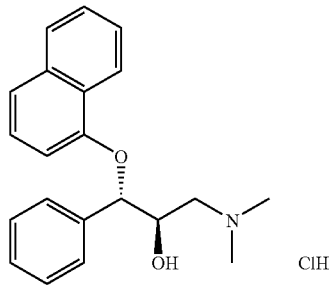

To a solution of (1S,2R)-3-Amino-1-(naphthalen-1-yl-oxy)-1-phenyl-propan-2-ol (0.1982 g, 0.676 mmol) in 10 mL of MeOH was added formaldehyde (37%) (1.2 mL, 13.5 mmol) and the reaction was allowed to stir for 0.5 h whereupon NaBH(OAc)$_3$ (1.42 g, 6.76 mmol) was added. The solution was allowed to stir at rt overnight. The reaction was concentrated in vacuo. The residue was taken up in CH$_2$Cl$_2$ and washed with 2 N NaOH. The aqueous phase was extracted with CH$_2$Cl$_2$ (2×20 mL). The combined organic phases were dried (MgSO$_4$) and concentrated in vacuo. The residue was purified by flash chromatography eluting silica gel with CH$_2$Cl$_2$:MeOH (2M NH$_3$) [100:0 to 5:1] to yield the free-base of the title compound (0.1482 g, 68%). The resulting residue was dissolved in MeOH and NH$_4$Cl was added. The mixture was sonicated at room temperature for 10 min and then the solvent removed in vacuo. The residue was dissolved in MeCN (0.5 mL) and water (1 mL), this solution was then frozen by immersion in a dry ice: acetone bath, the resulting frozen material was freeze-dried overnight to yield the title compound as a fluffy white solid; mass spectrum (ES+): m/z=322.18 (m+1).

EXAMPLE 52

(2R,3S)-[2-Methoxy-3-(naphthalen-1-yl-oxy)-3-phenyl-propyl]-methylamine hydrochloride a) (2R,3S)-2,2-Difluoro-N-[2-hydroxy-3-(naphthalen-1-yloxy)-3-phenyl-propyl]-N-methyl-acetamide

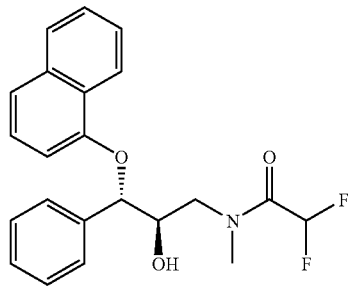

To a solution of (1S,2R)-3-Methylamino-1-(naphthalen-1-yloxy)]-1-phenyl-propan-2-ol (2.17 g, 7.1 mmol) in 150 mL of CH$_2$Cl$_2$ was added 10 mL of pyridine and the solution was cooled to 0° C. Difluoroacetic anhydride (0.82 mL, 6.9 mmol) was added in 4 equal portions and the solution was allowed to stir at rt overnight. The reaction was diluted with CH$_2$Cl$_2$ and 0.5N NaOH. The layers were separated and the aqueous phase was further extracted 2 times with CH$_2$Cl$_2$. The combined organic phase was dried (MgSO$_4$) and concentrated in vacuo. The residue was purified by flash chromatography eluting silica gel with CH$_2$Cl$_2$:MeOH (2M NH$_3$) [100:0 to 10:1] to yield the title compound (1.74 g, 65%); $\delta_H$ (300 MHz, CDCl$_3$): 8.45 (1H, d), 7.83-7.78 (1H, m), 7.59-7.16 (9H, m), 6.59 (1H, d), 5.38 (1H, d), 5.30 (1H, t), 4.39-4.24 (1H, m), 3.88-3.81 (2H, m), 3.18-3.10 (3H, m).

b) (2R,3S)-[2-Methoxy-3-(naphthalen-1-yl-oxy)-3-phenyl-propyl]-methylamine hydrochloride

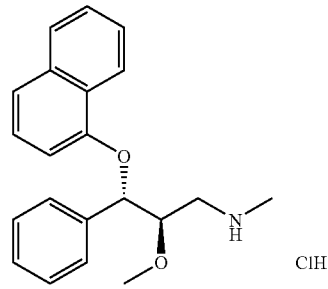

To a solution of (2R,3S)-2,2-Difluoro-N-[2-hydroxy-3-(naphthalene-1-yloxy)-3-phenyl-propyl]-N-methyl-acetamide (0.3 g, 0.78 mmol) in 2 mL of THF was added NaH (60%) (0.12 g, 3.1 mmol) and the reaction was allowed to stir for 0.25 h. Methyl iodide (0.55 mL, 3.9 mmol) was added and the solution was allowed to stir at rt overnight. The reaction was diluted with CH$_2$Cl$_2$ and NaHCO$_3$(sat). The layers were separated and the aqueous phase was further extracted 2 times with CH$_2$Cl$_2$. The combined organic phase was dried (MgSO$_4$) and concentrated in vacuo. The residue was purified by flash chromatography eluting silica gel with hexane:ethyl acetate [100:0 to 1:1]. The corresponding fractions were collected and concentrated in vacuo. The residue was taken up in 20 mL of 5N HCl and 2 mL of MeOH and heated at 90° C. overnight. After cooling, the solution was concentrated in vacuo and diluted with CH$_2$Cl$_2$ and NaHCO$_3$(sat). The layers were separated and the aqueous phase was further extracted 2 times with CH$_2$Cl$_2$. The combined organic phase was dried (MgSO$_4$) and concentrated in vacuo. The residue was purified by flash chromatography eluting silica gel with CH$_2$Cl$_2$:MeOH (2M NH$_3$) [100:0 to 5:1] to yield the title compound as a freebase (43 mg, 19%). The resulting residue was dissolved in MeOH and NH$_4$Cl was added. The mixture was sonicated at room temperature for 10 min and then the solvent removed in vacuo. The residue was dissolved in MeCN (0.5 mL) and water (1 mL), this solution was then frozen by immersion in a dry ice: acetone bath, the resulting frozen material was freeze-dried overnight to yield the title compound as a fluffy white solid; mass spectrum (ES+): m/z=322.18 (m+1).

Prepared similarly was

EXAMPLE 53

(2R,3S)-[2-Benzyloxy-3-(naphthalen-1-yl-oxy)-3-phenyl-propyl]-methylamine hydrochloride

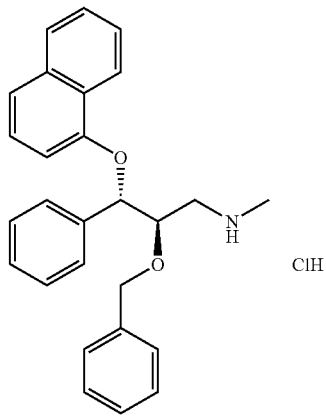

Using (2R,3S)-2,2-Difluoro-N-[2-hydroxy-3-(naphthalene-1-yloxy)-3-phenyl-propyl]-N-methyl-acetamide and benzyl bromide to give the title compound (27 mg, 15%); mass spectrum (ES+): m/z=398.21 (m+1).

EXAMPLE 54

(1R,2R)-1-(7-Fluoro-benzo[b]thiophen-4-yloxy)]-3-methylamino-1-phenyl-propan-2-ol hydrochloride

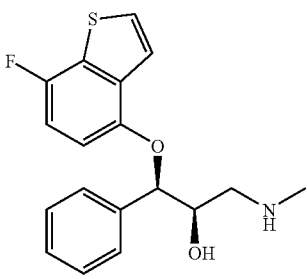

To a solution of (2R)-oxiranyl-(S)-phenyl-methanol (0.235 g, 1.56 mmol, prepared as described in *Tetrahedron Lett.* 1986, 27, 4987) and 7-fluoro-benzo[b]thiophen-4-ol (0.36 g, 2.14 mmol) in 5 mL THF was added PPh$_3$ (0.646 g, 2.46 mmol) and DEAD (0.39 mL, 2.46 mmol). The resulting solution was stirred at rt for 24 h. The reaction was then concentrated in vacuo and the residue was purified by flash chromatography eluting silica gel with hexane:ethyl acetate [100:0 to 3:1]. The corresponding fractions were combined and concentrated in vacuo. The resulting residue was taken up directly into 6 mL of a solution of 1:2 MeNH$_2$(40% in H$_2$O): dioxane and heated at 50° C. for 24 h. The solution was concentrated in vacuo and the residue was taken up in 2 N NaOH and dichloromethane and the organic phase was separated. The aqueous phase was extracted with 2×20 mL dichloromethane. The combined organic phases were dried (MgSO$_4$) and concentrated in vacuo. The residue was purified by flash chromatography eluting silica gel with CH$_2$Cl$_2$: MeOH (2M NH$_3$) [100:0 to 4:1] to yield the free-base of the title compound (129 mg, 68%). The resulting residue was dissolved in MeOH and NH$_4$Cl was added. The mixture was sonicated at room temperature for 10 min and then the solvent removed in vacuo. The residue was dissolved in MeCN (0.5 mL) and water (1 mL), this solution was then frozen by immersion in a dry ice: acetone bath, the resulting frozen material was freeze-dried overnight to yield the title compound as a fluffy white solid; mass spectrum (ES+): m/z=332.1 (m+1).

EXAMPLE 55

(2S,3S)-[2-Fluoro-3-(naphthalen-1-yloxy)-3-phenyl-propyl]-dimethyl amine

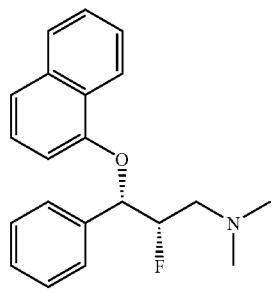

To a solution of (2S,3S)-2-Fluoro-3-(naphthalen-1-yloxy)-3-phenyl-propylamine (0.231 g, 0.78 mmol) in 5 mL of MeOH was added formaldehyde (1.26 mL, 15.6 mmol). This mixture was stirred for 0.5 h before NaBH(OAc)$_3$ (0.82 g, 3.9 mmol) was added. The reaction was allowed to stir overnight at room temperature. The reaction was diluted with CH$_2$Cl$_2$ and water. The layers were separated and the aqueous phase was further extracted 2 times with CH$_2$Cl$_2$. The combined organic phase was dried (MgSO$_4$) and concentrated in vacuo. The residue was purified by flash chromatography eluting silica gel with CH$_2$Cl$_2$:MeOH (2M NH$_3$) [100:0 to 10:1] to yield the title compound (93 mg, 37%); Mass spectrum (ion spray): m/z=324.2 (m+1).

Similarly prepared was

EXAMPLE 56

(2R,3R)-[2-Fluoro-3-(naphthalen-1-yloxy)-3-phenyl-propyl]-dimethyl amine

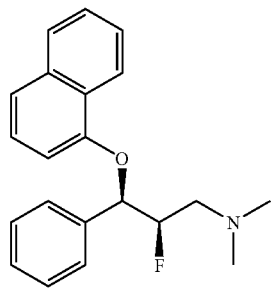

(93 mg, 37%) of the title compound; Mass spectrum (ion spray): m/z=324.2 (m+1).

EXAMPLE 57

(2S,3S)-[2-Fluoro-3-(naphthalen-1-yloxy)-3-phenyl-propyl]-methylamine hydrochloride

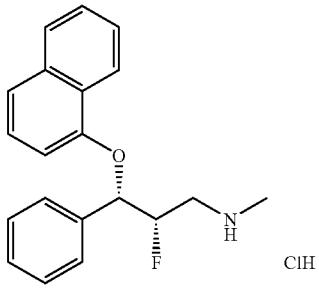

To a solution of (2S,3S)-[2-Fluoro-3-(naphthalen-1-yloxy)-3-phenyl-propyl]-dimethyl amine (0.083 g, 0.25 mmol) in 5 mL of 1,2 dichloroethane was added PS-DIEA (Fluka) (0.3 g, 0.7 mmol). To this mixture was added 1-chloroethyl chloroformate (0.14 mL, 1.2 mmol) and the resulting mixture was heated at 85° C. overnight. The reaction was cooled and concentrated in vacuo. The resulting residue was taken up in 5 mL of MeOH and heated at 65° C. for 5 h. The reaction was cooled to room temperature, filtered and concentrated in vacuo. The residue was purified by flash chromatography eluting silica gel with $CH_2Cl_2$:MeOH (2M $NH_3$) [100:0 to 5:1] to yield the title compound as the free base (62 mg, 78%). The resulting residue (was dissolved in MeOH (5 mL) and $NH_4Cl$ (10.7 mg) was added. The mixture was sonicated at room temperature for 10 min and then the solvent removed in vacuo. The residue was dissolved in MeCN (0.5 mL) and water (1 mL), this solution was then frozen by immersion in a dry ice: acetone bath, the resulting frozen material was freeze-dried overnight to yield the target compound as a fluffy white solid (68 mg); Mass spectrum (ion spray): m/z=310.2 (m+1).

Similarly prepared were

EXAMPLE 58

(2R,3R)-[2-Fluoro-3-(naphthalen-1-yloxy)-3-phenyl-propyl]-methylamine hydrochloride

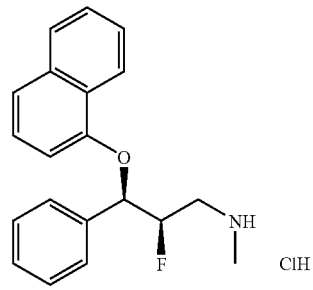

(111 mg, 83%) of the title compound; Mass spectrum (ion spray): m/z=310.2 (m+1).

EXAMPLE 59

(2S,3S)-[3-(Benzofuran-7-yloxy)-2-fluoro-3-phenyl-propyl]-methylamine hydrochloride

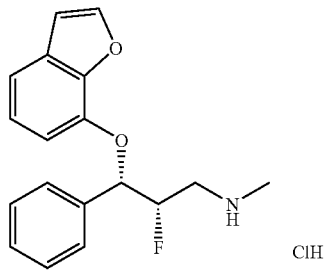

(79 mg, 59%) of the title compound; Mass spectrum (ion spray): m/z=300 (m+1).

EXAMPLE 60

(2S,3R)-[3-(Benzo[b]thiophen-4-yloxy)-2-fluoro-3-phenyl-propyl]-methylamine hydrochloride

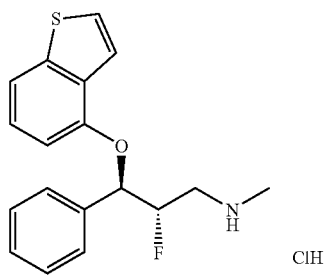

(101 mg, 88%) of the title compound; Mass spectrum (ion spray): m/z=316.1 (m+1).

EXAMPLE 61

(2S,3S)-[3-(Benzo[b]thiophen-4-yloxy)-2-fluoro-3-phenyl-propyl]-methylamine hydrochloride

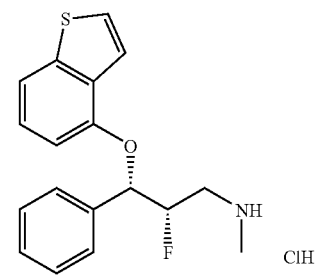

(96 mg, 78%) of the title compound; Mass spectrum (ion spray): m/z=316.1 (m+1).

EXAMPLE 62

(2R,3R)-[3-(Benzo[b]thiophen-4-yl-oxy)-2-fluoro-3-phenyl-propyl]-methylamine hydrochloride

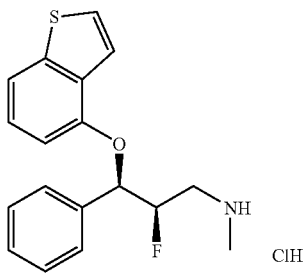

(139 mg, 85%) of the title compound; Mass spectrum (ion spray): m/z=316.1 (m+1).

EXAMPLE 63

(2R,3S)-[3-(Benzo[b]thiophen-4-yloxy)-2-fluoro-3-phenyl-propyl]-methylamine hydrochloride

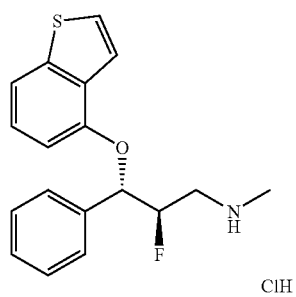

(80 mg, 60%) of the title compound; Mass spectrum (ion spray): m/z=316.1 (m+1).

EXAMPLE 64

(2R,3R)-[3-(Benzofuran-7-yloxy)-2-fluoro-3-phenyl-propyl]-methylamine hydrochloride

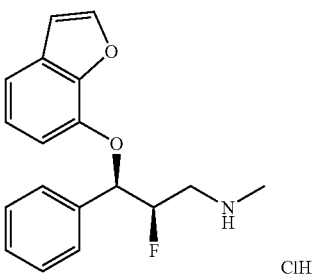

(61 mg, 86%) of gave the title compound; Mass spectrum (ion spray): m/z=300.2 (m+1).

EXAMPLE 65

(2S,3S)-[3-(2-Methyl-benzofuran-7-yloxy)-2-fluoro-3-phenyl-propyl]-methylamine hydrochloride

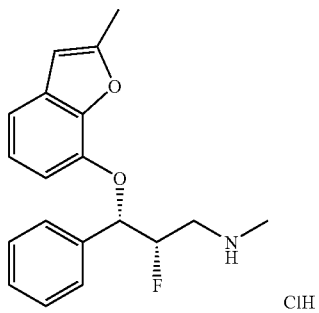

(35 mg, 62%) of the title compound; Mass spectrum (ion spray): m/z=314.2 (m+1).

EXAMPLE 66

(2S,3S)-[3-(Benzofuran-7-yloxy)-2-fluoro-3-phenyl-propyl]-methylamine hydrochloride

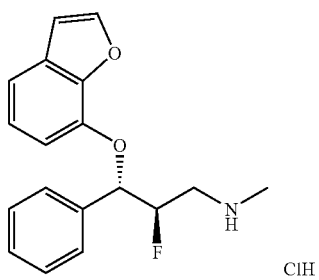

(83 mg, 87%) of the title compound; Mass spectrum (ion spray): m/z=301.1 (m+1).

EXAMPLE 67

(2S,3S)-3-(Benzo[b]thiophen-4-yloxy)-2-fluoro-3-(3-fluoro-phenyl)-propylamine

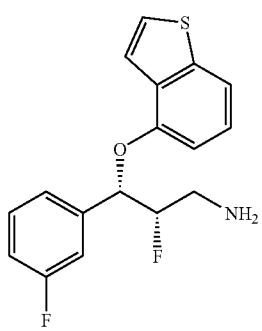

Sequentially add triethyl amine (1.0 mL, 7.17 mmol, 4.5 equiv.) and benzenethiol (1.0 mL, 9.74 mmol, 6.1 equiv.) to a solution of anhydrous tin(II)chloride (460 mg, 2.43 mmol, 1.5 equiv.) in dry THF (15 mL) to afford a yellow suspension. Add (1S,2S)-4-(3-azido-2-fluoro-1-phenyl-propoxy)-benzo[b]thiophene (553 mg, 1.60 mmol, 1 equiv.) as a solution using THF (10 mL) and stir at room temperature for 10 minutes before adding 2N sodium hydroxide and dichloromethane. The layers are separated, the aqueous layer is extracted with dichloromethane (three times), the combined organic extracts are dried over anhydrous magnesium sulfate, filtered, and concentrated under reduced pressure.

Purification by medium pressure liquid chromatography eluting with 0-4% of 2N NH$_3$/MeOH in dichloromethane affords the title compound as a cream colored oil (401 mg, 78%); δ$_H$ (CD$_3$OD, 400 MHz): 2.86 (ddd, 1H, J=30, 14, 3 Hz), 2.99 (ddd, 1H, J=16, 14, 6 Hz), 4.82 (dddd, 1H, J=48, 9, 5, 3 Hz), 5.62 (dd, 1H, J=18, 5 Hz), 6.65 (d, 1H, J=8 Hz), 7.03 (dddd, 1H, J=9, 9, 3, 1 Hz), 7.10 (dd, 1H, J=8, 8 Hz), 7.22 (ddd, 1H, J=10, 2, 2 Hz), 7.30 (d, 1H, J=8 Hz), 7.36 (ddd, 1H, J=9, 8, 6 Hz), 7.42 (d, 1H, J=8 Hz), 7.49 (d, 1H, J=6 Hz), 7.61 (dd, 1H, J=6, 1 Hz).

EXAMPLE 68

(2S,3S)-[3-(Benzo[b]thiophen-4-yloxy)-2-fluoro-3-(3-fluoro-phenyl)-propyl]-dimethyl-amine

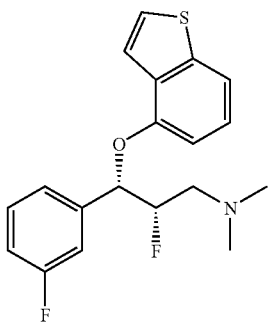

Add formaldehyde (30 wt % in water, 1 mL) to a stirred solution of (2S,3S)-3-(benzo[b]thiophen-4-yloxy)-2-fluoro-3-(3-fluoro-phenyl)-propylamine (360 mg, 1.13 mmol, 1 equiv.) in methanol (10 mL) and stir at room temperature for 10 min before adding sodium triacetoxyborohydride (1.01 g, 4.76 mmol, 4.2 equiv.) and stir at room temperature for 3 hr. The reaction mixture was concentrated in vacuo and saturated aqueous sodium bicarbonate and dichloromethane are added. The layers are separated and the aqueous layer is extracted with dichloromethane (3 times), dried over anhydrous magnesium sulfate, filtered, and concentrated under reduced pressure to afford the title compound as a pale yellow oil (340 mg, 83%); δ$_H$ (CD$_3$OD, 400 MHz): 2.30 (s, 6H), 2.66 (ddd, 1H, J=32, 14, 3 Hz), 2.80 (ddd, 1H, J=17, 14, 8 Hz), 5.01 (dddd, 1H, J=48, 8, 4, 3 Hz), 5.62 (dd, 1H, J=19, 4 Hz), 6.63 (d, 1H, J=8 Hz), 7.02 (dddd, 1H, J=9, 9, 2, 1 Hz), 7.10 (dd, 1H, J=8, 8 Hz), 7.21 (br d, 1H, J=10 Hz), 7.29 (d, 1H, J=8 Hz), 7.36 (ddd, 1H, J=8, 8, 6 Hz), 7.42 (d, 1H, J=9 Hz), 7.50 (d, 1H, J=6 Hz), 7.61 (dd, 1H, J=6, 1 Hz).

Similarly prepared was

EXAMPLE 69

(2S,3S)-[2-Fluoro-3-(5-fluoro-benzo[b]thiophen-4-yloxy)-3-(3-fluoro-phenyl)-propyl]-dimethyl-amine

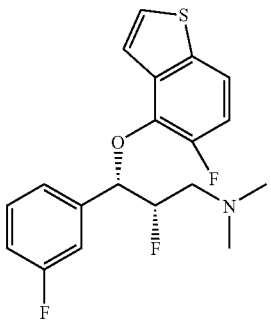

(478 mg, 83%) of the title compound; δ$_H$ (400 MHz, MeOD) 2.27 (s, 6H), 2.52 (ddd, 1H, J=32, 14, 2 Hz), 2.73 (ddd, 1H, 18, 14, 8 Hz), 5.08 (dddd, 1H, J=49, 5, 5, 2 Hz), 5.59 (dd, 1H, J=16, 6 Hz), 6.97 (m, 2H), 7.21-7.33 (m, 3H), 7.45-7.57 (m, 3H). Mass spectrum (ion spray): m/z=366.1 (m+1).

EXAMPLE 70

(2S,3S)-[3-(Benzo[b]thiophen-4-yloxy)-2-fluoro-3-(3-fluoro-phenyl)-propyl]-methyl-amine hydrochloride

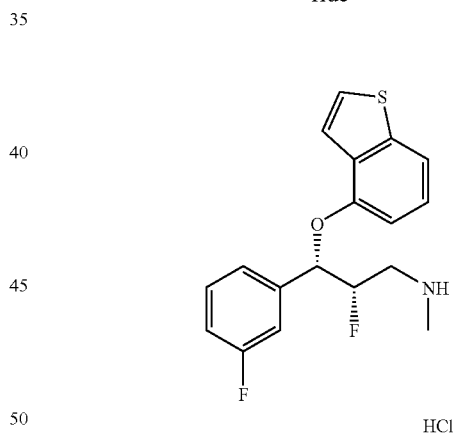

Add Ace-Cl (0.37 mL, 3.43 mmol, 5 equiv.) to a stirred solution of (2S,3S)-[3-(benzo[b]thiophen-4-yloxy)-2-fluoro-3-(3-fluoro-phenyl)-propyl]-dimethyl-amine (250 mg, 0.688 mmol, 1 equiv.) in dry 1,2-dichloroethane and heat at 85° C. for 2.5 hr before cooling to room temperature adding methanol (10 mL) and heating at 85° C. for 1 hr and then gradually cooling to room temperature overnight. Purification by medium pressure liquid chromatography eluting with 0-4% of 2N NH$_3$/MeOH in dichloromethane is followed by HCl salt formation by dissolving in methanol (15 mL), adding solid ammonium chloride (24 mg, 0.45 mmol) and sonicating for 20-25 minutes. The mixture is concentrated under reduced pressure and the residue is dissolved in water, frozen at −78° C., and freeze dried to afford the title compound as an off-white solid (136 mg, 56%); δ$_H$ (CD$_3$OD, 400 MHz): 2.79 (s, 3H), 3.39 (ddd, 1H, J=35, 14, 2 Hz), 3.57-3.69 (m, 1H), 5.25 (dddd, 1H, J=48, 10, 4, 2 Hz), 5.62 (dd, 1H, J=20, 4 Hz), 6.66 (d, 1H, J=8 Hz), 7.06-7.16 (m, 2H), 7.24 (br d, 1H, J=9 Hz), 7.33 (d, 1H, J=8 Hz), 7.41 (ddd, 1H, J=8, 8, 6 Hz), 7.47 (d, 1H, J=8 Hz), 7.55 (d, 1H, J=6 Hz), 7.66 (dd, 1H, J=6, 1 Hz); Mass spec (m/e)=334 (free base). $^1$H nmr (CD$_3$OD, 400 MHz): 2.79 (s, 3H), 3.39 (ddd, 1H, J=35, 14, 2 Hz), 3.57-3.69 (m, 1H), 5.25 (dddd, 1H, J=48, 10, 4, 2 Hz), 5.62 (dd, 1H, J=20, 4 Hz), 6.66 (d, 1H, J=8 Hz), 7.06-7.16 (m, 2H), 7.24 (br d, 1H, J=9 Hz), 7.33 (d, 1H, J=8 Hz), 7.41 (ddd, 1H, J=8, 8, 6 Hz), 7.47 (d, 1H, J=8 Hz), 7.55 (d, 1H, J=6 Hz), 7.66 (dd, 1H, J=6, 1 Hz); Mass spec (m/e)=334 (free base).

Similarly prepared was

EXAMPLE 71

(2S,3S)-[2-Fluoro-3-(5-fluoro-benzo[b]thiophen-4-yloxy)-3-(3-fluoro-phenyl)-propyl]-methyl-amine hydrochloride

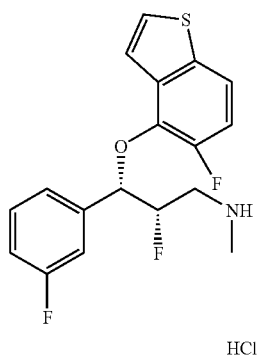

(158 mg, 31%) of the title compound. δ$_H$ (400 MHz, MeOD) 2.73 (s, 3H), 3.20 (ddd, 1H, J=34, 14, 2 Hz), 3.53 (ddd, 1H, 13, 13, 10 Hz), 5.26 (dddd, 1H, J=49, 10, 5, 2 Hz), 5.68 (dd, 1H, J=18, 5 Hz), 7.03-7.13 (m, 2H), 7.25-7.37 (m, 3H), 7.50 (dd, 1H, J=6, 1 Hz), 7.54 (ddd, 1H, 9, 4, 1 Hz), 7.61 (d, 1H, J=6 Hz). Mass spectrum (ion spray): m/z=352.1 (m+1)...0

The compounds of the present invention may be used as medicaments in human or veterinary medicine. The compounds may be administered by various routes, for example, by oral or rectal routes, topically or parenterally, for example by injection, and are usually employed in the form of a pharmaceutical composition.

Such compositions may be prepared by methods well known in the pharmaceutical art and normally comprise at least one active compound in association with a pharmaceutically acceptable diluent or carrier. In making the compositions of the present invention, the active ingredient will usually be mixed with a carrier or diluted by a carrier, and/or enclosed within a carrier which may, for example, be in the form of a capsule, sachet, paper or other container. Where the carrier serves as a diluent, it may be solid, semi-solid, or liquid material which acts as a vehicle, excipient or medium for the active ingredient. Thus, the composition may be in the form of tablets, lozenges, sachets, cachets, elixirs, suspensions, solutions, syrups, aerosol (as a solid or in a liquid medium), ointments containing, for example, up to 10% by weight of the active compound, soft and hard gelatin capsules, suppositories, injection solutions and suspensions and sterile packaged powders.

Some examples of suitable carriers are lactose, dextrose, vegetable oils, benzyl alcohols, alkylene glycols, polyethylene glycols, glycerol triacetate, gelatin, carbohydrates such as starch and petroleum jelly, sucrose sorbitol, mannitol, starches, gum acacia, calcium phosphate, alginates, tragacanth, gelatin, syrup, methyl cellulose, methyl- and propyl-hydrobenzoate, talc, magnesium stearate and mineral oil. The compounds of formula (I) can also be lyophilized and the lyophilizates obtained used, for example, for the production of injection preparations. The preparations indicated can be sterilized and/or can contain auxiliaries such as lubricants, preservatives, stabilizers and/or wetting agents, emulsifiers, salts for affecting the osmotic pressure, buffer substances, colourants, flavourings and/or one or more further active compounds, e.g. one or more vitamins. Compositions of the invention may be formulated so as to provide, quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary doses for human subjects and other mammals, each unit containing a predetermined quantity of active material calculated to produce the desired therapeutic effect, in association with a suitable pharmaceutical carrier.

The pharmacological profile of the present compounds may be demonstrated as follows. All of the exemplified compounds above have been found to exhibit K$_i$ values less than 1 μM at the serotonin and norepinephrine transporters as determined using the scintillation proximity assays described below. Furthermore, all of the exemplified compounds above have been found to exhibit a K$_i$ value less than 100 nM at the serotonin transporter and/or a K$_i$ value less than 100 nM at the norepinephrine transporter as determined using the scintillation proximity assays described below. Preferred compounds of the present invention are those which exhibit a K$_i$ value less than 100 nM (preferably less than 50 nM) at the serotonin transporter and a K$_i$ value less than 100 nM (preferably less than 50 nM) at the norepinephrine transporter as determined using the scintillation proximity assays described below. Furthermore, all of the exemplified compounds above have been found to selectively inhibit the serotonin and norepinephrine transporters relative to the dopamine transporter. Preferred compounds of the present invention selectively inhibit the serotonin and norepinephrine transporters relative to the dopamine transporter by a factor of at least five using the scintillation proximity assays as described below.

Generation of Stable Cell-lines Expressing the Human Dopamine, Norepinephrine and Serotonin Transporters Standard molecular cloning techniques were used to generate stable cell-lines expressing the human dopamine, norepinephrine and serotonin transporters. The polymerase chain reaction (PCR) was used in order to isolate and amplify each of the three full-length cDNAs from an appropriate cDNA library. Primers for PCR were designed using the following published sequence data:

Human dopamine transporter: GenBank M95167. Reference: Vandenbergh D J, Persico A M and Uhl G R. *A human dopamine transporter cDNA predicts reduced glycosylation, displays a novel repetitive element and provides racially-dimorphic TaqI RFLPs*. Molecular Brain Research (1992) volume 15, pages 161-166.

Human norepinephrine transporter: GenBank M65105. Reference: Pacholczyk T, Blakely, R D and Amara S G. *Expression cloning of a cocaine- and antidepressant-sensitive human noradrenaline transporter*. Nature (1991) volume 350, pages 350-354.

Human serotonin transporter: GenBank L05568. Reference: Ramamoorthy S, Bauman A L, Moore K R, Han H, Yang-Feng T, Chang A S, Ganaphthy V and Blakely R D. *Antidepressant- and cocaine-sensitive human serotonin transporter: Molecular cloning, expression, and chromosomal localization*. Proceedings of the National Academy of Sciences of the USA (1993) volume 90, pages 2542-2546.

The PCR products were cloned into a mammalian expression vector (eg pcDNA3.1 (Invitrogen)) using standard ligation techniques. The constructs were then used to stably transfect HEK293 cells using a commercially available lipofection reagent (Lipofectamine™-Invitrogen) following the manufacture's protocol.

Scintillation Proximity Assays for Determining the Affinity of Test Ligands at the Norepinephrine and Serotonin Transporters.

The compounds of the present invention are norepinephrine and serotonin reuptake inhibitors, and possess excellent activity in, for example, a scintillation proximity assay (e.g. J. Gobel, D. L. Saussy and A. Goetz, J. Pharmacol. Toxicolo. (1999), 42, 237-244). Thus $^3$H-nisoxetine binding to norepinephrine re-uptake sites in a cell line transfected with DNA encoding human norepinephrine transporter binding protein and similarly $^3$H-citalopram binding to serotonin re-uptake sites in a cell line transfected with DNA encoding human serotonin transporter binding protein have been used to determine the affinity of ligands at the norepinephrine and serotonin transporters respectively.

Norepinephrine Binding Assay

Membrane Preparation:

Cell pastes from large scale production of HEK-293 cells expressing cloned human norepinephrine transporters were homogenized in 4 volumes 50 mM Tris-HCl containing 300 mM NaCl and 5 mM KCl, pH 7.4. The homogenate was centrifuged twice (40,000 g, 10 min, 4° C.) with pellet resuspension in 4 volumes of Tris-HCl buffer containing the above reagents after the first spin and 8 volumes after the second spin. The suspended homogenate was centrifuged (100 g, 10 min, 4° C.) and the supernatant kept and recentrifuged (40,000 g, 20 min, 4° C.). The pellet was resuspended in Tris-HCl buffer containing the above reagents along with 10% w/v sucrose and 0.1 mM phenylmethylsulfonyl fluoride (PMSF). The membrane preparation was stored in aliquots (1 ml) at −80° C. until required. The protein concentration of the membrane preparation was determined using a bicinchoninic acid (BCA) protein assay reagent kit (available from Pierce).

[$^3$H]-Nisoxetine Binding Assay:

Each well of a 96 well microtitre plate was set up to contain the following:

50 μl  2 nM [N-methyl-$^3$H]-Nisoxetine hydrochloride (70-87 Ci/mmol, from NEN Life Science Products)
75 μl  Assay buffer (50 mM Tris-HCl pH 7.4 containing 300 mM NaCl and 5 mM KCl)
25 μl  Test compound, assay buffer (total binding) or 10 μM Desipramine HCl (non-specific binding)

50 μl  Wheatgerm agglutinin coated poly (vinyltoluene) (WGA PVT) SPA Beads (Amersham Biosciences RPNQ0001) (10 mg/ml)
50 μl  Membrane (0.2 mg protein per ml)

The microtitre plates were incubated at room temperature for 10 hours prior to reading in a Trilux scintillation counter. The results were analysed using an automatic spline fitting programme (Multicalc, Packard, Milton Keynes, UK) to provide Ki values for each of the test compounds.

Serotonin Binding Assay

The ability of a test compound to compete with [$^3$H]-citalopram for its binding sites on cloned human serotonin transporter containing membranes has been used as a measure of test compound ability to block serotonin uptake via its specific transporter (Ramamoorthy, S., Giovanetti, E., Qian, Y., Blakely, R., (1998) J. Biol. Chem. 273, 2458).

Membrane Preparation:

Membrane preparation is essentially similar to that for the norepinephrine transporter containing membranes as described above. The membrane preparation was stored in aliquots (1 ml) at −70° C. until required. The protein concentration of the membrane preparation was determined using a BCA protein assay reagent kit.

[$^3$H]-Citalopram Binding Assay:

Each well of a 96 well microtitre plate was set up to contain the following:

50 μl  2 nM [$^3$H]-Citalopram (60-86 Ci/mmol, Amersham Biosciences)
75 μl  Assay buffer (50 mM Tris-HCl pH 7.4 containing 150 mM NaCl and 5 mM KCl)
25 μl  Diluted compound, assay buffer (total binding) or 100 μM Fluoxetine (non-specific binding)
50 μl  WGA PVT SPA Beads (40 mg/ml)
50 μl  Membrane preparation (0.4 mg protein per ml)

The microtitre plates were incubated at room temperature for 10 hours prior to reading in a Trilux scintillation counter. The results were analysed using an automatic spline fitting programme Multicalc, Packard, Milton Keynes, UK) to provide Ki (nM) values for each of the test compounds.

Dopamine Binding Assay

The ability of a test compound to compete with [$^3$H]-WIN35,428 for its binding sites on human cell membranes containing cloned human dopamine transporter has been used as a measure of the ability of such test compounds to block dopamine uptake via its specific transporter (Ramamoorthy et al 1998 supra).

Membrane Preparation:

Is essentially the same as for membranes containing cloned human serotonin transporter as described above.

[$^3$H]-WIN35,428 Binding Assay:

Each well of a 96well microtitre plate was set up to contain the following:

| | |
|---|---|
| 50 µl | 4 nM [³H]-WIN35,428 (84-87 Ci/mmol, from NEN Life Science Products) |
| 75 µl | Assay buffer (50 mM Tris-HCl pH 7.4 containing 150 mM NaCl and 5 mM KCl) |
| 25 µl | Diluted compound, assay buffer (total binding) or 100 µM Nomifensine (non-specific binding) |
| 50 µl | WGA PVT SPA Beads (10 mg/ml) |
| 50 µl | Membrane preparation (0.2 mg protein per ml.) |

The microtitre plates were incubated at room temperature for 120 minutes prior to reading in a Trilux scintillation counter. The results were analysed using an automatic spline fitting programme (Multicalc, Packard, Milton Keynes, UK) to provide Ki values for each of the test compounds.

Formalin Paw Assay

The analgesic effect of compounds of the invention for the treatment of persistent nociceptive pain was demonstrated using the well-known "formalin test." The formalin test is a model of persistent nociceptive activation induced by tissue injury which can lead to central sensitization. (Shibata, M., Ohkubo, T., Takahashi, H., and Inoki, R., "Modified formalin test: Characteristic biphasic pain response," *Pain* (1989) 38: 347-352; and Tjolsen, A., Berge, O. G., Hunskaar, S., Rosland, J. H., and Hole, K., "The formalin test: an evaluation of the method," *Pain* (1992) 51:5-17.) The effect of compounds of the invention on formalin-induced paw-licking behavior in the rat was investigated as an index of persistent nociceptive activation. In this test, the injection of formalin under the skin on the dorsal lateral surface of the hind paw of rats causes an immediate and intense increase in the spontaneous activity of C fiber afferents. This activation evokes a distinctly quantifiable behavior indicative of pain, such as licking of the injected paw. The behavioral response to formalin is biphasic, with an early phase that is short lived, followed by an extended tonic response or late phase of persistent nociceptive activation. Mechanisms causing the late phase response, such as central sensitization of pain transmitting neurons, are currently believed to contribute to various types of persistent pains.

Male Sprague-Dawley rats (200-250 g; Charles River, Portage, Mich.) were maintained at constant temperature and light (12 h light/12 h dark) for 4-7 days prior to the studies. Animals had free access to food and water at all times prior to the day of the experiment.

Scoring in the formalin test was performed according to Coderre et al., 1993b and Abbott et al., 1995. (Coderre T. J., Fundytus M. E., McKenna J. E., Dalal S. and Melzack R. "The formalin test: a validation of the weighted-scores method of the behavioral pain rating," *Pain* (1993b) 54: 43-50; and Abbott F. V., Franklin K. B. J. and Westbrook R. F. "The formalin test: scoring properties of the first and second phases of the pain response in rats," *Pain* (1995) 60: 91-102.) The sum of time spent licking in seconds from time 0 to 5 minutes was considered the early phase while the late phase was taken as the sum of seconds spent licking from 15 to 40 minutes.

Data are presented as means with standard errors of means (±SEM). Data were evaluated by one-way analysis of variance (ANOVA) and the appropriate contrasts analyzed by Tukey's test and Dunnett "t' test for two-sided comparisons.

The preferred compounds of the present invention show good stability to the action of the CYP 2D6 enzyme. This is advantageous because it is likely to lead to improved metabolic stability of the compounds.

Stability to the CYP 2D6 enzyme may be determined according to the assay described below:

In Vitro Determination of the Interaction of Compounds with CYP2D6 in Human Hepatic Microsomes Cytochrome P450 2D6 (CYP2D6) is a mammalian enzyme which is commonly associated with the metabolism of around 30% of pharmaceutical compounds. Moreover, this enzyme shows a genetic polymorphism with as a consequence a presence in the population of poor and normal metabolizers. A low involvement of CYP2D6 in the metabolism of compounds (i.e. the compound being a poor substrate of CYP2D6) is desirable in order to reduce any variability from subject to subject in the pharmacokinetics of the compound. Also, compounds with a low inhihibitor potential for CYP2D6 are desirable in order to avoid drug-drug interactions with co-administered drugs that are substrates of CYP2D6. Compounds may be tested both as substrates and as inhibitors of this enzyme by means of the following assays.

CYP2D6 Substrate Assay

Principle:

This assay determines the extent of the CYP2D6 enzyme involvement in the total oxidative metabolism of a compound in microsomes. Preferred compounds of the present invention exhibit less than 75% total metabolism via the CYP2D6 pathway.

For this in vitro assay, the extent of oxidative metabolism in human liver microsomes (HLM) is determined after a 30 minute incubation in the absence and presence of Quinidine, a specific chemical inhibitor of CYP2D6. The difference in the extent of metabolism in absence and presence of the inhibitor indicates the involvement of CYP2D6 in the metabolism of the compound.

Materials and Methods:

Human liver microsomes (mixture of 20 different donors, mixed gender) were acquired from Human Biologics (Scottsdale, Ariz., USA). Quinidine and β-NADPH (β-Nicotinamide Adenine Dinucleotide Phosphate, reduced form, tetrasodium salt) were purchased from Sigma (St Louis, Mo., USA). All the other reagents and solvents were of analytical grade. A stock solution of the new chemical entity (NCE) was prepared in a mixture of Acetonitrile/Water to reach a final concentration of acetonitrile in the incubation below 0.5%.

The microsomal incubation mixture (total volume 0.1 mL) contained the NCE (4 µM), β-NADPH (1 mM), microsomal proteins (0.5 mg/mL), and Quinidine (0 or 2 µM) in 100 mM sodium phosphate buffer pH 7.4. The mixture was incubated for 30 minutes at 37° C. in a shaking waterbath. The reaction was terminated by the addition of acetonitrile (75 µL). The samples were vortexed and the denaturated proteins were removed by centrifugation. The amount of NCE in the supernatant was analyzed by liquid chromatography/mass spectrometry (LC/MS) after addition of an internal standard. A sample was also taken at the start of the incubation (t=0), and analysed similarly.

Analysis of the NCE was performed by liquid chromatography/mass spectrometry. Ten µL of diluted samples (20 fold dilution in the mobile phase) were injected onto a Spherisorb CN Column, 5 µM and 2.1 mm×100 mm (Waters corp. Milford, Mass., USA). The mobile phase consisting of a mixture of Solvent A/Solvent B, 30/70 (v/v) was pumped (Alliance 2795, Waters corp. Milford, Mass., USA) through the column at a flow rate of 0.2 ml/minute. Solvent A and Solvent B were a mixture of ammonium formate $5.10^{-3}$ M pH 4.5/methanol in the proportions 95/5 (v/v) and 10/90 (v/v), for solvent A and solvent B, respectively. The NCE and the internal standard were quantified by monitoring their molecular ion using a mass spectrometer ZMD or ZQ (Waters-Micromass corp, Machester, UK) operated in a positive electrospray ionisation.

The extent of CYP2D6 involvement (% of CYP2D6 involvement) was calculated comparing the extent of metabolism in absence and in presence of quinidine in the incubation.

The extent of metabolism without inhibitor (%) was calculated as follows:

$$\frac{(NCE \text{ response in samples without inhibitor}) \text{ time } 0 - (NCE \text{ response in samples without inhibitor}) \text{ time } 30}{(NCE \text{ response in samples without inhibitor}) \text{ time } 0} \times 100$$

The extent of metabolism with inhibitor (%) was calculated as follows:

$$\frac{(NCE \text{ response in samples without inhibitor}) \text{ time } 0 - (NCE \text{ response in samples with inhibitor}) \text{ time } 30}{(NCE \text{ response in samples without inhibitor}) \text{ time } 0} \times 100$$

where the NCE response is the area of the NCE divided by the area of the internal standard in the LC/MS analysis chromatogram, time0 and time30 correspond to the 0 and 30 minutes incubation time.

The % of CYP2D6 involvement was calculated as follows:

$$\frac{(\% \text{ extent of metabolism without inhibitor}) - (\% \text{ extent of metabolism with inhibitor})}{\% \text{ extent of metabolism without inhibitor}} \times 100$$

CYP2D6 Inhibitor Assay

Principle:

The CYP2D6 inhibitor assay evaluates the potential for a compound to inhibit CYP2D6. This is performed by the measurement of the inhibition of the bufuralol 1'-hydroxylase activity by the compound compared to a control. The 1'-hydroxylation of bufuralol is a metabolic reaction specific to CYP2D6. Preferred compounds of the present invention exhibit an $IC_{50}$ higher than 6 µM for CYP2D6 activity, the $IC_{50}$ being the concentration of the compound that gives 50% of inhibition of the CYP2D6 activity.

Material and Methods:

Human liver microsomes (mixture of 20 different donors, mixed gender) were acquired from Human Biologics (Scottsdale, Ariz.). β-NADPH was purchased from Sigma (St Louis, Mo.). Bufuralol was purchased from Ultrafine Manchester, UK). AR the other reagents and solvents were of analytical grade.

Microsomal incubation mixture (total volume 0.1 mL) contained bufuralol 10 µM, β-NADPH (2 mM), microsomal proteins (0.5 mg/mL), and the new chemical entity (NCE) (0, 5, and 25 µM) in 100 mM sodium phosphate buffer pH 7.4. The mixture was incubated in a shaking waterbath at 37° C. for 5 minutes. The reaction was terminated by the addition of methanol (75 µL). The samples were vortexed and the denaturated proteins were removed by centrifugation. The supernatant was analyzed by liquid chromatography connected to a fluorescence detector. The formation of the 1'-hydroxybufuralol was monitored in control samples (0 µM NCE) and in the samples incubated in presence of the NCE. The stock solution of NCE was prepared in a mixture of Acetonitrile/Water to reach a final concentration of acetonitrile in the incubation below 1.0%.

The determination of 1'hydroxybufuralol in the samples was performed by liquid chromatograhy with fluorimetric detection as described below. Twenty five µL samples were injected onto a Chromolith Performance RP-18e column (100 mm×4.6 mm) (Merck KGAa, Darmstadt, Germany). The mobile phase, consisting of a mixture of solvent A and solvent B whose the proportions changed according the following linear gradient, was pumped through the column at a flow rate of 1 ml/min:

| Time (minutes) | Solvent A (%) | Solvent B (%) |
|---|---|---|
| 0 | 65 | 35 |
| 2.0 | 65 | 35 |
| 2.5 | 0 | 100 |
| 5.5 | 0 | 100 |
| 6.0 | 65 | 35 |

Solvent A and Solvent B consisted of a mixture of 0.02 M potassium dihydrogenophosphate buffer pH3/methanol in the proportion 90/10 (v/v) for solvent A and 10/90 (v/v) for solvent B. The run time was 7.5 minutes. Formation of 1'-hydroxybufuralol was monitored by fluorimetric detection with extinction at λ 252 nm and emission at λ 302 nm.

The $IC_{50}$ of the NCE for CYP2D6 was calculated by the measurement of the percent of inhibition of the formation of the 1'-hydroxybufuralol in presence of the NCE compared to control samples (no NCE) at a known concentration of the NCE.

The percent of inhibition of the formation of the 1'-hydroxybufuralol is calculated as follows:

$$\frac{(1'\text{-hydroxybufuralol formed without inhibitor}) - (1'\text{-hydroxybufuralol formed with inhibitor})}{(1'\text{-hydroxybufuralol area formed without inhibitor})} \times 100$$

The $IC_{50}$ is calculated from the percent inhibition of the formation of the 1'-hydroxybufuralol as follows (assuming competitive inhibition):

$$\frac{NCE \text{ Concentration} \times (100 - \text{Percent of inhibitor})}{\text{Percent of inhibiton}}$$

The $IC_{50}$ estimation is assumed valid if inhibition is between 20% and 80% (Moody G C, Griffin S J, Mather A N, McGinnity D F, Riley R J. 1999. Fully automated analysis of activities catalyzed by the major human liver cytochrome P450 (CYP) enzymes: assessment of human CYP inhibition potential. Xenobiotica, 29(1): 53-75).

The invention claimed is:

1. A compound of formula I:

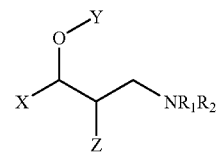

I wherein
X is phenyl optionally substituted with fluorine
Y is benzothienyl, optionally substituted with fluorine
Z is selected from OH or F,
$R_1$ and $R_2$ are each independently H or $C_1$-$C_4$ alkyl; or a pharmaceutically acceptable salt thereof.

2. A compound as claimed in claim 1, wherein one of $R_1$ and $R_2$ is H and the other is methyl.

3. A pharmaceutical composition comprising a compound of formula I or a pharmaceutically acceptable salt thereof, as defined in claim 1, together with a pharmaceutically acceptable diluent or carrier.

* * * * *